United States Patent
Hwang et al.

(10) Patent No.: US 10,050,217 B2
(45) Date of Patent: Aug. 14, 2018

(54) ORGANIC COMPOUND AND ORGANIC LIGHT EMITTING DIODE DEVICE INCLUDING THE SAME

(71) Applicants: Samsung Display Co., Ltd., Yongin, Gyeonggi-Do (KR); Sungkyunkwan University Research & Business Foundation, Suwon-si, Gyeonggi-do (KR)

(72) Inventors: Jin Soo Hwang, Seoul (KR); Myeong Suk Kim, Hwaseong-si (KR); Sung Wook Kim, Hwaseong-si (KR); Jae Hong Kim, Suwon-si (KR); Seung-Soo Yoon, Suwon-si (KR)

(73) Assignees: Samsung Display Co., Ltd., Gyeonggi-do (KR); Sungkyunkwan University Research & Business Foundation, Gyeonggi-do (KR)

( * ) Notice: Subject to any disclaimer, the term of this patent is extended or adjusted under 35 U.S.C. 154(b) by 326 days.

(21) Appl. No.: 14/710,488

(22) Filed: May 12, 2015

(65) Prior Publication Data

US 2016/0126479 A1    May 5, 2016

(30) Foreign Application Priority Data

Nov. 4, 2014 (KR) .................. 10-2014-0152181

(51) Int. Cl.
*H01L 51/00* (2006.01)
*C07D 333/78* (2006.01)
(Continued)

(52) U.S. Cl.
CPC ........ *H01L 51/0074* (2013.01); *C07D 333/78* (2013.01); *C09K 11/025* (2013.01);
(Continued)

(58) Field of Classification Search
CPC .... B01J 31/249; C07D 221/20; C07D 209/96; C07D 333/50; C07D 307/94; C07C 13/72; C07C 2603/93–2603/97
See application file for complete search history.

(56) References Cited

U.S. PATENT DOCUMENTS 9,905,774 B2 * 2/2018 Dai .................. H01L 51/0058
2007/0116984 A1 * 5/2007 Park ................... C07D 221/20
428/690

FOREIGN PATENT DOCUMENTS

| KR | 10-2009-0014458 A | 2/2009 |
| KR | 10-2009-0088309 A | 8/2009 |
| KR | 10-2012-0043623 A | 5/2012 |

OTHER PUBLICATIONS

Cyril Poriel and Joëlle Rault-Berthelot "Structure-property relationship of 4-substituted-spirobifluorenes as hosts for phosphorescent organic light emitting diodes: an overview" J. Mater. Chem. C, 2017, 5, 3869-3897.*

* cited by examiner

*Primary Examiner* — Randy P Gulakowski
*Assistant Examiner* — Christina H Wales
(74) *Attorney, Agent, or Firm* — Knobbe, Martens, Olson & Bear LLP

(57) ABSTRACT

An organic compound represented by Chemical Formula 1 is disclosed. Also a light emitting diode including the organic compound is described.

[Chemical Formula 1]

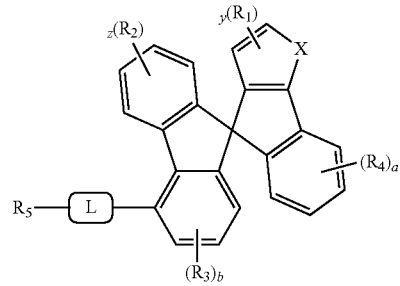

18 Claims, 1 Drawing Sheet

(51) Int. Cl.
    *C09K 11/06*          (2006.01)
    *C09K 11/02*          (2006.01)
    *H01L 51/50*           (2006.01)
    *C07D 333/50*        (2006.01)
    *C07D 209/96*        (2006.01)
    *C07D 307/94*        (2006.01)

(52) U.S. Cl.
    CPC .......... *C09K 11/06* (2013.01); *H01L 51/0058* (2013.01); *H01L 51/0068* (2013.01); *C07C 2603/96* (2017.05); *C07D 209/96* (2013.01); *C07D 307/94* (2013.01); *C07D 333/50* (2013.01); *C09K 2211/1007* (2013.01); *C09K 2211/1011* (2013.01); *C09K 2211/1092* (2013.01); *H01L 51/0085* (2013.01); *H01L 51/5016* (2013.01); *H01L 51/5072* (2013.01)

ORGANIC COMPOUND AND ORGANIC LIGHT EMITTING DIODE DEVICE INCLUDING THE SAME

CROSS-REFERENCE TO RELATED APPLICATION

This application claims priority to and the benefit of Korean Patent Application No. 10-2014-0152181 filed in the Korean Intellectual Property Office on Nov. 4, 2014, the entire contents of which are incorporated herein by reference.

BACKGROUND

Field

The present embodiments relate to an organic compound and an organic emitting diode device including the same.

Description of the Related Art

Recently, as thin and light-weight monitors and television sets have been required, the cathode ray tube (CRT) is being replaced by a liquid crystal display (LCD). However, the liquid crystal display, which is a light receiving element, requires a separate backlight, and has a limitation in response speed, viewing angle, and the like.

As a display device capable of overcoming the aforementioned limitation, an organic light emitting device, which is a self-emitting display element, having advantages of a wide viewing angle, excellent contrast, and a fast response time has greatly attracted attention.

The organic light emitting device includes two electrodes facing each other and an organic layer interposed between the two electrodes. In the organic light emitting diode device, electrons injected from one electrode and holes injected from another electrode are combined with each other in an emission layer, thereby generating excitons, and energy is outputted from the excitons to thereby emit light. The organic light emitting diode device may be applicable to various fields including a display device and an illumination system.

In the organic light emitting diode device, characteristics of a material forming the organic layer may largely affect electrical characteristics of the organic light emitting diode device.

The above information disclosed in this Background section is only for enhancement of understanding of the background of the present embodiments and therefore it may contain information that does not form the prior art that is already known in this country to a person of ordinary skill in the art.

SUMMARY

The present embodiments provide a new organic compound applied to an organic emitting diode device, and an organic emitting diode device including the same.

An organic compound according to an example embodiment is an organic compound represented by Chemical Formula 1.

[Chemical Formula 1]

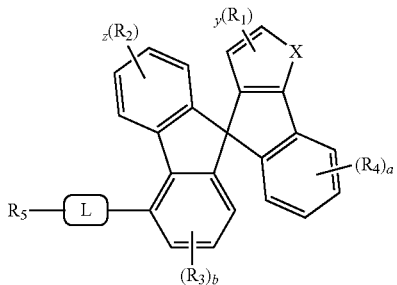

In Chemical Formula 1, $R_1$ to $R_5$ are a hydrogen atom, a heavy hydrogen, a C1 to C60 substituted or non-substituted alkyl group, a C2 to C60 substituted or non-substituted alkenyl group, a C2 to C60 substituted or non-substituted alkynyl group, a C3 to C60 substituted or non-substituted cycloalkyl group, a C1 to C60 substituted or non-substituted alkoxy group, a C5 to C60 substituted or non-substituted aryloxy group, a C5 to C60 substituted or non-substituted arylthio group, a C5 to C60 substituted or non-substituted aryl group, an amino group substituted into a C3 to C60 heteroaryl group, a C3 to C60 substituted or non-substituted heteroaryl group, a C6 to C60 substituted or non-substituted condensation polycyclic group, a halogen atom, a cyano group, a nitro group, a hydroxyl group, or a carboxyl group, $R_1$ and $R_2$ are the same as or different from each other, X is a linking group represented by —S—, —O—, —C($R_6$)($R_7$)—, or —N($R_6$)—, $R_6$ and $R_7$ are independently the hydrogen atom, the heavy hydrogen, a C1 to C20 substituted or non-substituted alkyl group, a C5 to C20 substituted or non-substituted aryl group, a C3 to C20 substituted or non-substituted hetero aryl group, a C6 to C20 substituted or non-substituted condensation polycyclic group, the halogen atom, the cyano group, the nitro group, the hydroxyl group, or the carboxyl group, a and z are an integer of 0 to 4, b is an integer of 0 to 3, and y is an integer of 0 to 2, L is a divalent linking group represented by —(Ar$_1$)$_n$—, and n is an integer of 1 to 10.

The Ar$_1$ may be a C5 to C60 substituted or non-substituted arylene group, a C3 to C60 substituted or non-substituted heteroarylene group, or a C6 to C60 substituted or non-substituted condensation polycyclic group.

The n Ar$_1$ may be the same as or different from each other, and two or more Ar$_1$ among the n Ar$_1$ may be fused to each other or linked to each other by a single bond.

The compound represented by Chemical Formula 1 may include at least one selected from compounds represented by Chemical Formula 2 to Chemical Formula 70.

[Chemical Formula 2]
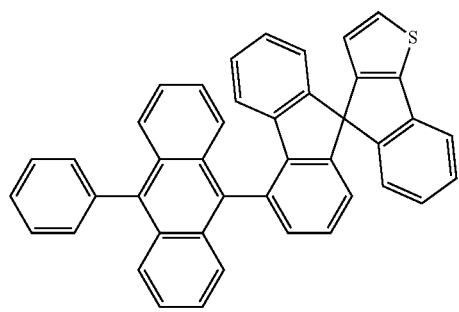
[Chemical Formula 3]
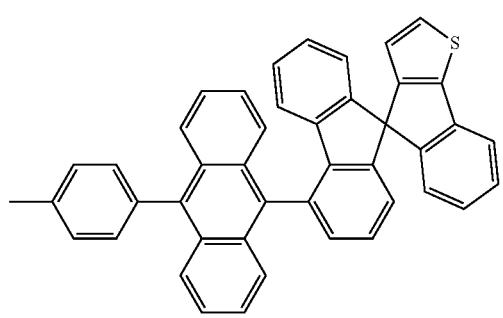
[Chemical Formula 4]
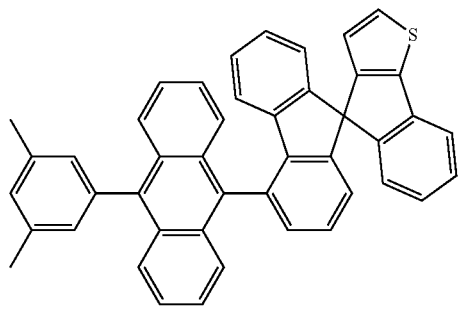
[Chemical Formula 5]
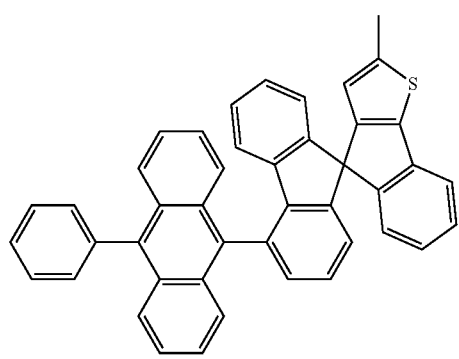 [SMILES: Cc1cc2c(s1)-c1ccccc1C21c2ccccc2-c2c(-c3c4ccccc4c(-c4ccccc4)c4ccccc34)cccc21]
[Chemical Formula 6]
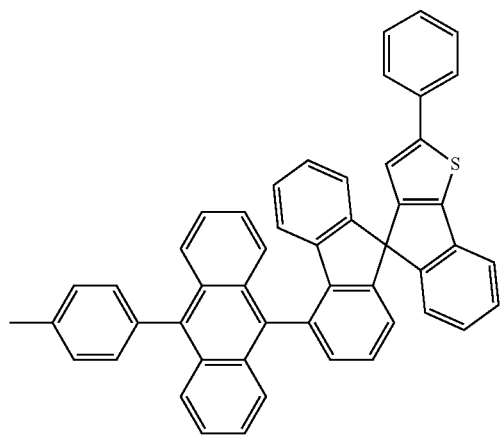
[Chemical Formula 7]
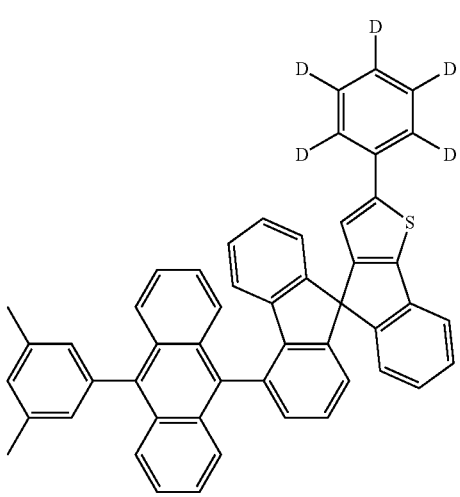
[Chemical Formula 8]
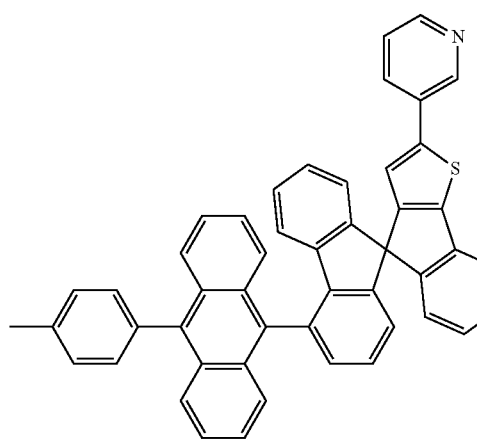

[Chemical Formula 9]
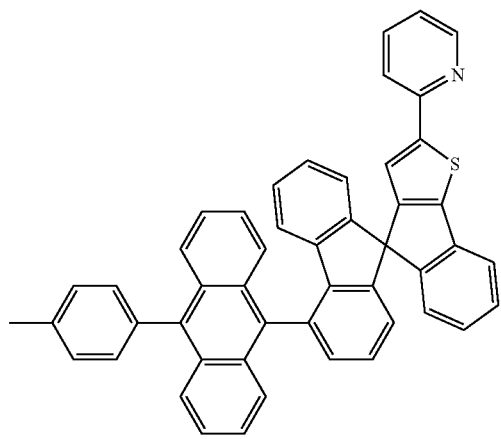
[Chemical Formula 10]
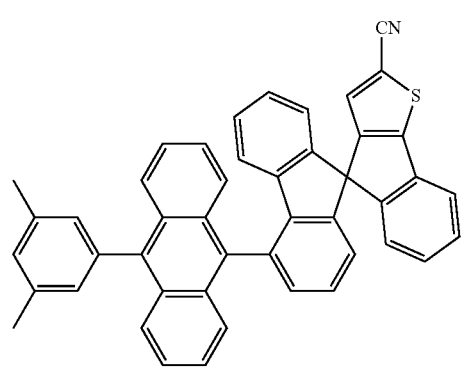
[Chemical Formula 11]
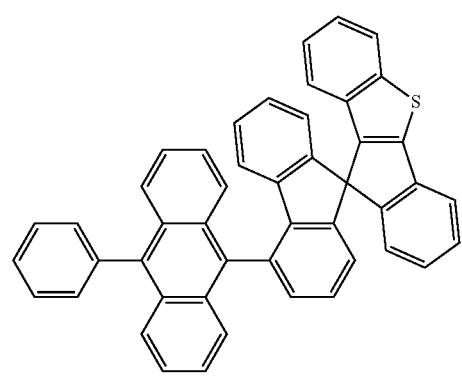
[Chemical Formula 12]
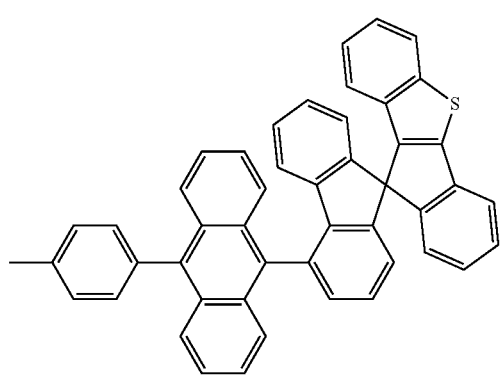
[Chemical Formula 13]
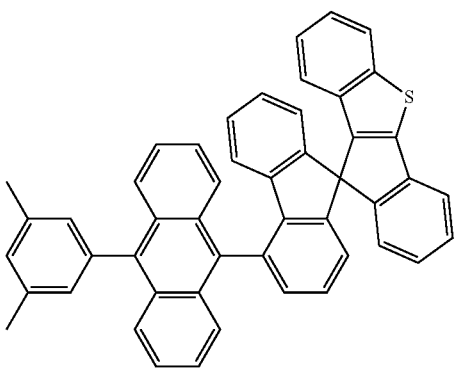
[Chemical Formula 14]
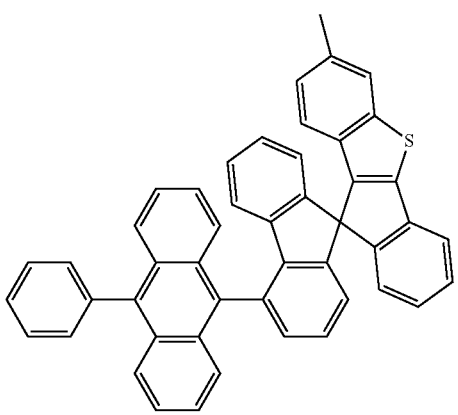
[Chemical Formula 15]
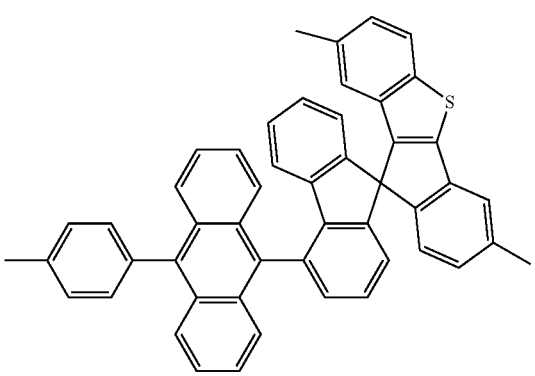
[Chemical Formula 16]
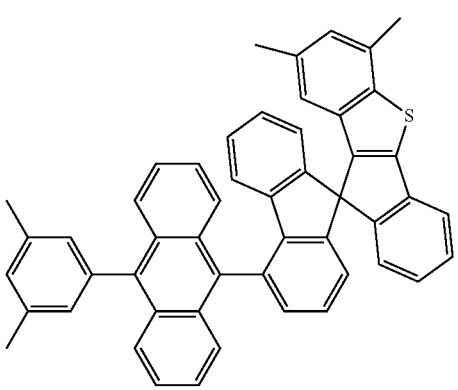

[Chemical Formula 17]
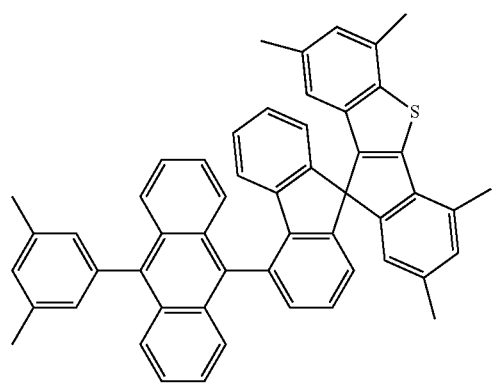
[Chemical Formula 18]
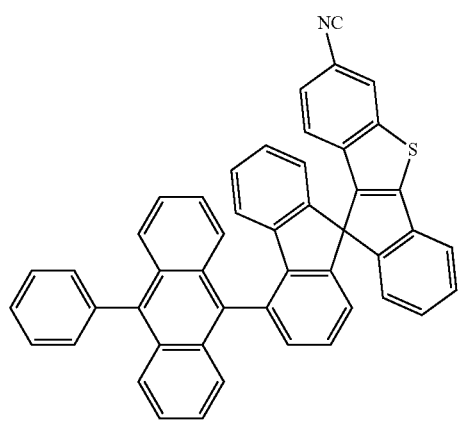
[Chemical Formula 19]
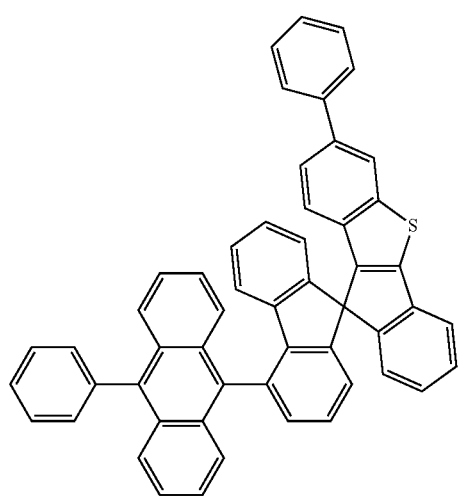
[Chemical Formula 20]
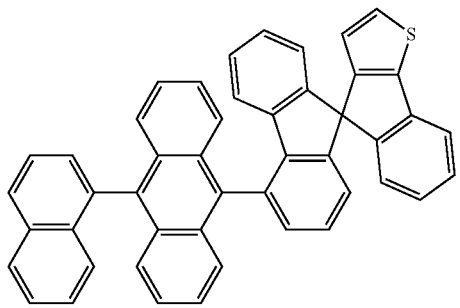
[Chemical Formula 21]
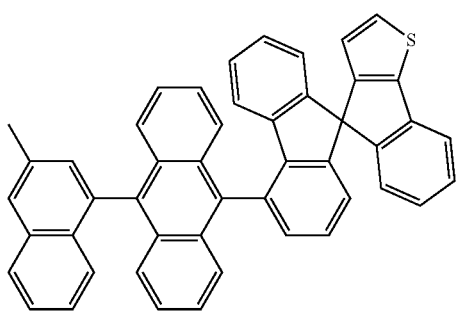
[Chemical Formula 22]
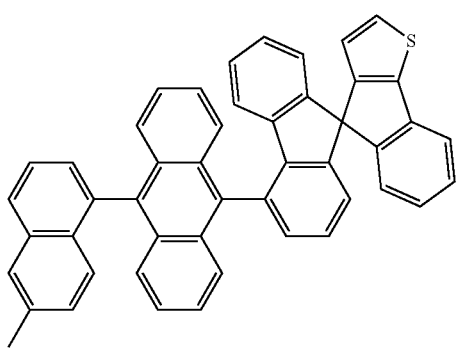
[Chemical Formula 23]
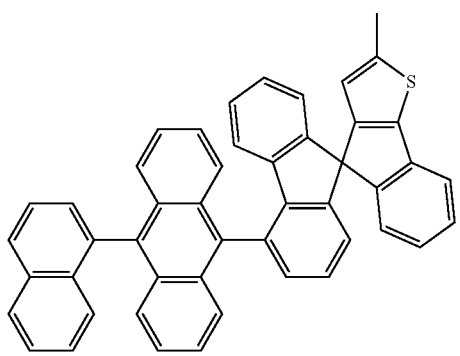

[Chemical Formula 24]
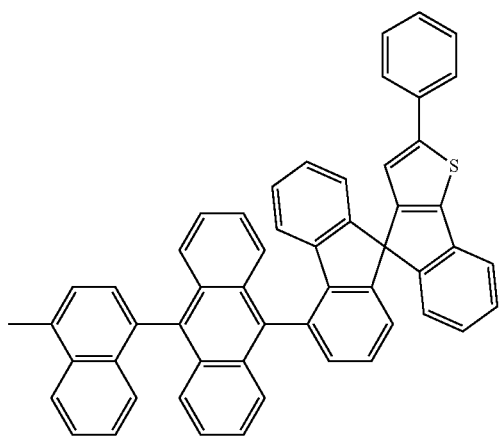
[Chemical Formula 25]
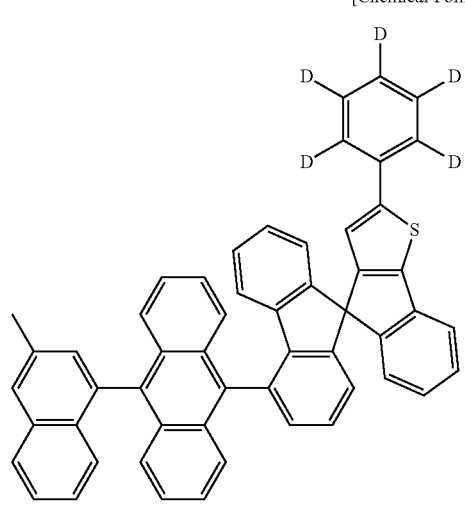
[Chemical Formula 26]
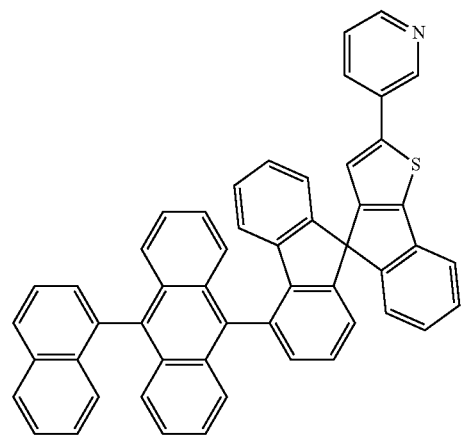
[Chemical Formula 27]
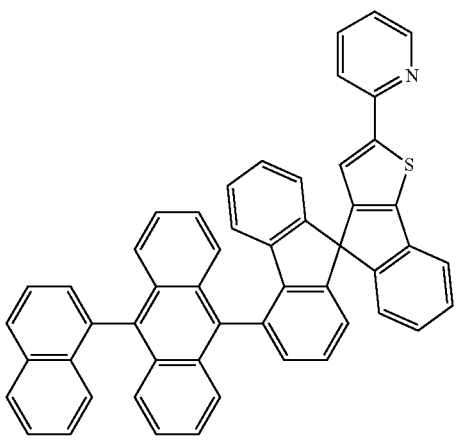
[Chemical Formula 28]
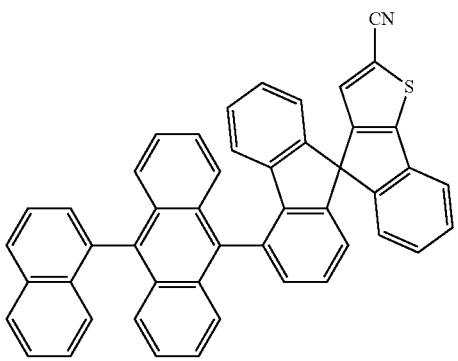
[Chemical Formula 29]
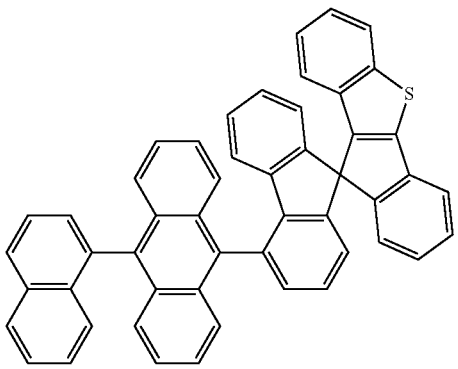
[Chemical Formula 30]
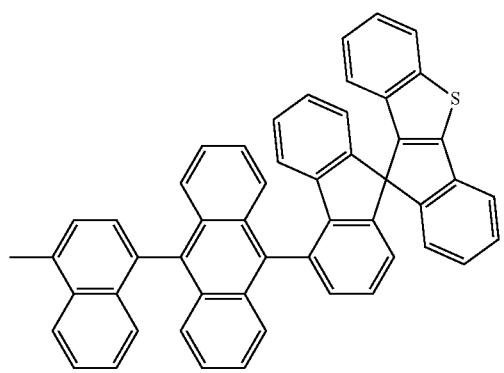

[Chemical Formula 31]
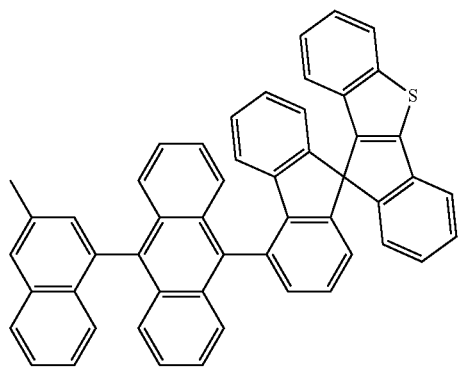
[Chemical Formula 32]
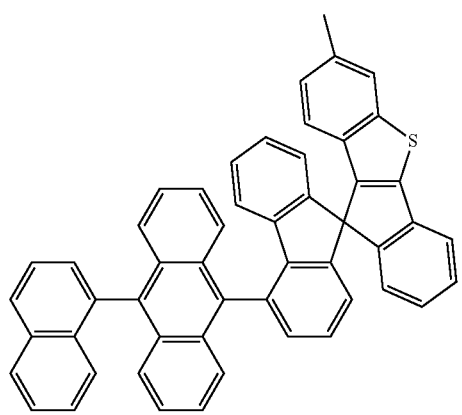
[Chemical Formula 33]
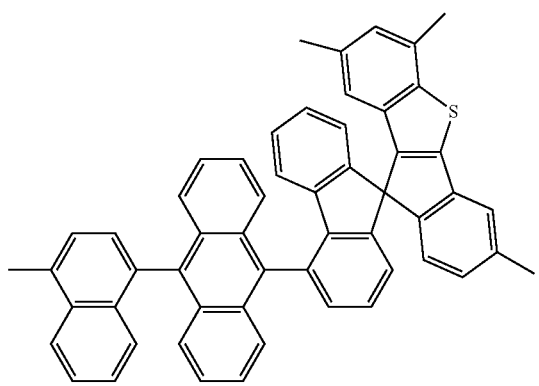
[Chemical Formula 34]
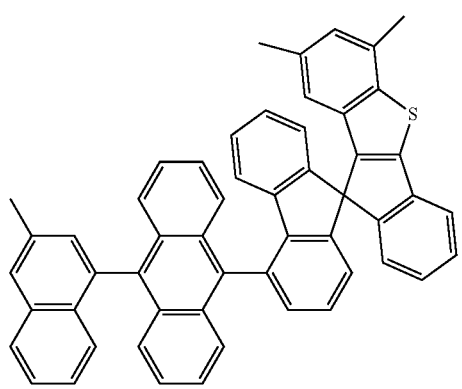
[Chemical Formula 35]
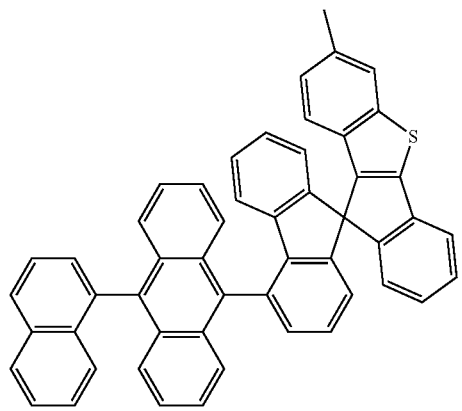
[Chemical Formula 36]
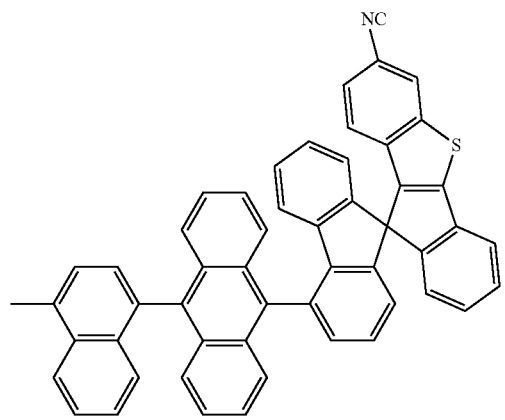
[Chemical Formula 37]
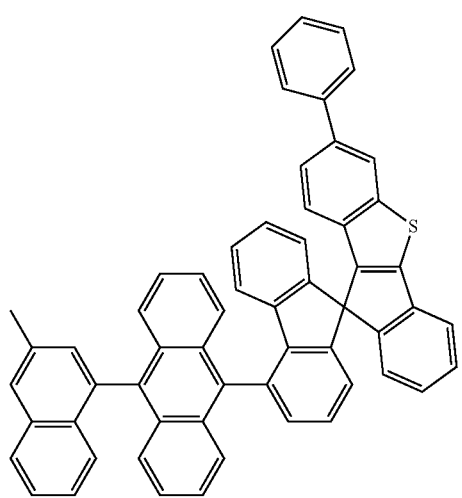

[Chemical Formula 38]
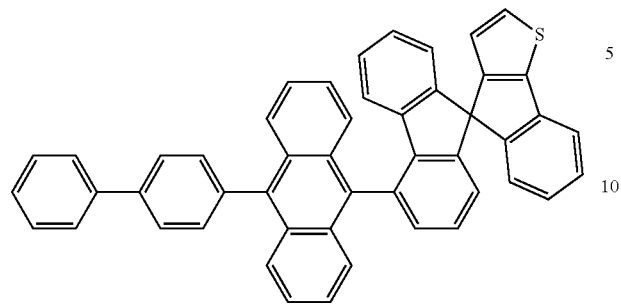
[Chemical Formula 39]
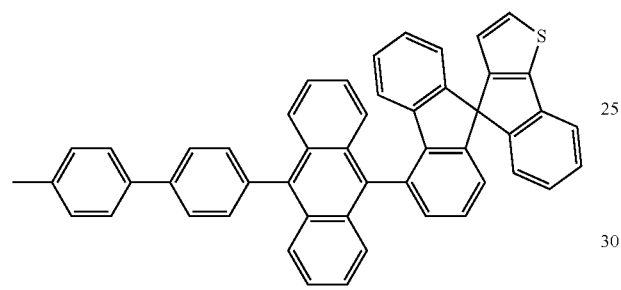
[Chemical Formula 40]
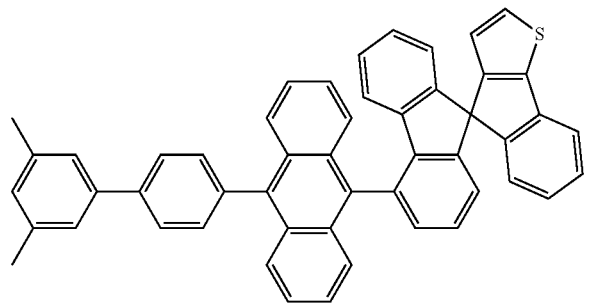
[Chemical Formula 41]
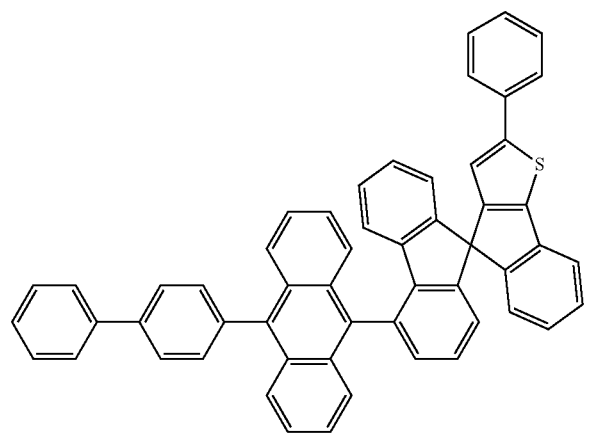
[Chemical Formula 42]
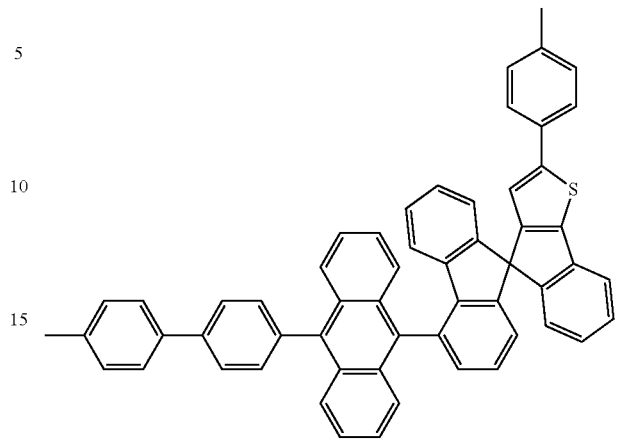
[Chemical Formula 43]
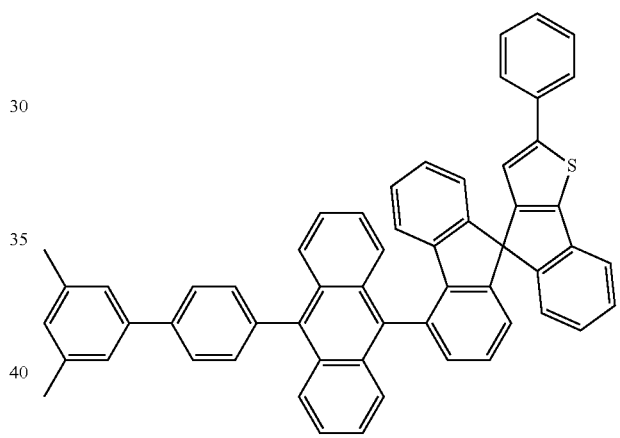
[Chemical Formula 44]
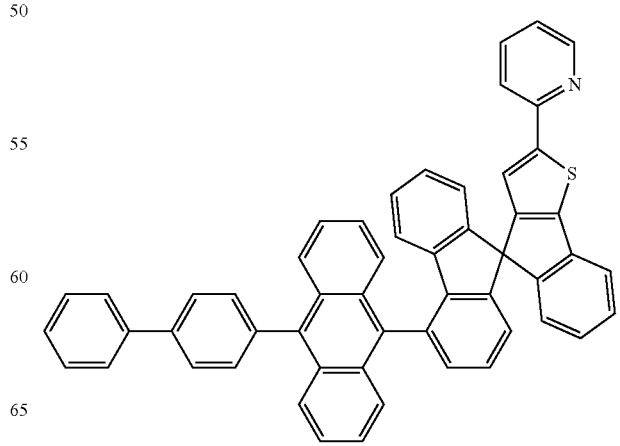

[Chemical Formula 45]
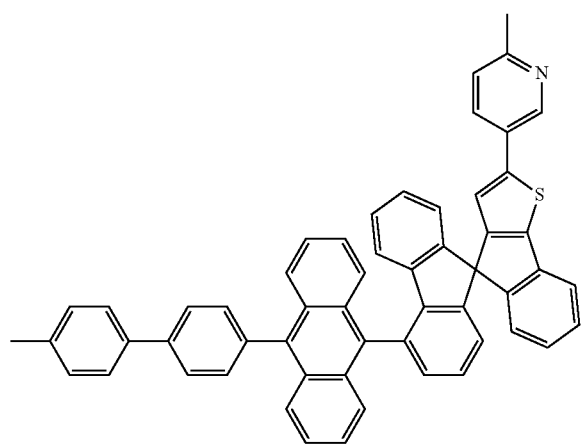
[Chemical Formula 46]
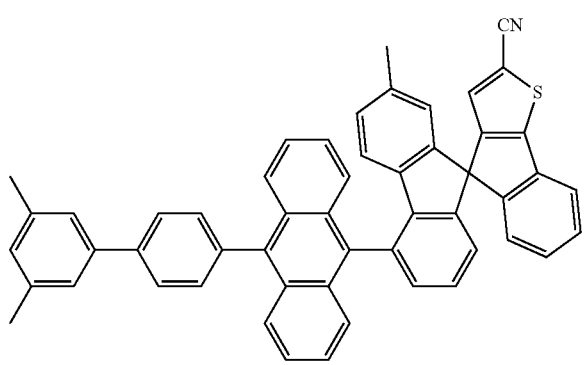
[Chemical Formula 47]
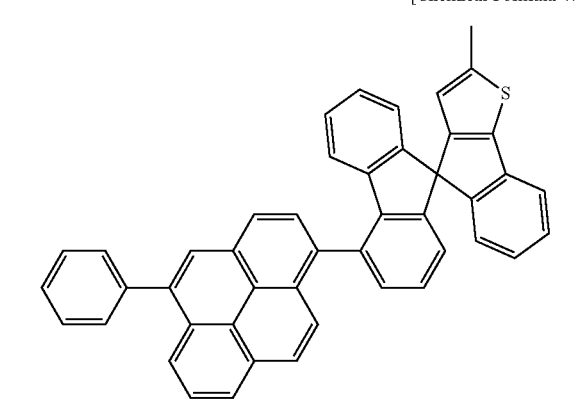
[Chemical Formula 48]
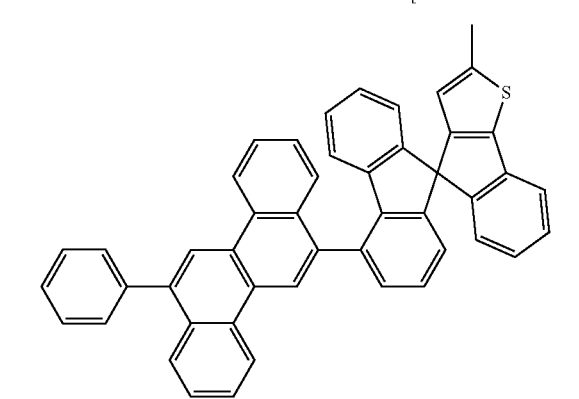
[Chemical Formula 49]
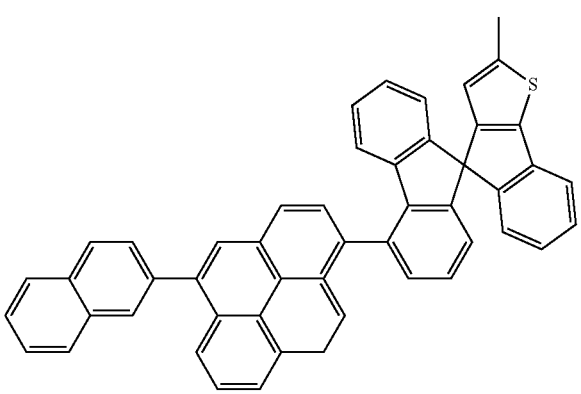
[Chemical Formula 50]
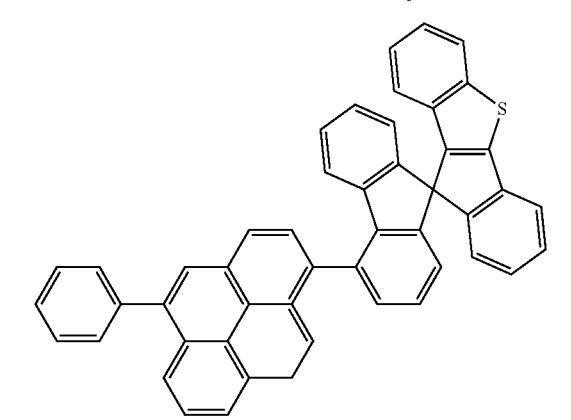
[Chemical Formula 51]
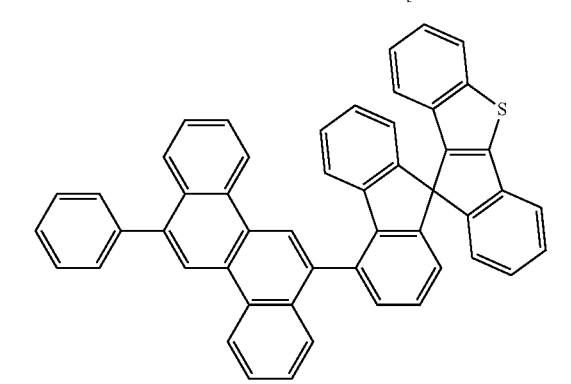
[Chemical Formula 52]
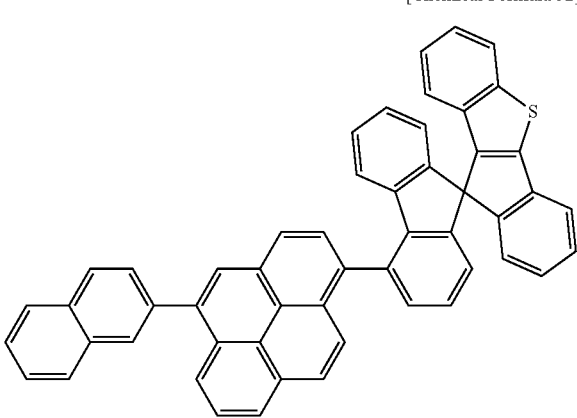

[Chemical Formula 53]
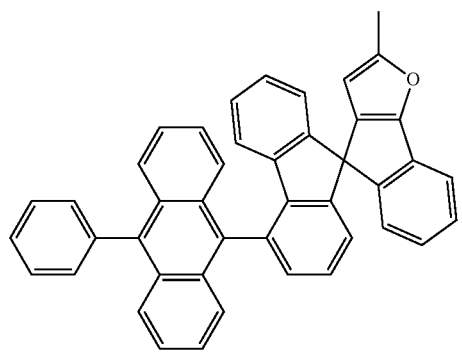
[Chemical Formula 54]
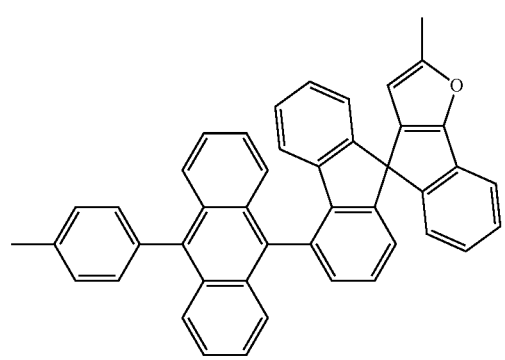
[Chemical Formula 55]
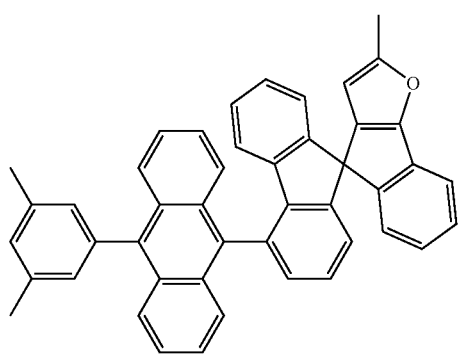
[Chemical Formula 56]
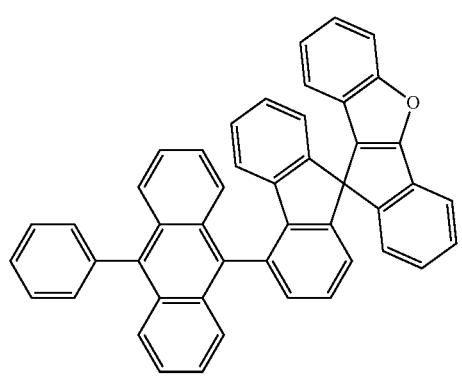
[Chemical Formula 57]
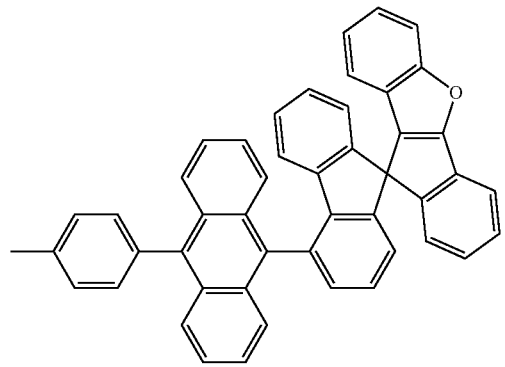
[Chemical Formula 58]
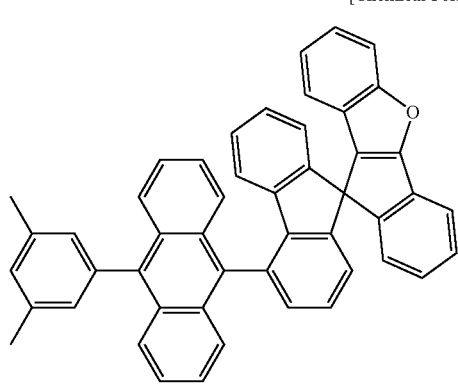
[Chemical Formula 59]
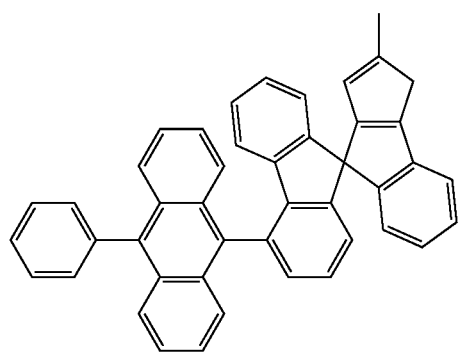
[Chemical Formula 60]
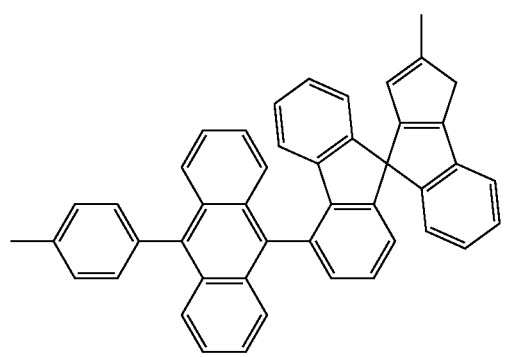

[Chemical Formula 61]
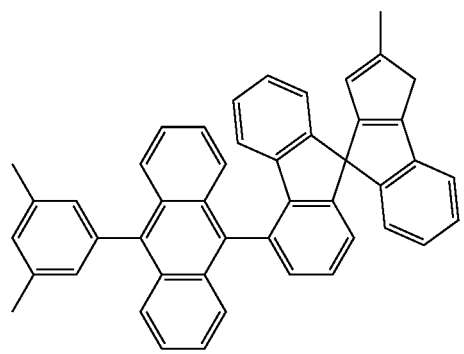
[Chemical Formula 62]
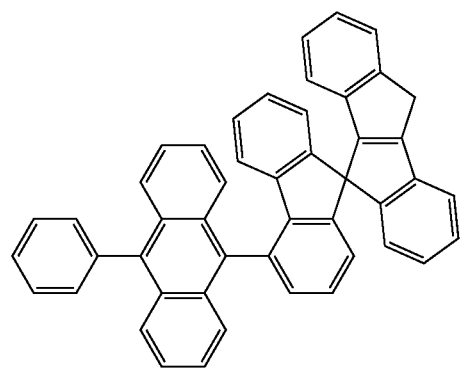
[Chemical Formula 63]
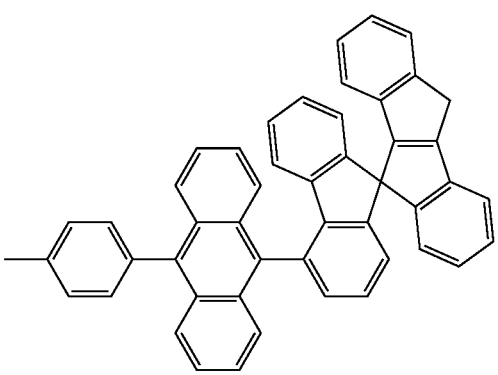
[Chemical Formula 64]
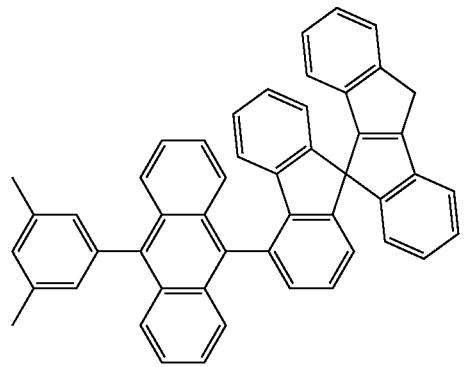
[Chemical Formula 65]
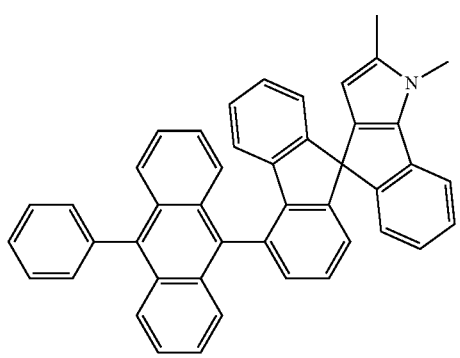
[Chemical Formula 66]
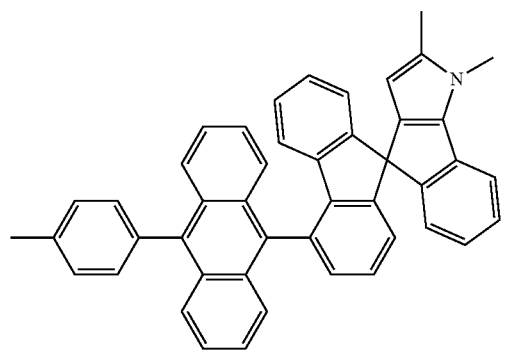
[Chemical Formula 67]
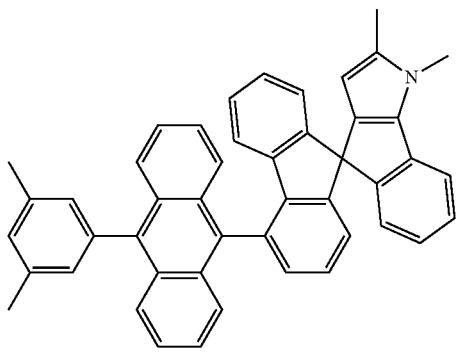
[Chemical Formula 68]
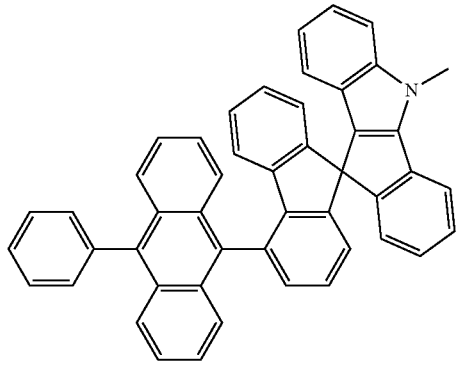

-continued

[Chemical Formula 69]

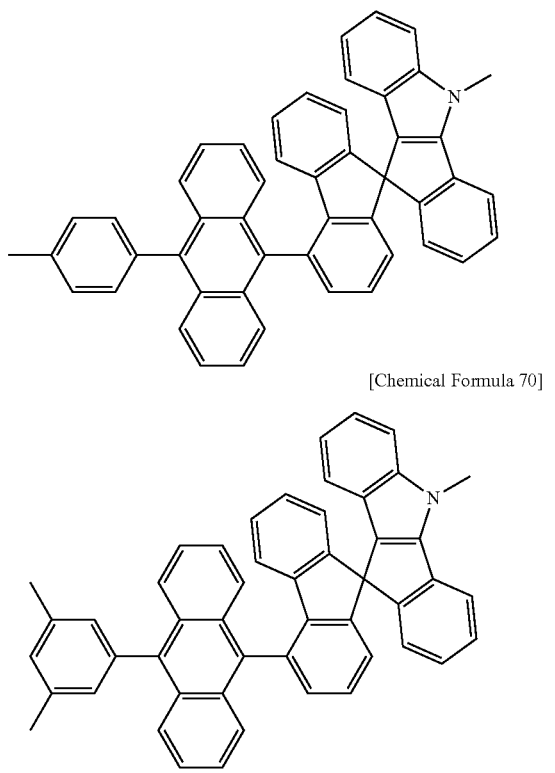

[Chemical Formula 70]

An organic emitting diode device according to an example embodiment includes: a first electrode; a second electrode; and an organic layer interposed between the first electrode and the second electrode, wherein the organic layer includes an organic compound represented by Chemical Formula 1.

The organic layer may include an emission layer, and the organic compound represented by Chemical Formula 1 may be included in the emission layer.

The emission layer may include the organic compound represented by Chemical Formula 1 as a host.

The emission layer may include the organic compound represented by Chemical Formula 1 as a dopant.

The first electrode may be an anode, and the second electrode may be a cathode.

The organic layer may further include a hole injection layer disposed between the first electrode and the emission layer, a hole transfer layer disposed between the hole injection layer and the emission layer, an electron transfer layer disposed between the emission layer and the second electrode, and an electron injection layer disposed between the electron transfer layer and the second electrode.

According to the present embodiments, the compound represented by Chemical Formula 1 has excellent electrical characteristics and emission capacity, and may be used as the emission material, the hole transfer material, or the electron transfer material of the organic emitting diode device.

Accordingly, the organic electroluminescence element with the high efficiency and low voltage may be manufactured by using the compound represented by Chemical Formula 1.

BRIEF DESCRIPTION OF THE DRAWING

FIG. 1 is a view of an organic emitting diode device according to an example embodiment.

DETAILED DESCRIPTION

Hereafter, an organic material and an organic light emitting device including the same according to example embodiments will be described. The example embodiments described herein are provided to allow a skilled person in the art to easily understand the idea of the present embodiments, and the present embodiments are not meant to be limited thereto. The example embodiments described herein may be modified within the technical idea and scope of the present embodiments.

In the present example embodiment, unless otherwise specified, "substituted" refers to a hydrogen atom of a compound substituted with a substituent selected from among halogen atoms (F, Br, Cl, or I), a hydroxyl group, an alkoxy group, a nitro group, a cyano group, an amino group, an azido group, an amidino group, a hydrazino group, a hydrazono group, a carbonyl group, a carbamyl group, a thiol group, an ester group, a carboxyl group or its salt, a sulfonic acid group or its salt, a phosphoric acid or its salt, an alkyl group, a C2-C16 alkenyl group, a C2-C16 alkynyl group, an aryl group, a C7-C13 arylalkyl group, a C1-C4 oxyalkyl group, a C1-C20 heteroalkyl group, a C3-C20 heteroaryl alkyl group, a cycloalkyl group, a C3-C15 cycloalkenyl group, a C6-C15 cycloalkynyl group, a heterocycloalkyl group, and combinations thereof.

Also, unless otherwise specified, "hetero" refers to containing one to three hetero atoms selected from among N, O, S, and P.

In the present example embodiment, "and/or" is used to include at least one among constituent elements arranged before and after. In the present example embodiment, each element and/or parts are designated by using expressions such as "first", "second", etc., but these are used for clarification and the present embodiments are not limited thereto.

In the present example embodiment, it will be understood that when an element is referred to as being "on" another element, it can be directly on the other element or intervening elements may also be present.

In the drawings, the thickness and/or relative thickness of the elements may be exaggerated in order to clarify embodiments of the present embodiments. Also, the expressions related to positions such as "upper part", "lower part", or the like are relatively used for clarification, without limiting absolute positions among the elements.

An organic light emitting device according to an example embodiment will now be described.

The organic compound according to an example embodiment may be represented by Chemical Formula 1.

[Chemical Formula 1]

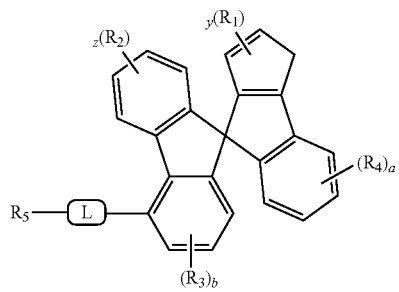

In [Chemical Formula 1],
$R_1$ to $R_5$ may be a hydrogen atom, a heavy hydrogen, a C1 to C60 substituted or non-substituted alkyl group, a C2 to C60 substituted or non-substituted alkenyl group, a C2 to C60 substituted or non-substituted alkynyl group, a C3 to C60 substituted or non-substituted cycloalkyl group, a C1 to C60 substituted or non-substituted alkoxy group, a C5 to C60 substituted or non-substituted aryloxy group, a C5 to C60 substituted or non-substituted arylthio group, a C5 to C60 substituted or non-substituted aryl group, an amino group substituted into a C3 to C60 heteroaryl group, a C3 to C60 substituted or non-substituted heteroaryl group, a C6 to C60 substituted or non-substituted condensation polycyclic group, a halogen atom, a cyano group, a nitro group, a hydroxyl group, or a carboxyl group, $R_1$ and $R_2$ may be the same as or different from each other, X is a linking group represented by —S—, —O—, —C($R_6$)($R_7$)—, or —N($R_6$)—, $R_6$ and $R_7$ are independently the hydrogen atom, the heavy hydrogen, the C1 to C20 substituted or non-substituted alkyl group, the C5 to 20 substituted or non-substituted aryl group, the C3 to C20 substituted or non-substituted hetero aryl group, the C6 to C20 substituted or non-substituted condensation polycyclic group, the halogen atom, the cyano group, the nitro group, the hydroxyl group, or the carboxyl group, a and z are an integer of 0 to 4, b is an integer of 0 to 3, and y is an integer of 0 to 2, L is a divalent linking group represented by —$(Ar_1)_n$—, $Ar_1$ is the C5 to C60 substituted or non-substituted arylene group, the C3 to C60 substituted or non-substituted heteroarylene group, or the C6 to C60 substituted or non-substituted condensation polycyclic group, N is the integer of 1 to 10, n $Ar_1$ may be the same as or different from each other, and the adjacent two or more $Ar_1$ among the n $Ar_1$ may be fused to each other or linked to each other by a single bond.

The compound represented by Chemical Formula 1 according to an example embodiment may function as an emission material, a hole transfer material, or an electron transfer material of the organic emitting diode device.

For example, the compound represented by Chemical Formula 1 may be a material for blue emission, but is not limited thereto.

The compound represented by Chemical Formula 1 has excellent blue quantum efficiency, when it is applied to the organic emitting diode device, thereby obtaining an excellent effect for color reproducibility improvement.

Also, the compound represented by Chemical Formula 1 includes a structure in which fluorene and benzothiophene are combined, and a single wavelength may be realized.

Further, the compound represented by Chemical Formula 1 blocks crystallization by substituting a ninth carbon position of fluorene into a substitution member, thereby increasing stability and efficiency of a thin film.

An example of the compound represented by Chemical Formula 1 may be at least one selected compounds disposed in a compound represented by Chemical Formula 2 to Chemical Formula 70, but is not limited thereto. The compounds disposed in a compound represented by Chemical Formula 2 to Chemical Formula 70 may be independently used, at least two or more may be mixed to be used, and they may be mixed with a different compound to be used.

[Chemical Formula 2]

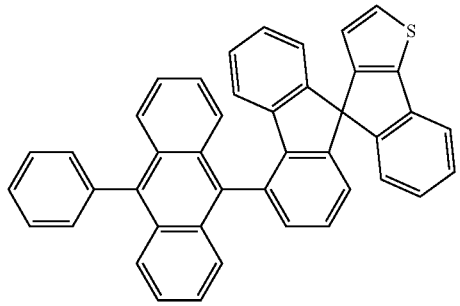

[Chemical Formula 3]

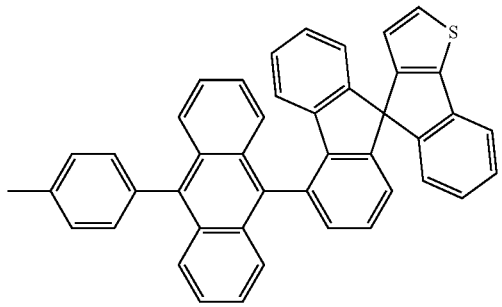

[Chemical Formula 4]

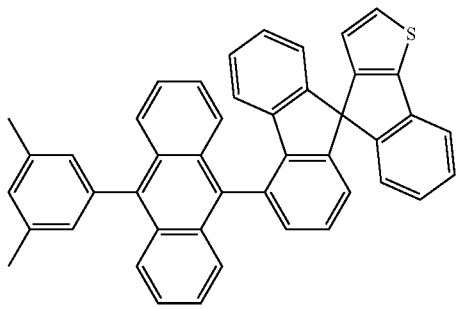

[Chemical Formula 5]

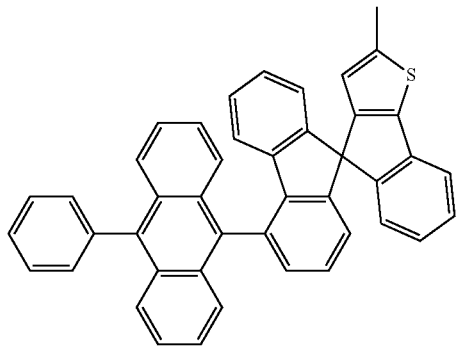

[Chemical Formula 6]
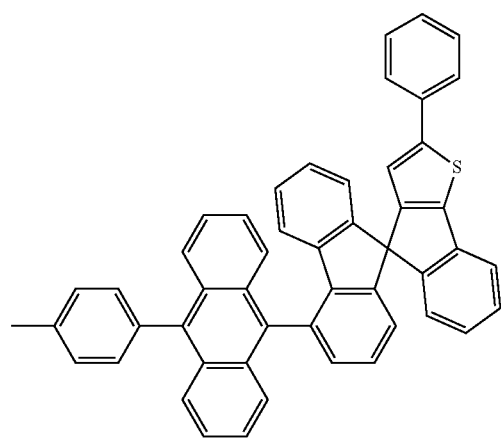
[Chemical Formula 9]
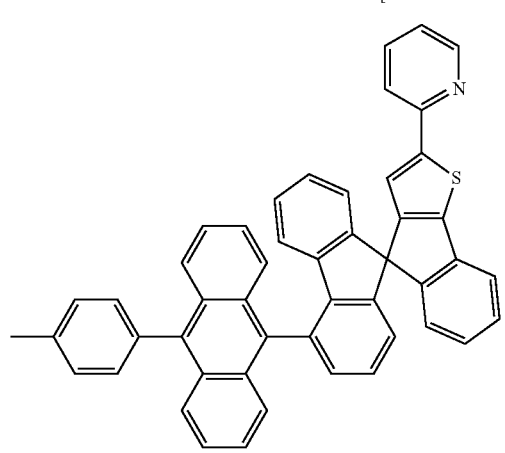
[Chemical Formula 7]
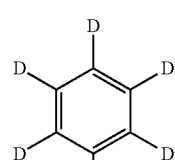
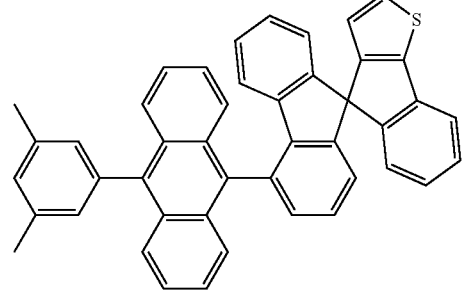
[Chemical Formula 10]
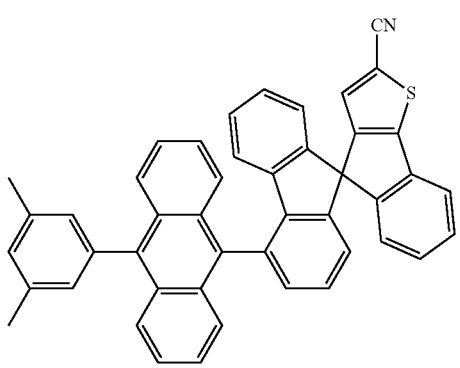
[Chemical Formula 11]
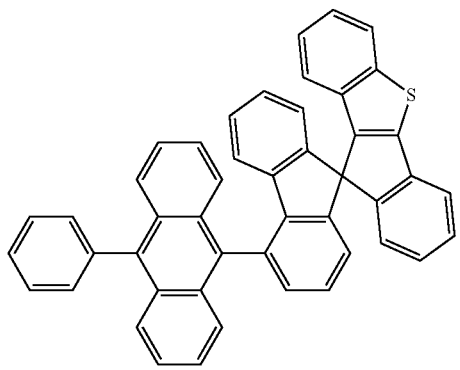
[Chemical Formula 8]
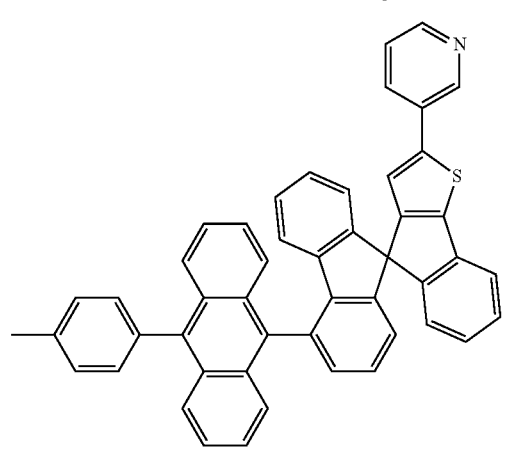
[Chemical Formula 12]
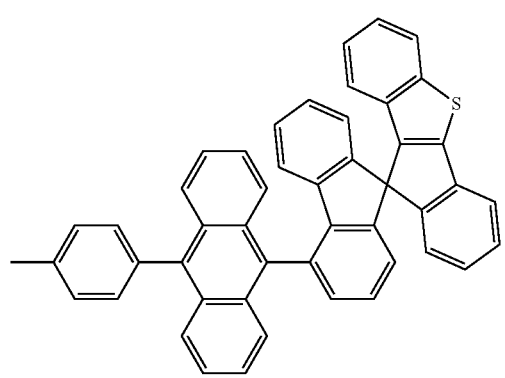

[Chemical Formula 13]
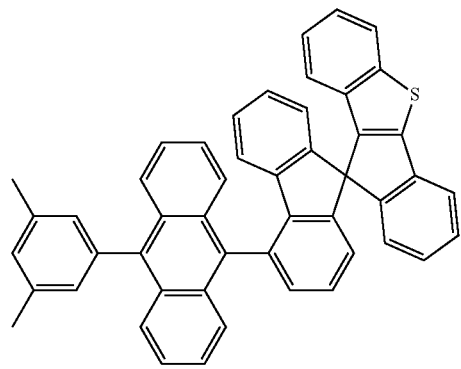
[Chemical Formula 14]
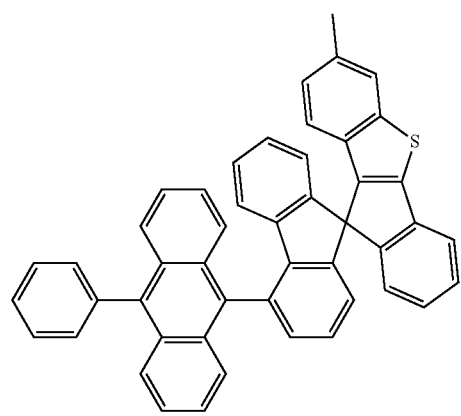
[Chemical Formula 15]
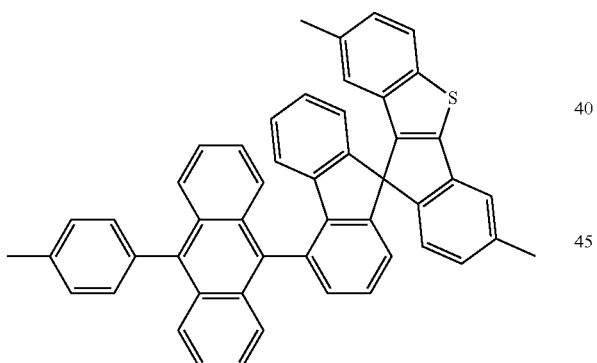
[Chemical Formula 16]
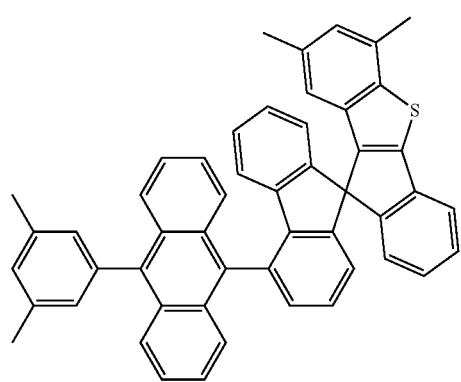
[Chemical Formula 17]
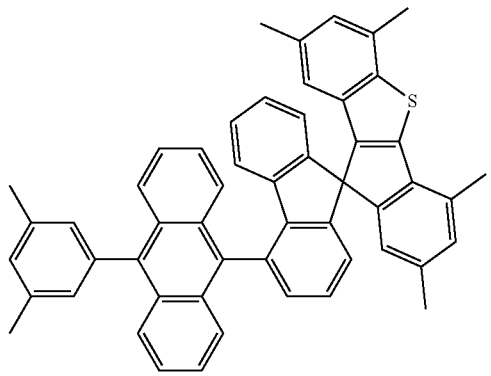
[Chemical Formula 18]
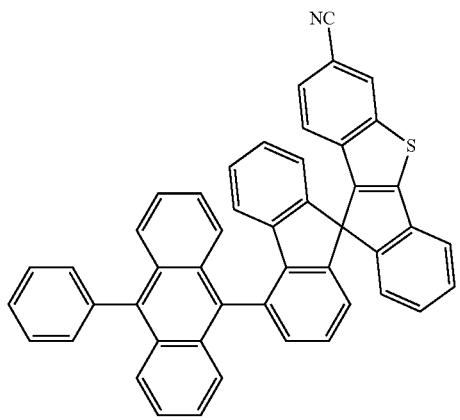
[Chemical Formula 19]
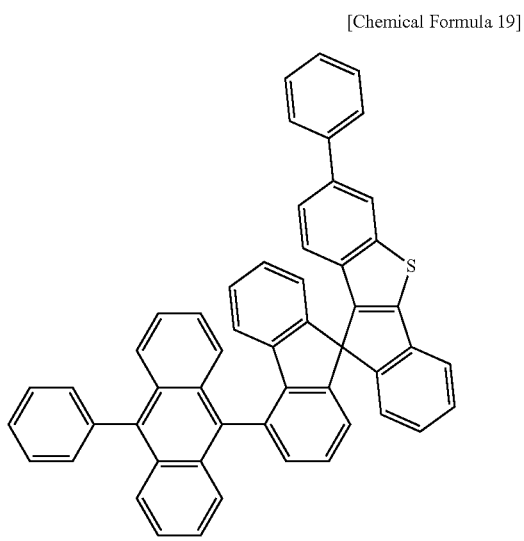

[Chemical Formula 20]
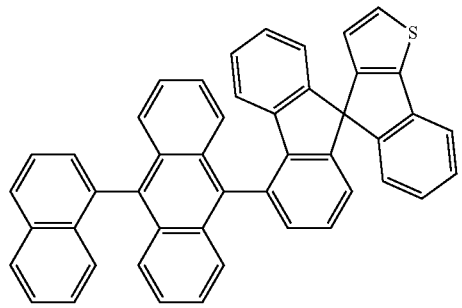
[Chemical Formula 21]
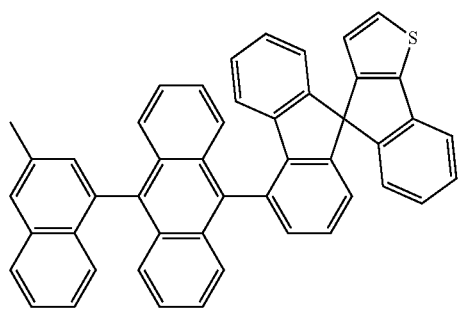
[Chemical Formula 22]
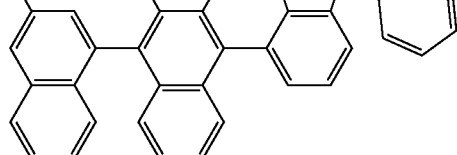
[Chemical Formula 23]
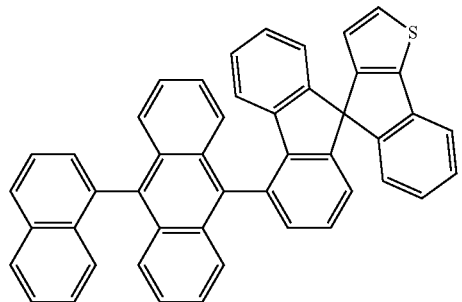
[Chemical Formula 24]
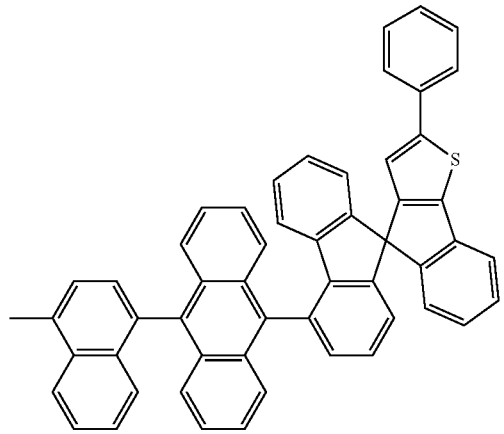
[Chemical Formula 25]
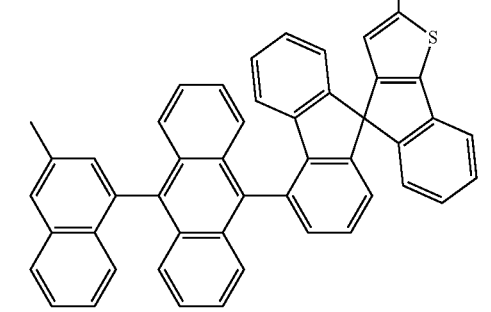
[Chemical Formula 26]
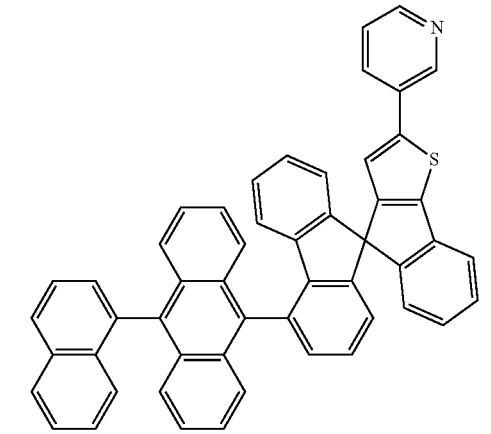

[Chemical Formula 27]
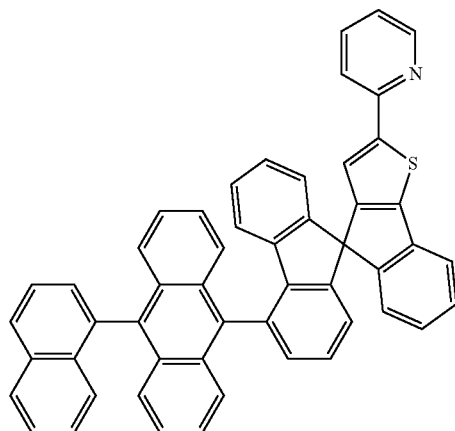
[Chemical Formula 28]
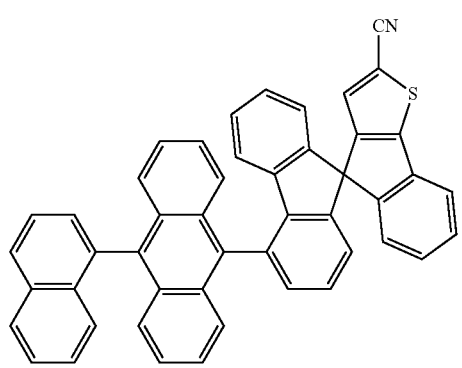
[Chemical Formula 29]
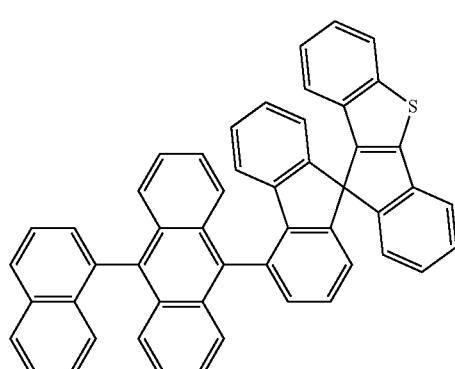
[Chemical Formula 30]
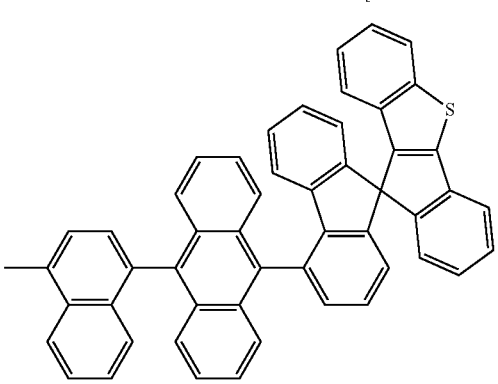
[Chemical Formula 31]
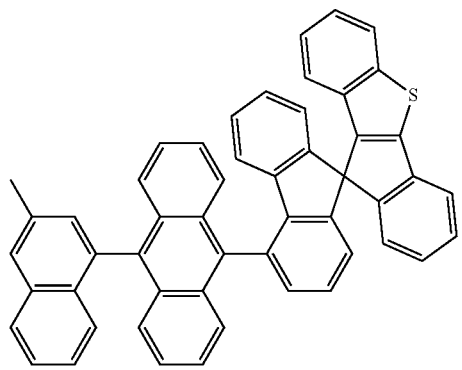
[Chemical Formula 32]
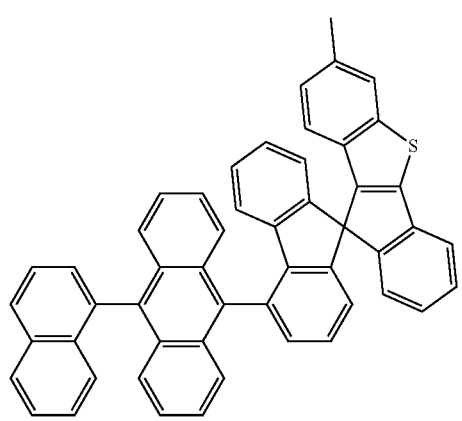
[Chemical Formula 33]
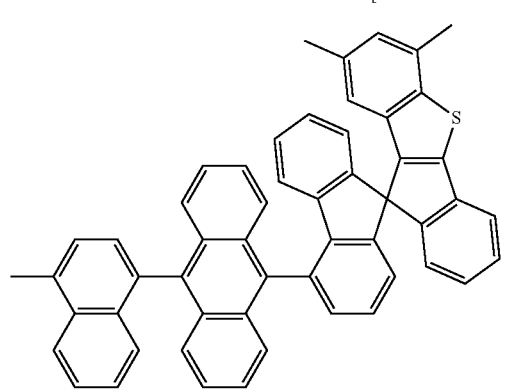
[Chemical Formula 34]
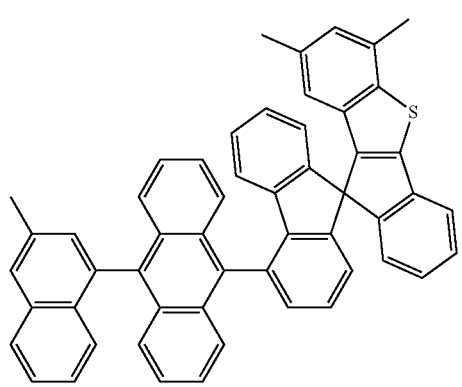

[Chemical Formula 35]
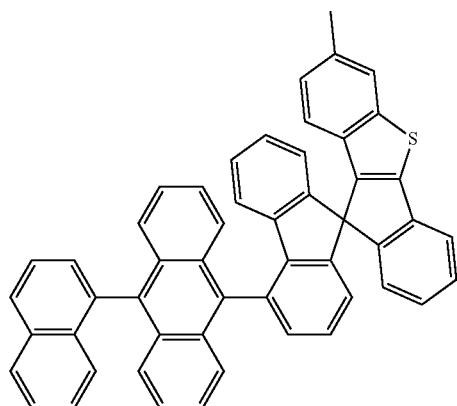
[Chemical Formula 36]
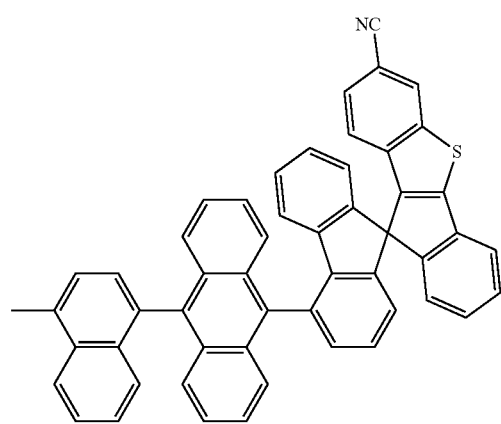
[Chemical Formula 37]
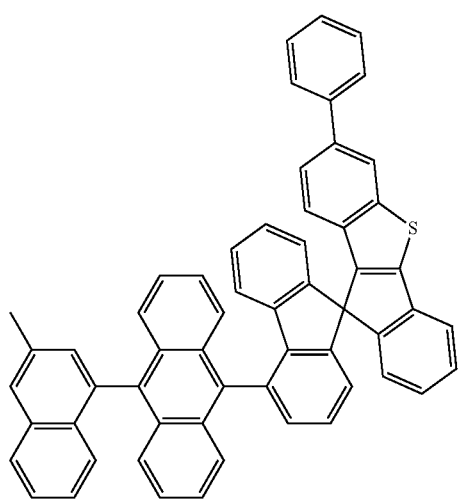
[Chemical Formula 38]
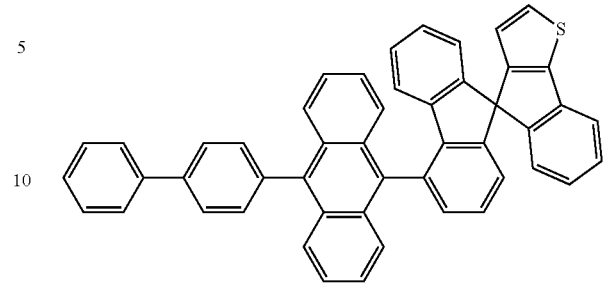
[Chemical Formula 39]
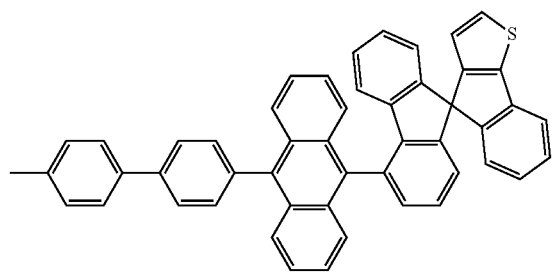
[Chemical Formula 40]
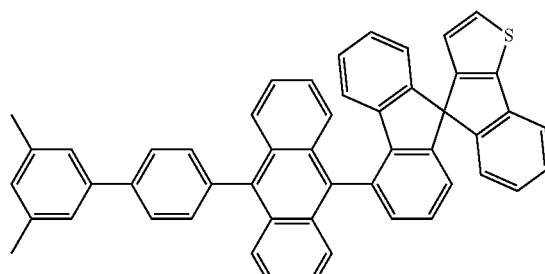
[Chemical Formula 41]
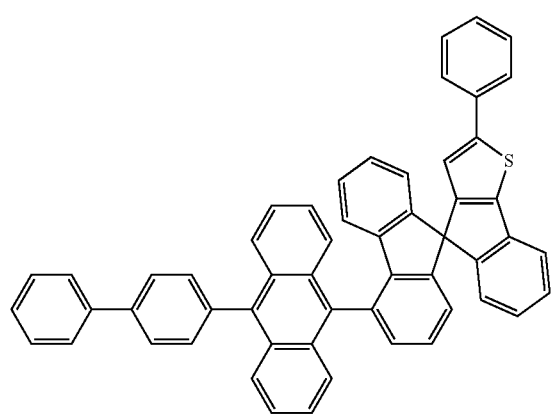

[Chemical Formula 42]
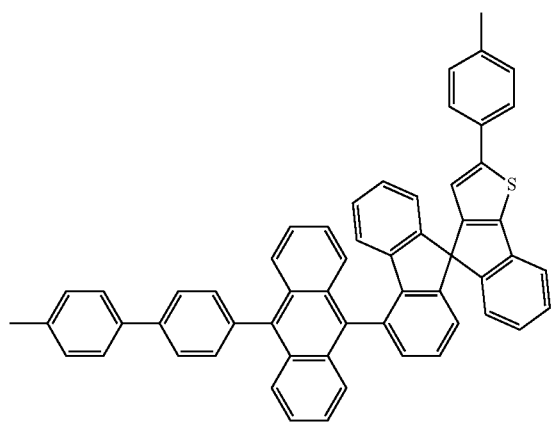
[Chemical Formula 43]
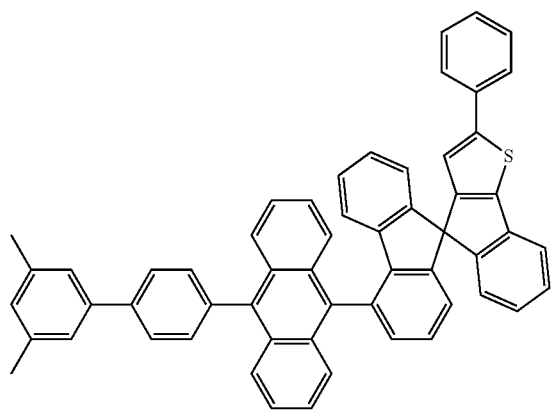
[Chemical Formula 44]
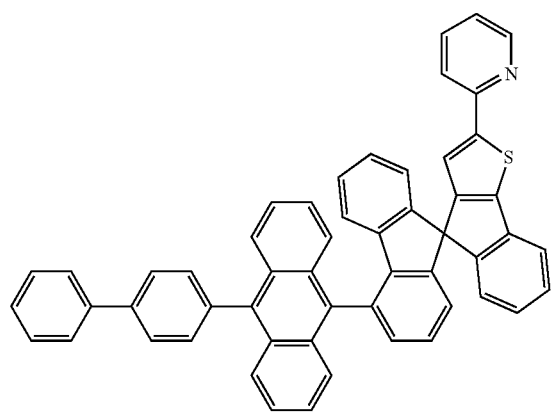
[Chemical Formula 45]
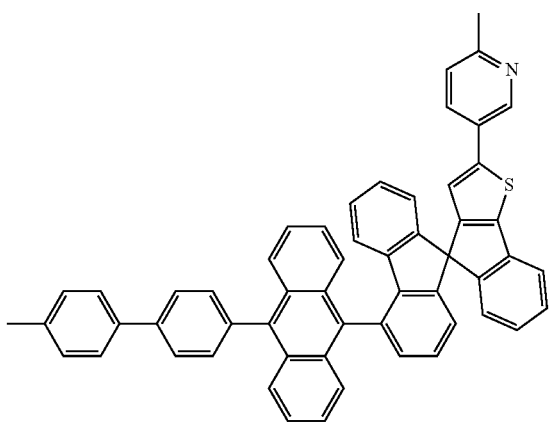
[Chemical Formula 46]
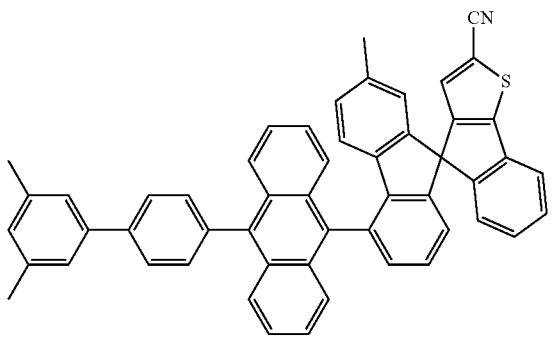
[Chemical Formula 47]
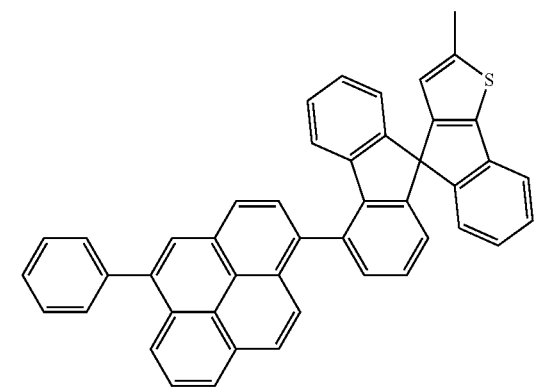
[Chemical Formula 48]
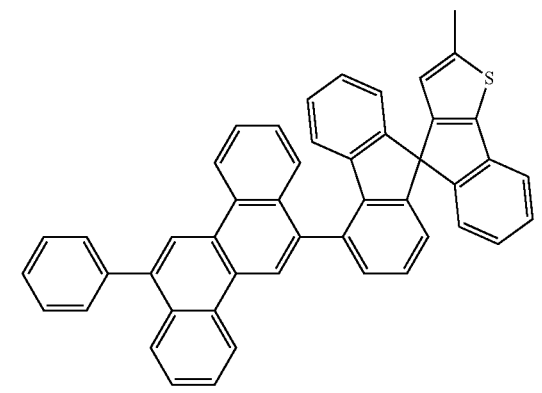

[Chemical Formula 49]
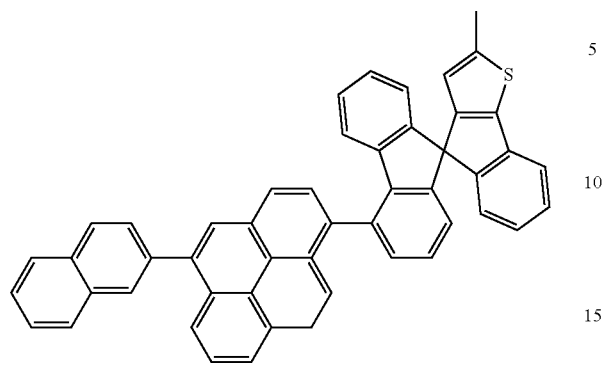
[Chemical Formula 50]
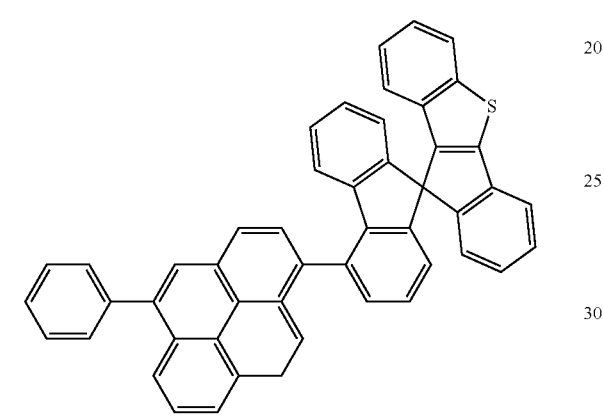
[Chemical Formula 51]
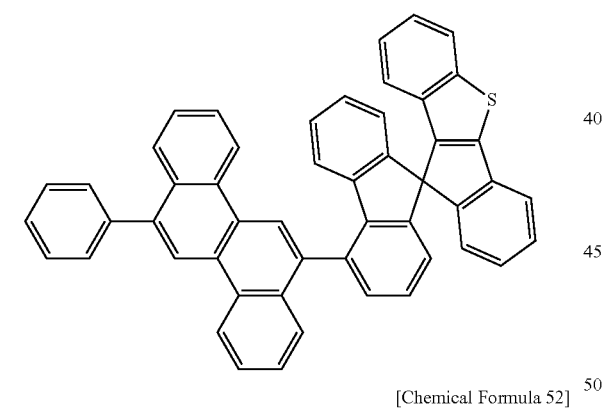
[Chemical Formula 52]
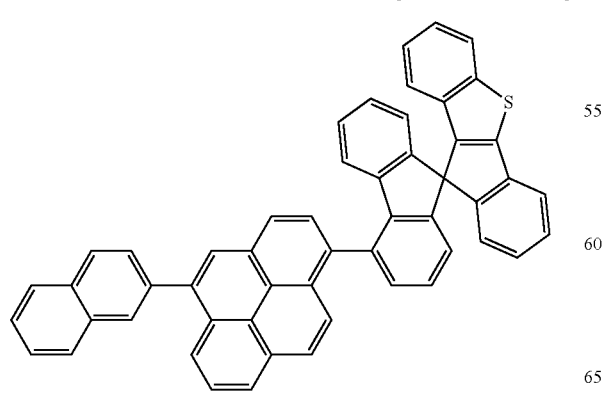
[Chemical Formula 53]
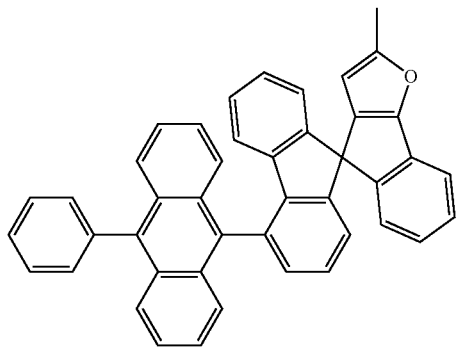
[Chemical Formula 54]
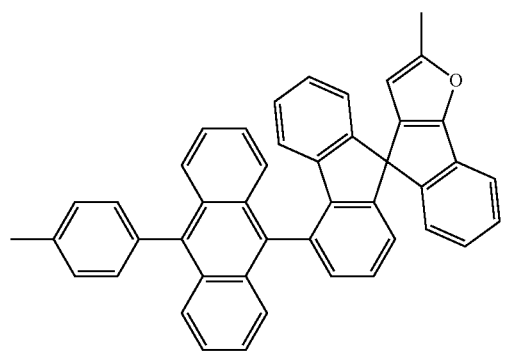
[Chemical Formula 55]
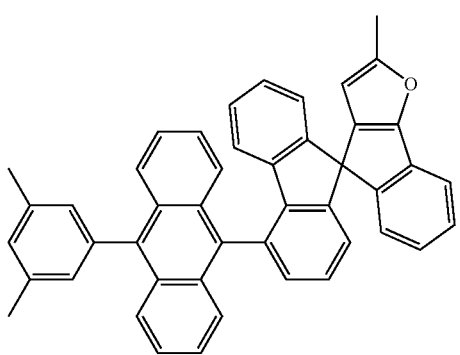
[Chemical Formula 56]
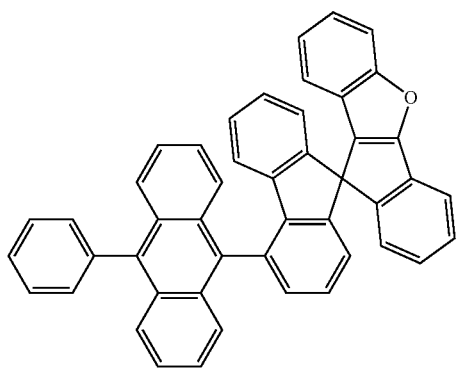

[Chemical Formula 57]
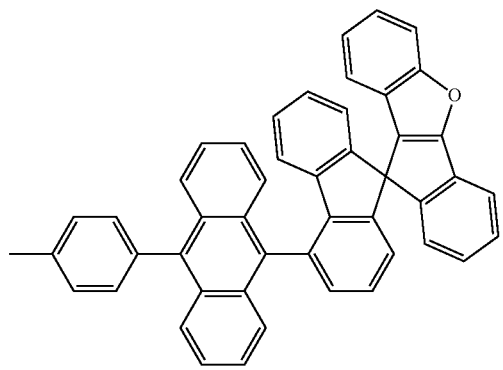
[Chemical Formula 58]
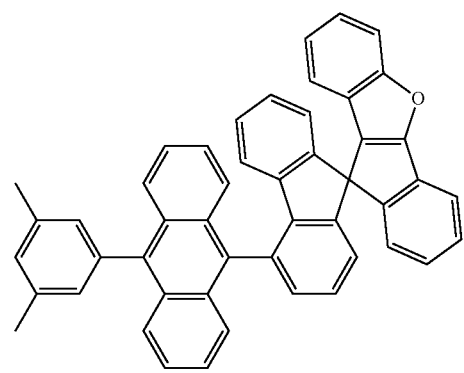
[Chemical Formula 59]
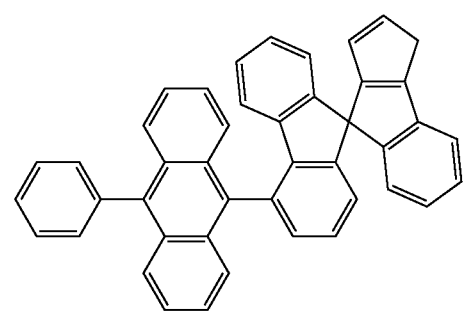
[Chemical Formula 60]
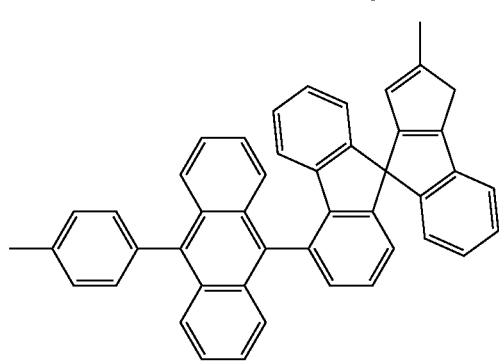
[Chemical Formula 61]
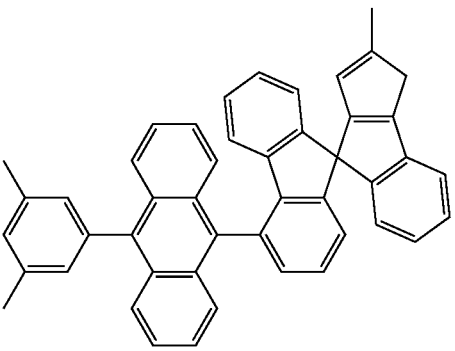
[Chemical Formula 62]
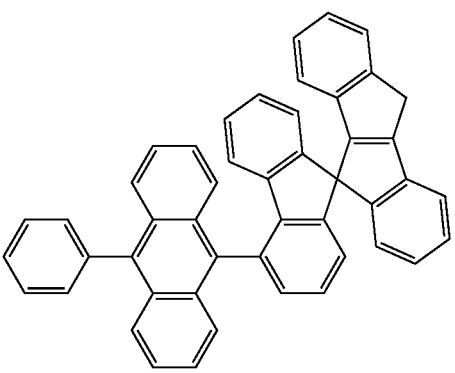
[Chemical Formula 63]
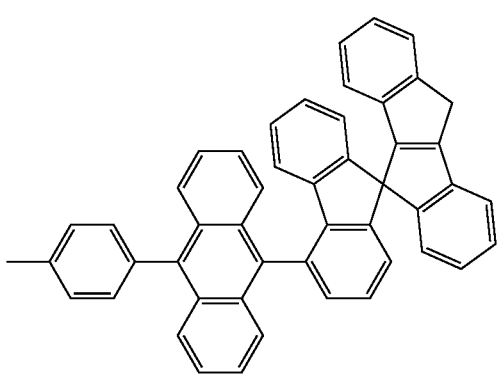
[Chemical Formula 64]
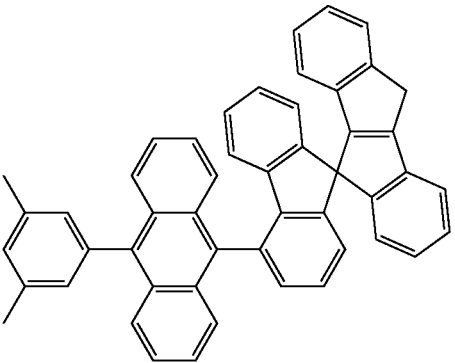

[Chemical Formula 65]

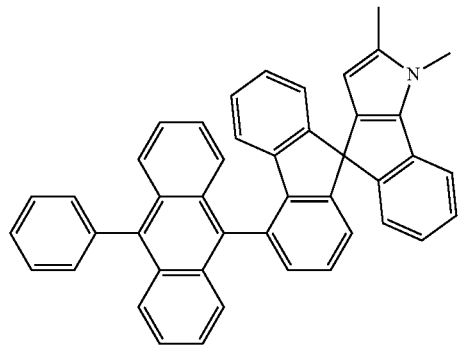

[Chemical Formula 66]

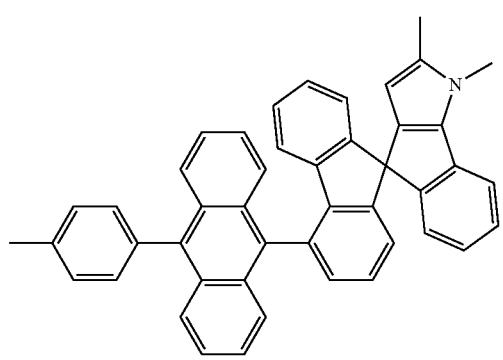

[Chemical Formula 67]

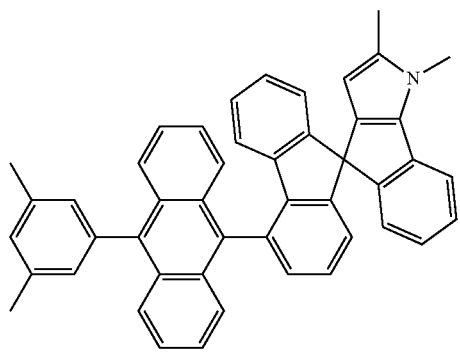

[Chemical Formula 68]

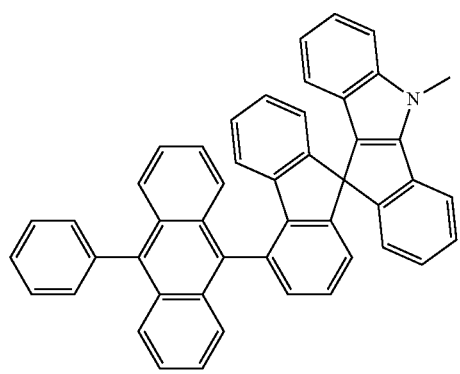

[Chemical Formula 69]

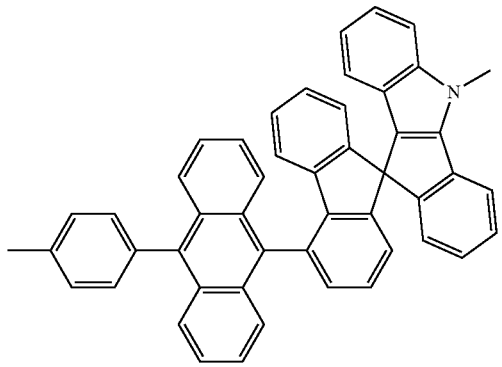

[Chemical Formula 70]

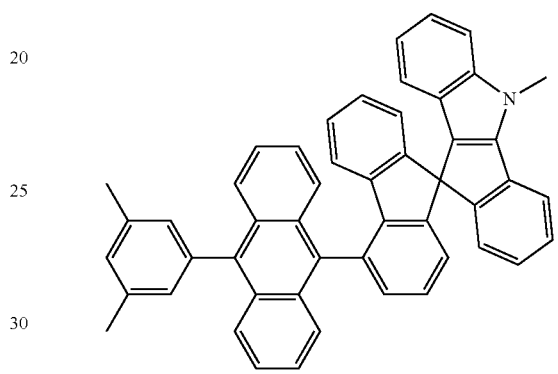

An organic emitting diode device according to an example embodiment applied with the described organic compound will be described with reference to FIG. 1.

FIG. 1 is a view of an organic emitting diode device according to an example embodiment.

Referring to FIG. 1, an organic light emitting device according to the present example embodiment includes a first electrode 100, a second electrode 300 facing the first electrode 100, and an organic layer 200 interposed between the first electrode 100 and the second electrode 300.

The substrate (not shown) may be disposed at the first electrode 100 side or the second electrode 300 side. The substrate is preferably a glass substrate or a transparent plastic substrate having excellent mechanical strength, thermal stability, transparency, surface flatness, easy handling, and water-resistance.

The first electrode 100 may be an anode, and the second electrode 300 may be a cathode. The first electrode 100 and the second electrode 300 may be transparent or non-transparent electrodes. For example, the first electrode 100 and the second electrode 300 may be a transparent electrode made of ITO (indium tin oxide), IZO (indium zinc oxide), or combinations thereof, or a non-transparent electrode made of aluminum (Al), silver (Ag), magnesium (Mg), or combinations thereof.

The organic layer 200 includes a hole injection layer (HIL) 210, a hole transport layer (HTL) 220, an assistance layer 230, an emission layer 240, and an electron transport layer (ETL) 250 sequentially disposed on the first electrode 100. Here, at least one among the hole injection layer (HIL) 210, the hole transport layer (HTL) 220, the emission layer 240, and the electron transport layer (ETL) 250 may be omitted.

The organic layer 200 may be formed by using various methods such as a vacuum deposition method, a spin coating method, a casting method, and an LB method.

When using the vacuum deposition method, the deposition conditions may vary according to the material that is used to form the organic layer 200, and the structure and thermal characteristics of the organic layer. For example, the deposition conditions may include a deposition temperature of about 100° C. to 500° C., a vacuum pressure of about 10-8 to about 10-3 torr, and a deposition speed of about 0.01 to about 100 Å/s, but is not limited thereto.

When using the spin coating method, the coating conditions may vary according to the material used to form the organic layer 200, and the structure and thermal characteristics of the organic layer. For example, the coating conditions may include a coating speed of about 2000 rpm to about 5000 rpm, and a thermal treatment temperature of about 80° C. to about 200° C. at which the solvent remaining after coating may be removed, but is not limited thereto.

The emission layer 230 may include the compound represented by Chemical Formula 1. The compound represented by Chemical Formula 1 may be used as a host or a dopant.

When using the compound represented by Chemical Formula 1, the disclosed material may be included. The disclosed host material may be Alq3, CBP (4,4'-N,N'-dicarbazole-biphenyl), PVK (poly(n-vinylcarbazole)), 9,10-di(naphtalene-2-yl)anthracene (ADN), TCTA, TPBI (1,3,5-tris(N-phenylbenzimidazole-2-yl)benzene)), TBADN (3-tert-butyl-9,10-di(napht-2-yl)anthracene), E3, or DSA (distyryl arylene), but is not limited thereto.

When using the compound represented by Chemical Formula 1, it may be used singularly or the mixture thereof may be included, and another organic material may be mixed to be included. When the compound represented by the Chemical Formula 1 is included in the other organic material, the compound may serve as a fluorescent host or a phosphorescent host, and the disclosed dopant may be included.

As the disclosed red dopant, PtOEP, Ir(piq)$_3$, Btp$_2$Ir(acac), or DCJTB may be used, but is not limited thereto.

As the disclosed green dopant, Ir(ppy)$_3$ (ppy=phenylpyridine), Ir(ppy)$_2$(acac), Ir(mpyp)$_3$, or C545T may be used, but is not limited thereto.

As the disclosed blue dopant, F$_2$Irpic, (F$_2$ppy)$_2$Ir(tmd), Ir(dfppz)$_3$, terfluorene, 4,4'-bis(4-diphenylaminostyryl)biphenyl (DPAVBi), or 2,5,8,11-tetra-tert-butyl perylene (TBP) may be used, but is not limited thereto.

The content of the dopant may be selected in a range of 0.1 to 20 wt %, particularly 0.5-12 wt %, based on 100 wt % of an emission layer forming material (for example, a total weight if the host and the dopant is determined as 100 wt %), but it is not limited thereto.

The thickness of the emission layer 230 may be 100 Å to 1000 Å, preferably 200 Å to 600 Å.

Also, the emission layer 230 may further include an anthracene compound, an arylamine compound, a styryl compound, derivatives thereof, or combinations thereof as well as the compound represented by Chemical Formula 1.

At least one hydrogen atom among the anthracene compound, the arylamine compound, or the styryl compound may be substituted by the same substitution group as the substitution group of the described C1 to C30 alkyl groups. The arylamine as the C5 to C30 arylamine group may include the amino group that is substituted into the C6 to C30 aryl group or the C2 to C30 heteroaryl group.

The emission layer 230 may emit white light by a combination of the primary colors such as three primary colors of red, green, and blue, and the white light may be emitted by combining the colors of the adjacent subpixels or by combining the colors that are deposited in the vertical direction.

The hole injection layer 210 and the hole transfer layer 220 serve to easily transmit the holes from the first electrode 100 to the emission layer 230.

The hole injection layer 210 may include the compound represented by Chemical Formula 1.

Also, the hole injection layer 210 may include a disclosed hole injection material. For example, the disclosed hole injection material may be a phthalocyanine compound such as copper phthalocyanine or the like, m-MTDATA (4,4',4''-tris(3-methylphenylphenylamino)triphenylamine), NPB (N,N'-di(1-naphthyl)-N,N'-diphenylbenzidine(N,N'-di(1-naphthyl)-N,N'-diphenylbenzidine)), TDATA, 2T-NATA, PANI/DBSA (polyaniline/dodecylbenzene sulfonic acid: polyaniline/dodecylbenzene sulfonic acid), PEDOT/PSS (poly(3,4-ethylene dioxythiophene)/poly(4-styrene sulfonate):poly(3,4-ethylene dioxythiophene)/poly(4-styrene sulfonate)), PANI/CSA (polyaniline/camphor sulfonic acid: polyaniline/camphor sulfonic acid), or PANI/PSS (((polyaniline)/poly(4-styrene sulfonate):polyaniline)/poly(4-styrene sulfonate)), but is not limited thereto.

The thickness of the hole injection layer 210 may be 100 Å to 10,000 Å, preferably 100 Å to 1000 Å.

The hole transfer layer 220 may include the compound represented by Chemical Formula 1.

Also, the hole transfer layer 220 may include a disclosed hole transfer material. For example, the hole transport material may be a carbazole derivative such as N-phenylcarbazole, polyvinylcarbazole, or the like, and an amine derivative having an aromatic condensed ring such as NPB, N,N'-bis(3-methylphenyl)-N,N'-diphenyl-[1,1-biphenyl]-4, 4'-diamine (TPD), tris(4-carbazoyl-9-ylphenyl)amine (TCTA), or the like. In a case of containing TCTA, the hole transport layer 30 serves to perform not only a hole transport operation but also an operation for preventing diffusion of excitons from the emission layer.

The thickness of the hole transfer layer 220 may be 50 Å to 1000 Å, preferably 100 Å to 600 Å.

The hole injection layer 210 or the hole transfer layer 220 may further contain a charge-generation material to improve film conductivity and the like.

For example, the charge-generation material may be a p-dopant. A non-limited example of the p-dopant may include a quinone derivative such as tetracyanoquinodimethane (TCNQ) and 2,3,5,6-tetrafluoro-tetracyano-1,4-benzoquinonedimethane (F4TCNQ) or the like; a metal oxide such as tungsten oxide and molybdenum oxide; and a cyano group-containing compound such as the compound represented by Chemical Formula 71, but is not limited thereto.

[Chemical Formula 71]

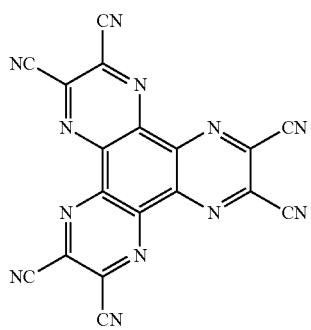

When the hole injection layer 210 or the hole transfer layer 220 further contains the charge-generation material, the charge-generation material may be subject to numerous variations, e.g., non-uniformly distributed or uniformly dispersed over the hole injection layer 210 and the hole transfer layer 220.

The electron transfer layer 240 and the electron injection layer 250 serve to easily inject the electron from the second electrode 300 to the emission layer 230.

The electron transfer layer 240 may include the compound represented by Chemical Formula 1.

Also, the electron transfer layer 240 may include the disclosed electron transfer material. The electron transfer layer 240 may use quinoline derivatives, particularly, aluminum tris(8-hydroxyquinoline) (Alq3), TAZ, or Balq, but is not limited thereto.

Also, the electron transfer layer 240 may include an electron transfer organic compound and a metal containing material. Non-limiting examples of the electron transfer layer may be 9,10-di(naphtalene-2-yl)anthracene (ADN) and an anthracene-based compound such as compounds represented by Chemical Formula 72 and Chemical Formula 73 below, but it is not restrictive.

[Chemical Formula 72]

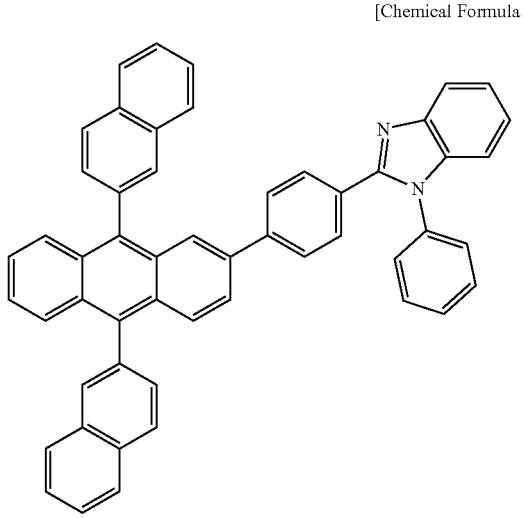

[Chemical Formula 73]

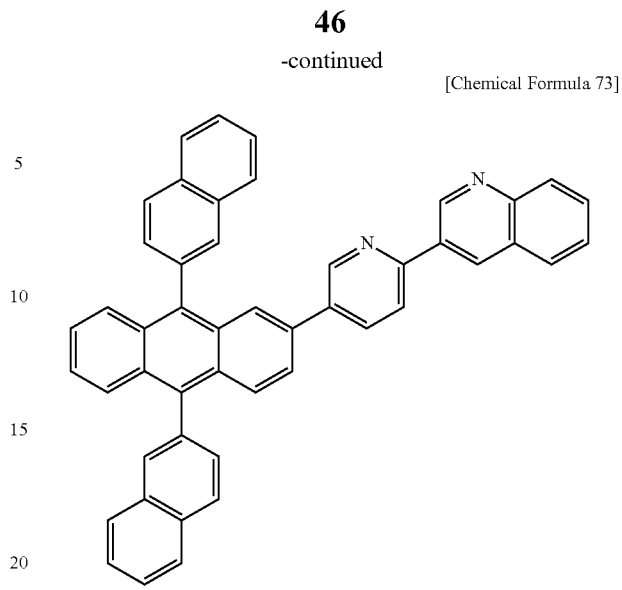

The metal containing material may include a lithium (Li) complex, and a non-limited example of the lithium complex may be lithium quinolate (Liq) and a compound represented by Chemical Formula 74, but is not limited thereto.

[Chemical Formula 74]

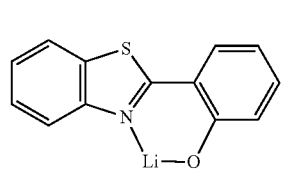

The thickness of the electron transfer layer may be about 100 Å to 1000 Å, preferably 100 Å to 500 Å.

The electron injection layer 250 may include the compound represented by Chemical Formula 1.

Also, the electron injection layer 250 may include a disclosed electron transfer material. For example, the disclosed material as a material forming the electron injection layer such as LiF, NaCl, CsF, Li2O, BaO may be used, but is not limited thereto.

The thickness of the electron injection layer 250 may be about 1 Å to 100 Å, preferably 5 Å to 90 Å.

When the emission layer 230 contains a phosphorescent dopant, a hole blocking layer (not shown) may be formed between the emission layer 230 and the electron transfer layer 240 to prevent the diffusion of triplet excitons or holes into the ETL.

In this case, the material forming the hole blocking material employed herein is not particularly limited. One of well-known hole blocking materials may be freely selected and used. An example of the hole blocking material may include an oxadiazole derivative, a triazole derivative, a phenanthroline derivative, Balq, BCP, and the like.

The thickness of the hole blocking layer may be about 50 Å to 1000 Å, preferably 100 Å to 300 Å.

The organic emitting diode device according to the present example embodiment may be formed of various structures.

For example, the organic emitting diode device according to the present example embodiment may be formed of a structure of the first electrode/the hole injection layer/the emission layer/the second electrode, the first electrode/the hole injection layer/the hole transfer layer/the emission layer/the electron transfer layer/the second electrode, or the first electrode/the hole injection layer/the hole transfer layer/the emission layer/the electron transfer layer/the electron injection layer/the second electrode.

Also, the organic emitting diode device according to the present example embodiment may be made of a structure of the first electrode/a functional layer simultaneously having the hole injection function and the hole transfer function/the emission layer/the electron transfer layer/the second electrode, or the first electrode/the functional layer simultaneously having the hole injection function and the hole transfer function/the emission layer/the electron transfer layer/the electron injection layer/the second electrode.

Further, the organic emitting diode device according to the present example embodiment may be made of a structure of the first electrode/the hole transfer layer/the emission layer/the functional layer simultaneously having the electron injection function and the electron transfer function/the second electrode, the first electrode/the hole injection layer/the emission layer/the functional layer simultaneously having the electron injection function and the electron transfer function/the second electrode, or the first electrode/the hole injection layer/the hole transfer layer/the emission layer/the functional layer simultaneously having the electron injection and the electron transfer function/the second electrode.

The organic emitting diode device according to an example embodiment may be provided to the passive matrix organic light emitting device and the active matrix organic light emitting device. Particularly, when providing the active matrix organic light emitting device, the first electrode provided to the substrate as the pixel electrode may be electrically connected to the source electrode or the drain electrode of the thin film transistor.

Also, the organic emitting diode device according to an example embodiment may be provided to a flat panel display displaying the image through both surfaces.

Further, the organic layer of the organic emitting diode device according to an example embodiment may be formed by a wetting method coating the compound represented by Chemical Formula 1 manufactured of a solution.

Hereinafter, the present embodiments will be described in detail through a composition example and an example embodiment. However, the following examples are set forth for the purpose of the description, but are not to be construed to limit the scope of the present embodiments.

COMPOSITION EXAMPLE

Composition Example 1. A Composition of the Compound Represented by Chemical Formula 5

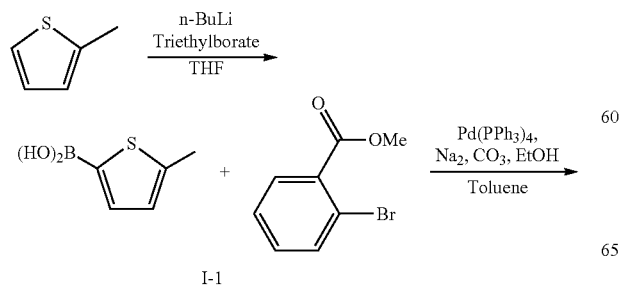

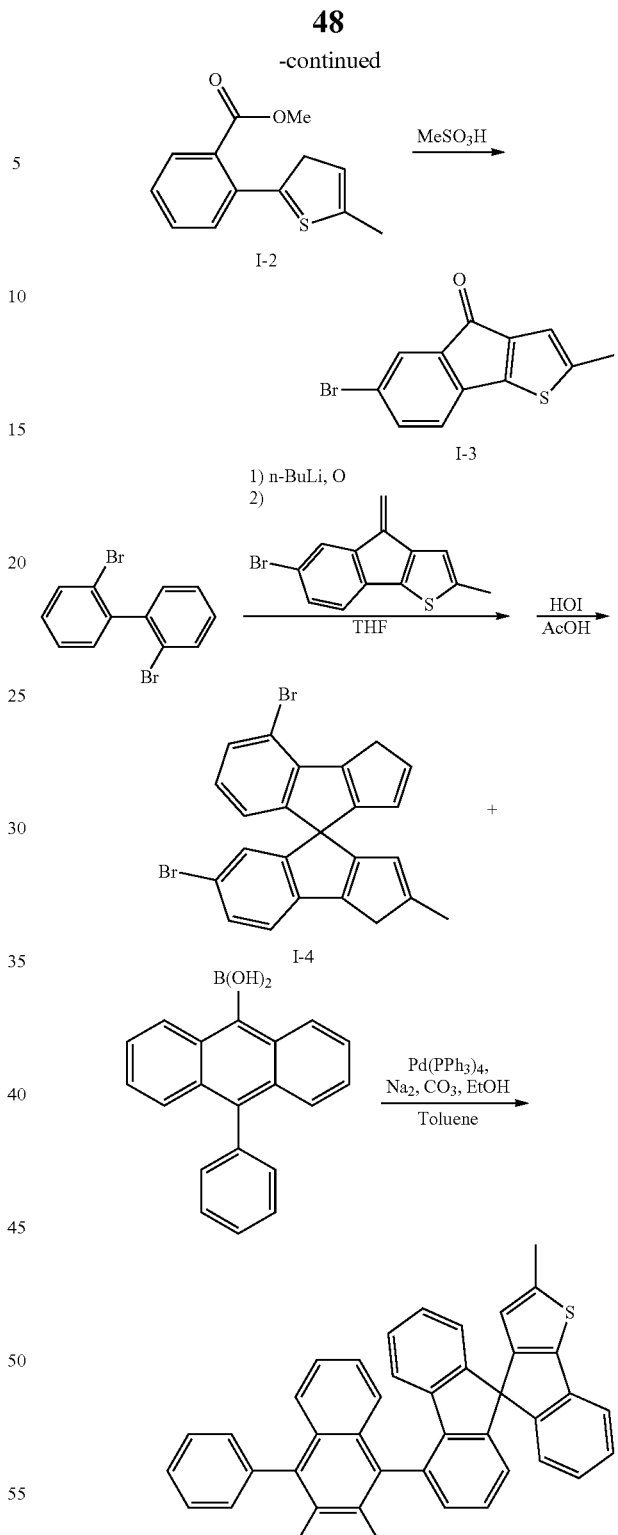

An intermediate I-1 at 3.2 g (22.5 mmol) is formed by adding 2-(methylthiophene) at 3.6 g (30.6 mmol) to n-BuLi at 3 ml and adding triethyl borate at 1.2 equivalents, and is synthesized with 5-bromo-2-iodo-benzoic acid methyl ester at 1.1 equivalents through Suzuki coupling to form an intermediate I-2, and an intermediate I-3 at 2.7 g (9.2 mmol) is synthesized through cyclization.

2,2'-dibromobiphenyl at 3 g is added to n-BuLi at 3 ml and the above manufactured intermediate I-3 at 2.7 g, and hydrochloric acid at 6 ml is added to compose an intermediate I-4 at 3.4 g (6.87 mmol).

A compound (4.3 g, 70% yield) represented by Chemical Formula 5 is obtained through Suzuki coupling of the intermediate I-4 and 9-phenyl anthracene boronic acid.

Composition Example 2. A Composition of the Compound Represented by Chemical Formula 23

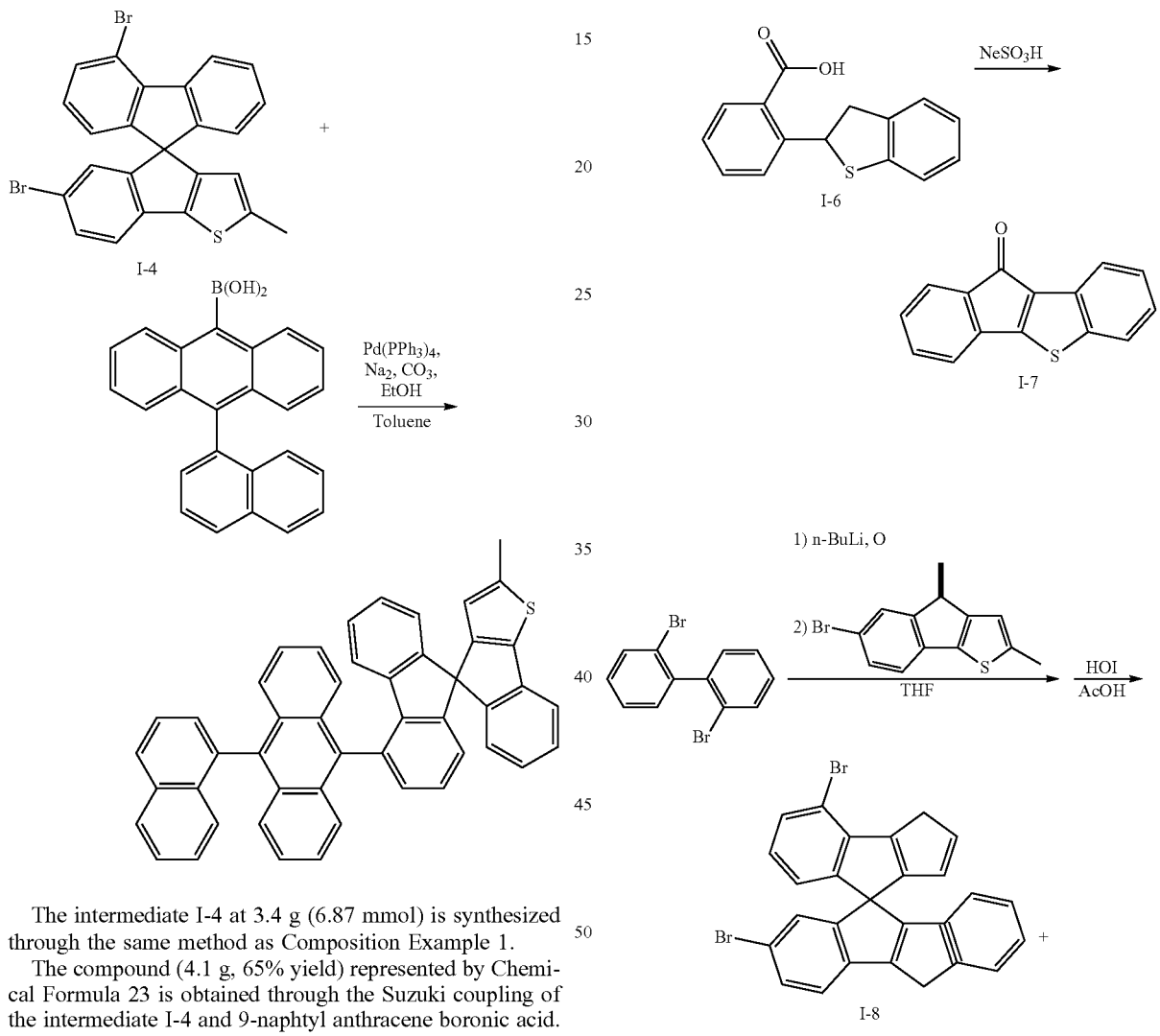

The intermediate I-4 at 3.4 g (6.87 mmol) is synthesized through the same method as Composition Example 1.

The compound (4.1 g, 65% yield) represented by Chemical Formula 23 is obtained through the Suzuki coupling of the intermediate I-4 and 9-naphtyl anthracene boronic acid.

Composition Example 3. A Composition of the Compound Represented by Chemical Formula 11

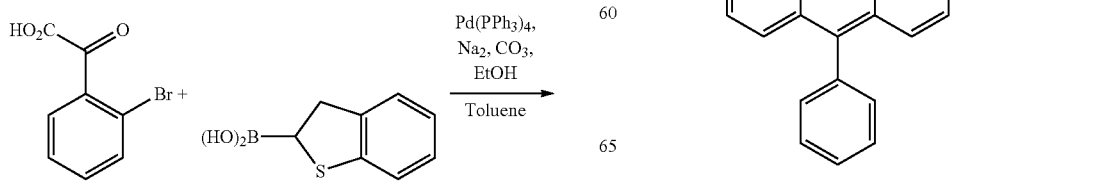

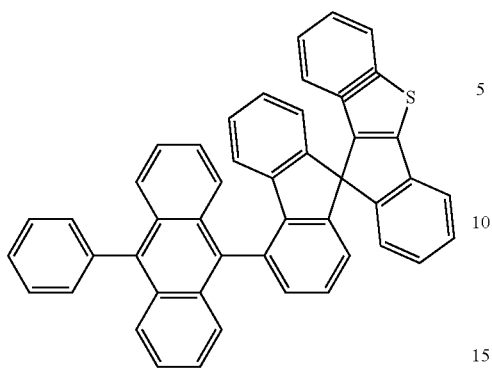

5-bromo-2-iodo-benzoic acid methyl ester at 4 g (18 mmol) and benzothiophene boronic acid at 1.1 equivalents are synthesized through the Suzuki coupling to form an intermediate I-5, an intermediate I-6 is made through a NaOH Sn2 substitution reaction, and an intermediate I-7 at 2.7 g (8.56 mmol) is synthesized by cyclization of the intermediate I-6.

2,2'-dibromobiphenyl at 3 g is added to the produced intermediate I-7 at 2.7 g along with the n-BuLi at 3 ml, and hydrochloric acid at 6 ml is added to compose an intermediate I-8 at 3.7 g (6.99 mmol).

The compound (3.6 g, 75% yield) represented by Chemical Formula 11 is obtained through the Suzuki coupling of the intermediate I-8 and 9-phenyl anthracene boronic acid.

Composition Example 4. A Composition of the Compound Represented by Chemical Formula 29

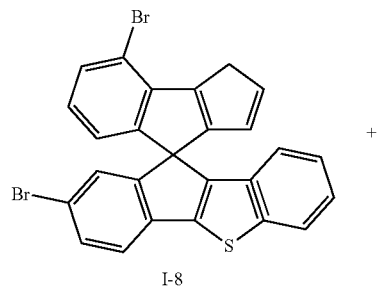

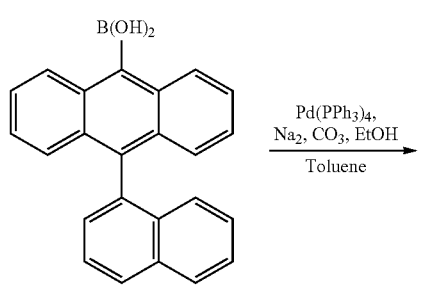

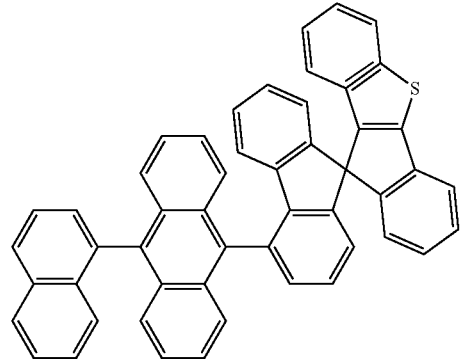

An intermediate I-8 at 3.6 g (6.8 mmol) is synthesized through the same method as Composition Example 3.

The compound (3.1 g, 60% yield) represented by Chemical Formula 29 is obtained through the Suzuki coupling of the intermediate I-8 and 9-naphtyl anthracene boronic acid.

EXAMPLE EMBODIMENTS AND COMPARATIVE EXAMPLES

Example Embodiment 1

As the anode, a 15 Ω/cm² 1200 Å ITO glass substrate from Corning is cut to dimensions of 50 mm×50 mm×0.7 mm and is subjected to ultrasonic wave cleaning for 5 min by using isopropyl alcohol and pure water and is irradiated with ultraviolet rays for 30 min, and then the glass substrate is exposed to ozone to be cleaned for 10 min and is installed in a vacuum deposition apparatus.

The hole injection layer with a thickness of 600 Å is formed by vacuum-depositing 2-TNATA (4,4',4"-tris(N-(2-naphthyl)-N-phenyl-amino)-triphenylamine) on the ITO layer. The hole transfer layer with a thickness of 300 Å is formed by vacuum depositing NPB (N,N'-bis(naphthalen-1-yl)-N,N'-bis(phenyl)-benzidine) on the hole injection layer.

The compound (the host) represented by Chemical Formula 5 and $F_2$irpic (the dopant) at a 95:5 weight ratio are vacuum deposited on the hole transfer layer to form the emission layer with a 200 Å thickness.

The compound represented by Chemical Formula 72 is vacuum deposited on the emission layer to form the electron transfer layer with a 300 Å thickness, the LiF is vacuum deposited on the electron transfer layer to form the electron injection layer with a 10 Å thickness, and the Al is vacuum deposited on the electron injection layer to form the cathode with a 3000 Å thickness, thereby manufacturing the organic light emitting element.

This element has a driving voltage of 3.8 V, emission luminance of 413 cd/m², and emission efficiency of 4.01 cd/A at a current density of 10 mA/cm².

Example Embodiment 2

The organic light emitting element is manufactured by the same method as Example Embodiment 1, except for using the compound represented by Chemical Formula 23 instead of the compound represented by Chemical Formula 5 as the host.

This element has a driving voltage of 3.9 V, emission luminance of 394 cd/m², and emission efficiency of 3.79 cd/A at a current density of 10 mA/cm².

Example Embodiment 3

The organic light emitting element is manufactured by the same method as Example Embodiment 1, except for using the compound represented by Chemical Formula 11 instead of the compound represented by Chemical Formula 5 as the host.

This element has a driving voltage of 3.8 V, emission luminance of 425 cd/m$^2$, and emission efficiency of 4.53 cd/A at a current density of 10 mA/cm$^2$.

Example Embodiment 4

The organic light emitting element is manufactured by the same method as Example Embodiment 1, except for using the compound represented by Chemical Formula 29 instead of the compound represented by Chemical Formula 5 as the host.

This element has a driving voltage of 3.7 V, emission luminance of 381 cd/m$^2$, and emission efficiency of 3.64 cd/A at a current density of 10 mA/cm$^2$.

Comparative Example 1

The organic light emitting element is manufactured by the same method as Example Embodiment 1, except for using the 9,10-di(naphth-2-yl)anthracene) (ADN) as the host when forming the emission layer instead of the compound represented by Chemical Formula 5.

This element has a driving voltage of 4.2 V, emission luminance of 328 cd/m$^2$, and emission efficiency of 3.10 cd/A at a current density of 10 mA/cm$^2$.

Comparative Example 2

The organic light emitting element is manufactured by the same method as the example embodiment 1, except for using a compound represented by Chemical Formula 75 as the host when forming the emission layer instead of the compound represented by Chemical Formula 5.

This element has a driving voltage of 4.4 V, emission luminance of 346 cd/m$^2$, and emission efficiency of 3.31 cd/A at a current density of 10 mA/cm$^2$.

[Chemical Formula 75]

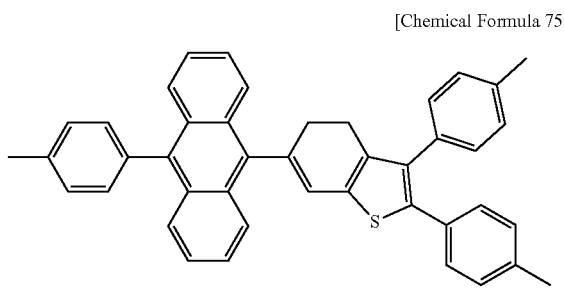

Comparative Example 3

The organic light emitting element is manufactured by the same method as Example Embodiment 1, except for using a compound represented by Chemical Formula 76 as the host when forming the emission layer instead of the compound represented by Chemical Formula 5.

This element has a driving voltage of 4.5 V, emission luminance of 350 cd/m$^2$, and emission efficiency of 3.27 cd/A at a current density of 10 mA/cm$^2$.

[Chemical Formula 76]

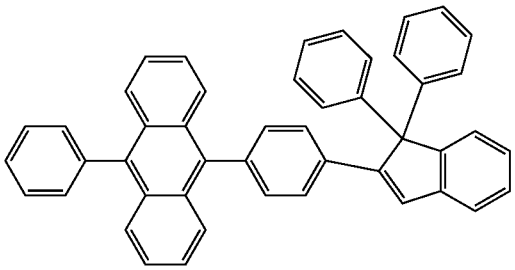

Estimation Example

The driving voltage, the luminance, and the efficiency of the organic light emitting element manufactured in Example Embodiments 1 to 4 and Comparative Examples 1 to 3 are estimated by supplying power in a current voltage system (Keithley SMU 236) and using a luminance system PR650 Spectroscan Source Measurement Unit (Photo Research Inc.). The results thereof are shown in Table 1

TABLE 1

| | Host | Dopant | Driving voltage (V) | Luminance (cd/m$^2$) | Efficiency (cd/A) |
|---|---|---|---|---|---|
| Example Embodiment 1 | Chemical Formula 5 | F$_2$irpic | 3.8 | 413 | 4.01 |
| Example Embodiment 2 | Chemical Formula 23 | F$_2$irpic | 3.9 | 394 | 3.79 |
| Example Embodiment 3 | Chemical Formula 11 | F$_2$irpic | 3.8 | 425 | 4.53 |
| Example embodiment 4 | Chemical Formula 29 | F$_2$irpic | 3.7 | 381 | 3.64 |
| Comparative Example 1 | ADN | F$_2$irpic | 4.2 | 328 | 3.10 |
| Comparative Example 2 | Chemical Formula 75 | F$_2$irpic | 4.4 | 346 | 3.31 |
| Comparative Example 3 | Chemical Formula 76 | F$_2$irpic | 4.5 | 350 | 3.27 |

Referring to Table 1, the organic light emitting element of Example Embodiments 1 to 4 has a lower driving voltage and excellent luminance and efficiency characteristics compared with the organic light emitting element of Comparative Examples 1 to 3.

While these embodiments have been described in connection with what is presently considered to be practical example embodiments, it is to be understood that the present embodiments are not limited to the disclosed embodiments, but, on the contrary, is intended to cover various modifications and equivalent arrangements included within the spirit and scope of the appended claims.

What is claimed is:

1. An organic compound of Chemical Formula 1:

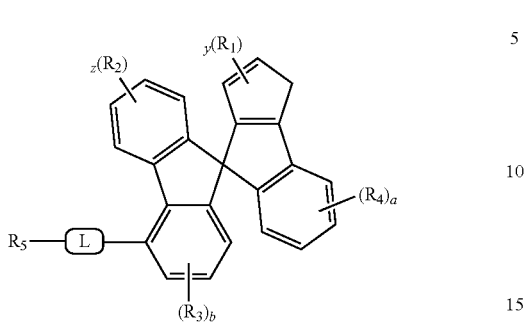

wherein $R_1$ to $R_4$ are each a hydrogen atom, a heavy hydrogen, a C1 to C60 substituted or non-substituted alkyl group, a C2 to C60 substituted or non-substituted alkenyl group, a C2 to C60 substituted or non-substituted alkynyl group, a C3 to C60 substituted or non-substituted cycloalkyl group, a C1 to C60 substituted or non-substituted alkoxy group, a C5 to C60 substituted or non-substituted aryloxy group, a C5 to C60 substituted or non-substituted arylthio group, a C5 to C60 substituted or non-substituted aryl group, an amino group substituted into a C3 to C60 heteroaryl group, a C3 to C60 substituted or non-substituted heteroaryl group, a C6 to C60 substituted or non-substituted condensation polycyclic group, a halogen atom, a cyano group, a nitro group, a hydroxyl group, or a carboxyl group, $R_1$ and $R_2$ are the same or different from each other, X is —S—, —O—, —C($R_6$)($R_7$)—, or —N($R_6$)—, $R_6$ and $R_7$ are independently a hydrogen atom, a heavy hydrogen, a C1 to C20 substituted or non-substituted alkyl group, a C5 to C20 substituted or non-substituted aryl group, a C3 to C20 substituted or non-substituted hetero aryl group, a C6 to C20 substituted or non-substituted condensation polycyclic group, a halogen atom, a cyano group, a nitro group, a hydroxyl group, or a carboxyl group, a and z are each an integer of 0 to 4, b is an integer of 0 to 3, and y is an integer of 0 to 2, L is a divalent linking group represented by —(Ar$_1$)$_n$—, wherein Ar$_1$ is a C5 to C60 substituted or non-substituted arylene group, a C3 to C60 substituted or non-substituted heteroarylene group, or a C6 to C60 substituted or non-substituted condensation polycyclic group, $R_5$ is a C6 to C12 aryl group, and n is an integer of 1 to 10.

2. The organic compound of claim 1, wherein the n amount of Ar$_1$ are the same as or different from each other, and two or more Ar$_1$ among the n amount of Ar$_1$ are fused to each other or linked to each other by a single bond.

3. The organic compound of claim 1, comprising at least one selected from compounds of Chemical Formula 2 to Chemical Formula 70:

[Chemical Formula 2]

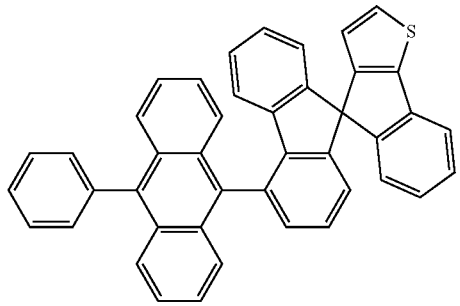

[Chemical Formula 3]

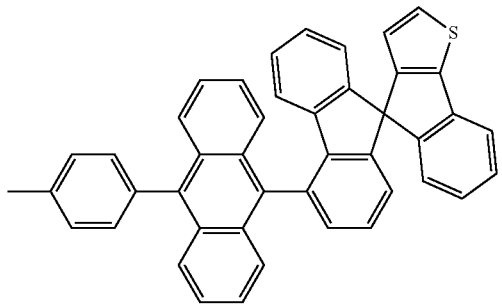

[Chemical Formula 4]

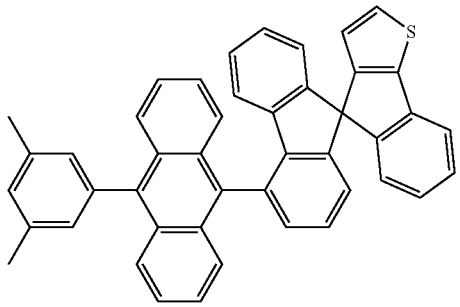

[Chemical Formula 5]

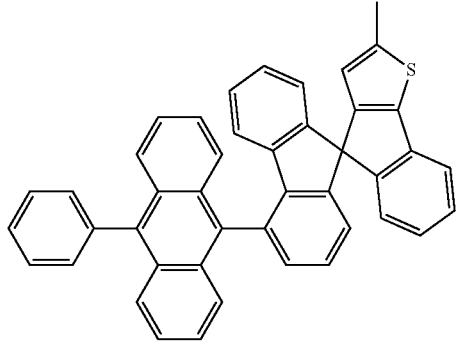

[Chemical Formula 6]
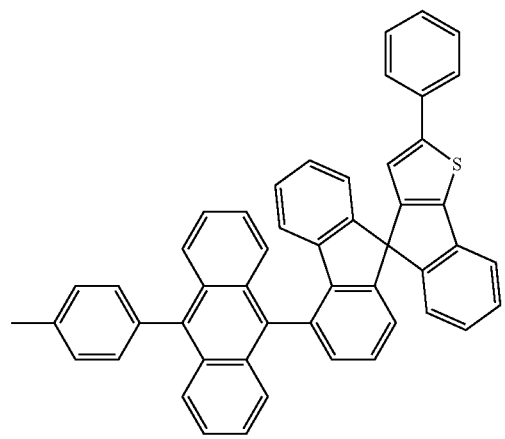
[Chemical Formula 7]
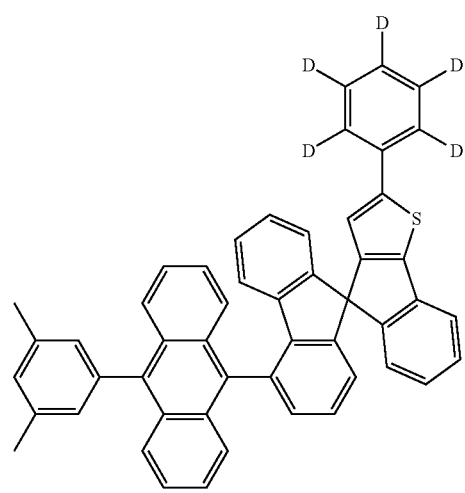
[Chemical Formula 8]
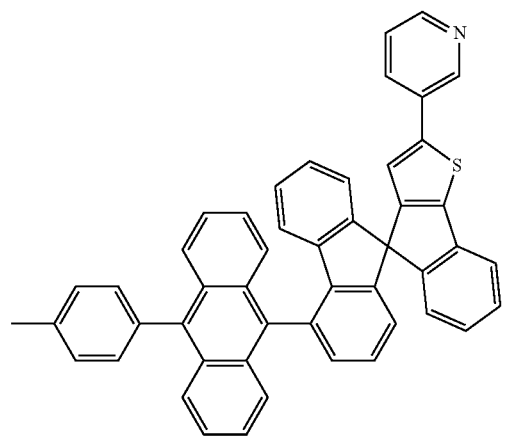
[Chemical Formula 9]
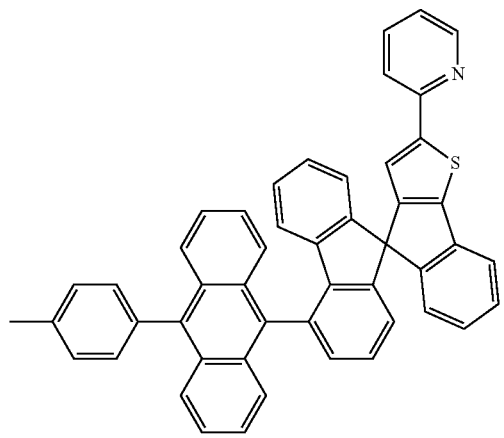
[Chemical Formula 10]
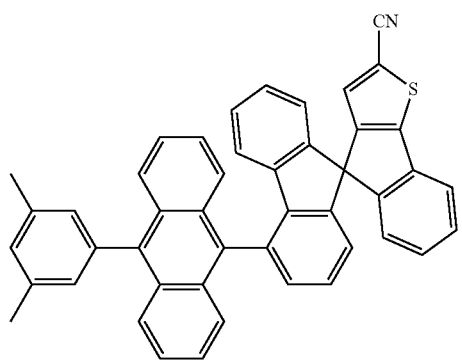
[Chemical Formula 11]
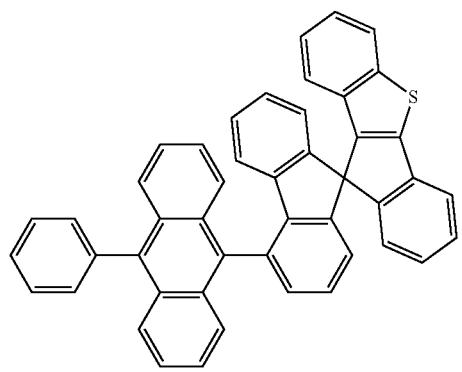
[Chemical Formula 12]
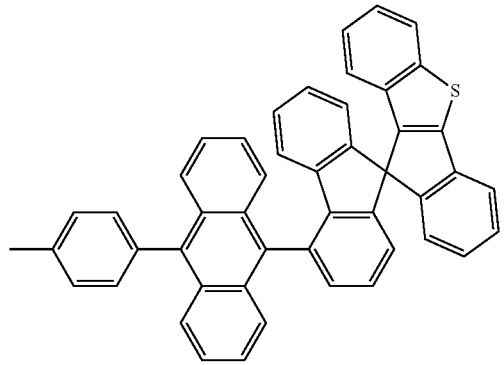

[Chemical Formula 13]
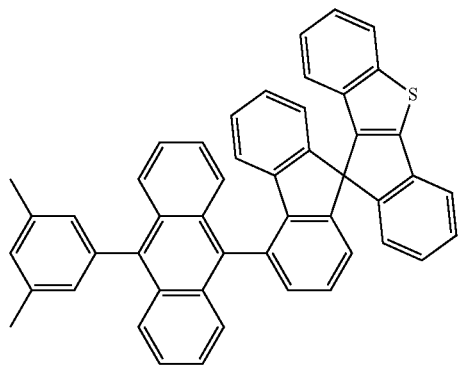
[Chemical Formula 14]
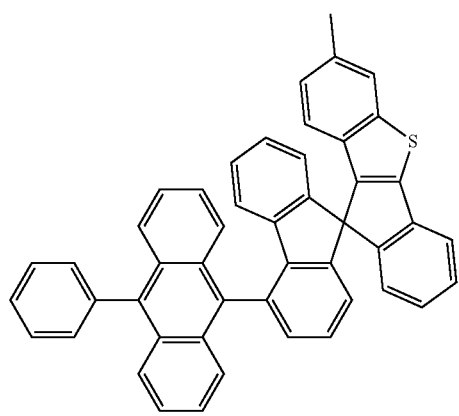
[Chemical Formula 15]
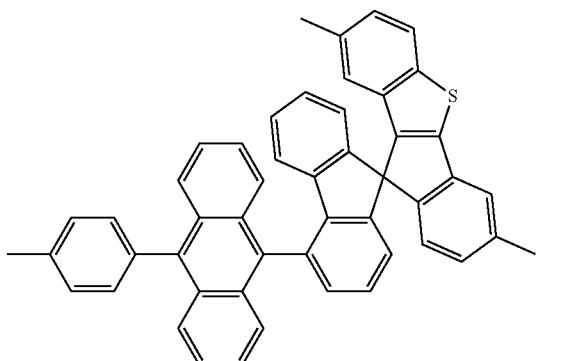
[Chemical Formula 16]
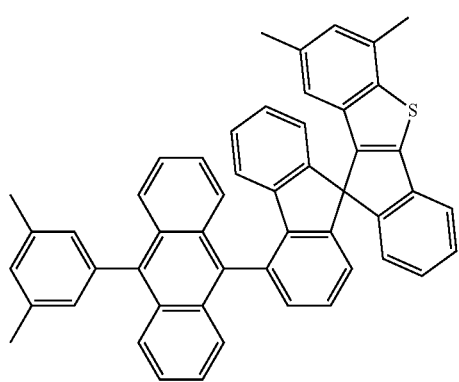
[Chemical Formula 17]
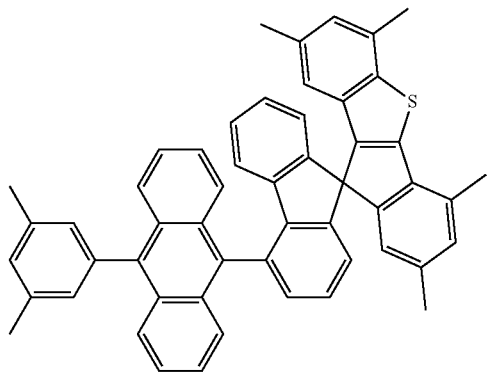
[Chemical Formula 18]
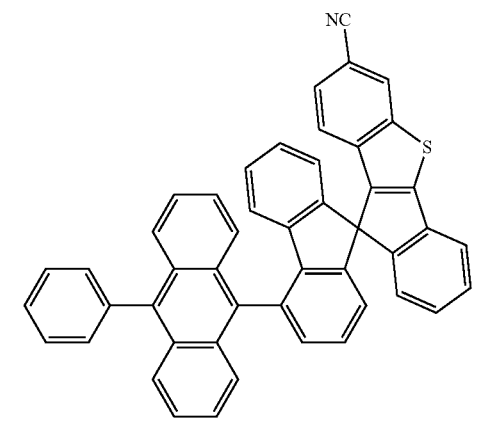
[Chemical Formula 19]
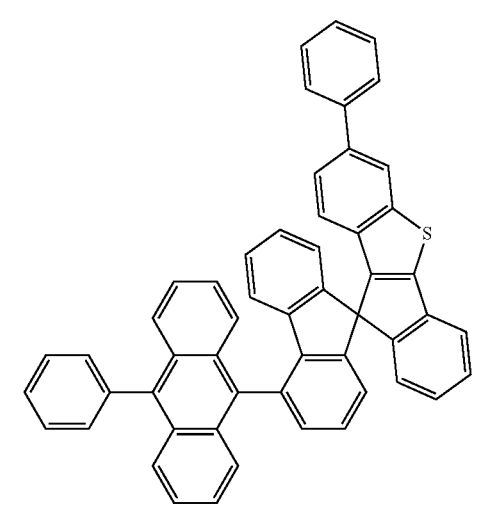

[Chemical Formula 20]
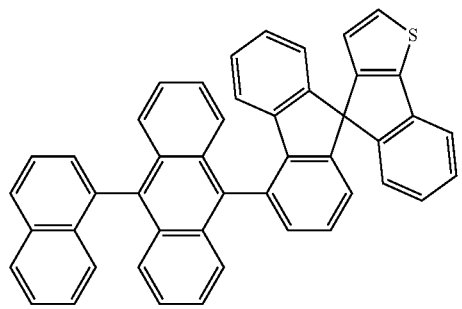
[Chemical Formula 21]
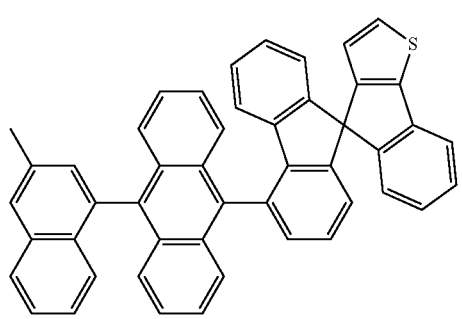
[Chemical Formula 22]
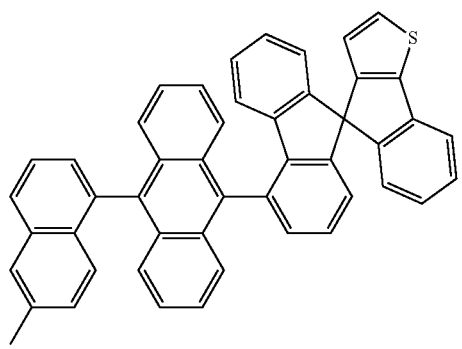
[Chemical Formula 23]
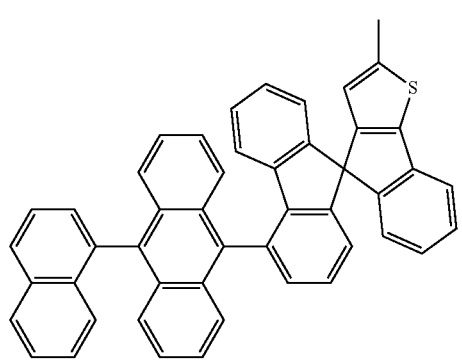
[Chemical Formula 24]
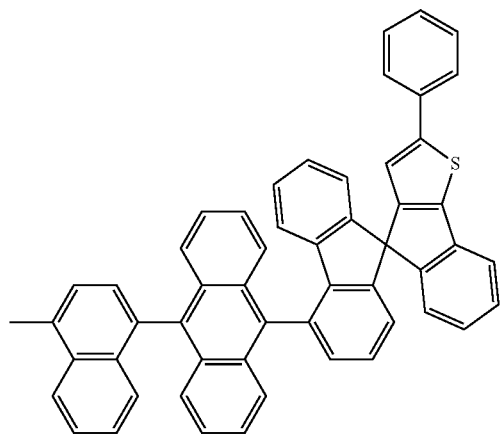
[Chemical Formula 25]
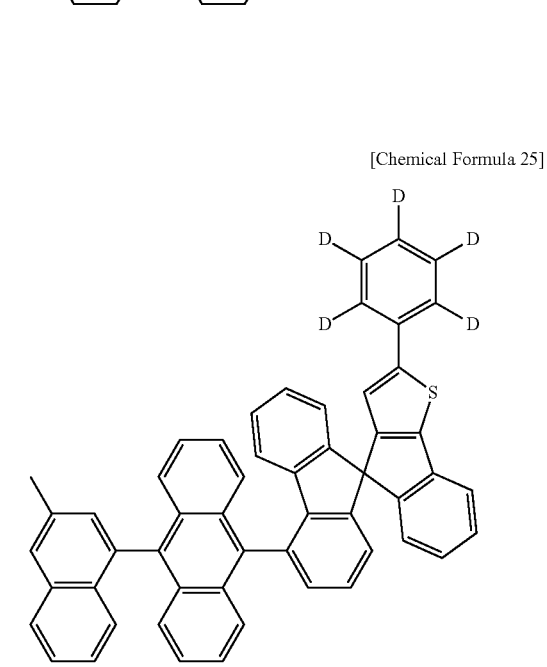
[Chemical Formula 26]
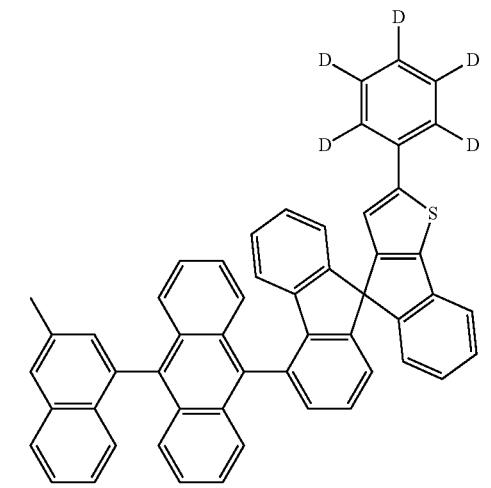

[Chemical Formula 27]
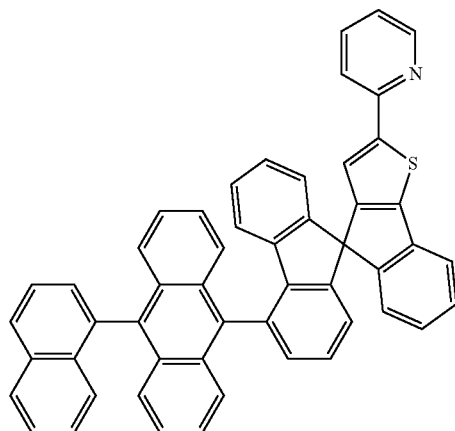
[Chemical Formula 28]
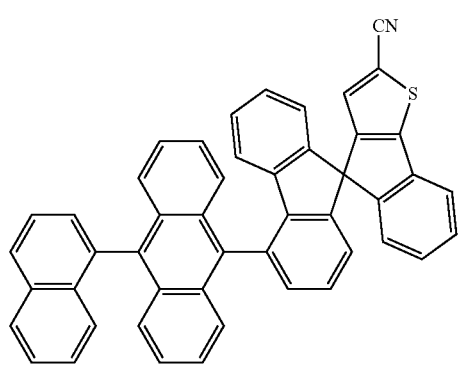
[Chemical Formula 29]
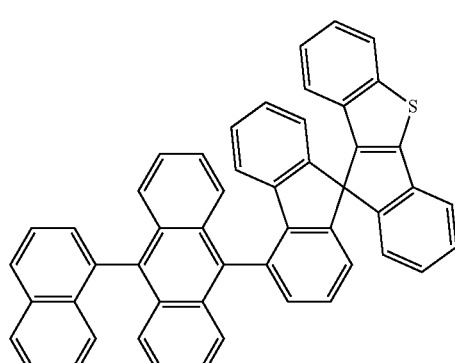
[Chemical Formula 30]
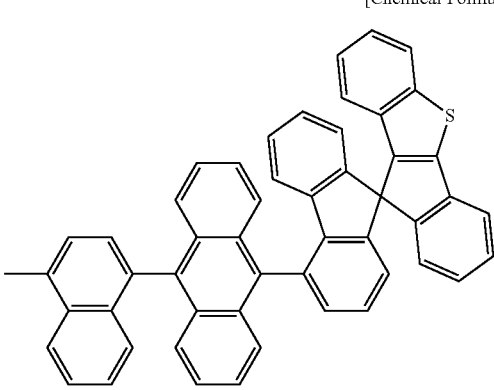
[Chemical Formula 31]
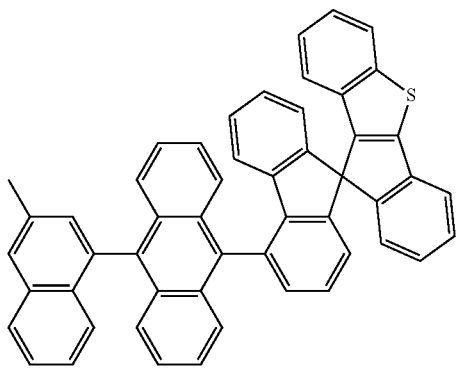
[Chemical Formula 32]
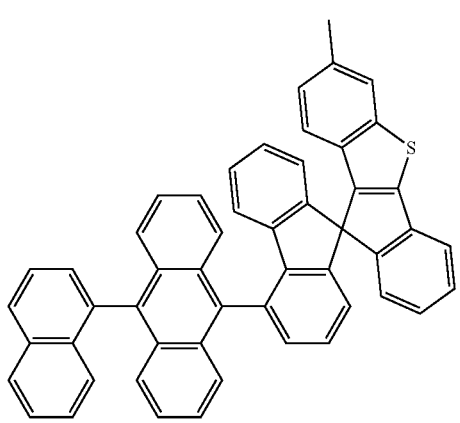
[Chemical Formula 33]
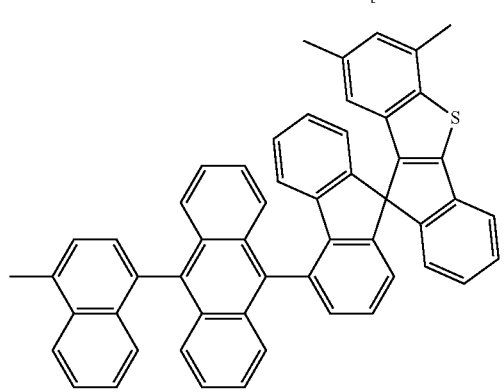
[Chemical Formula 34]
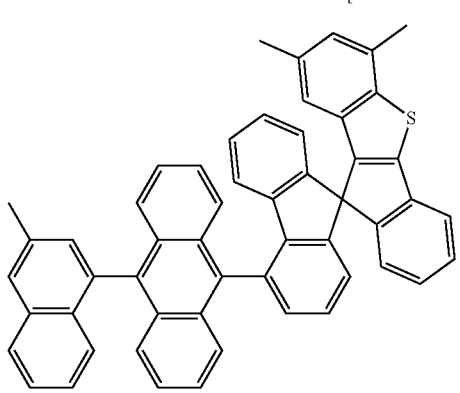

[Chemical Formula 35]
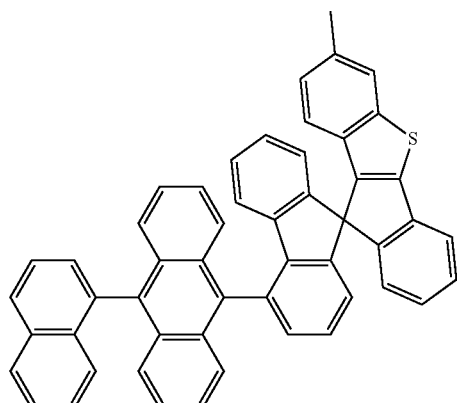
[Chemical Formula 36]
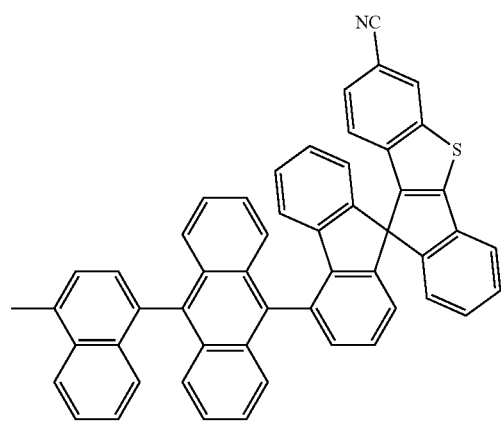
[Chemical Formula 37]
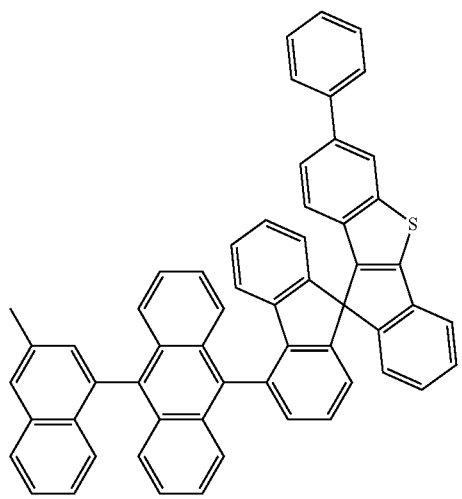
[Chemical Formula 38]
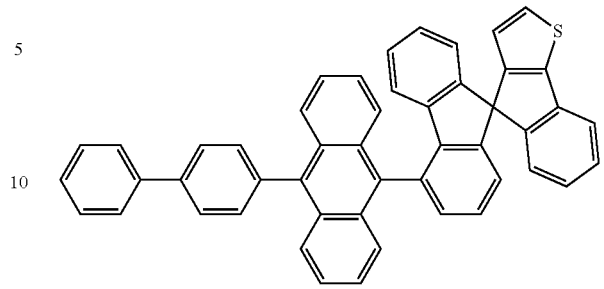
[Chemical Formula 39]
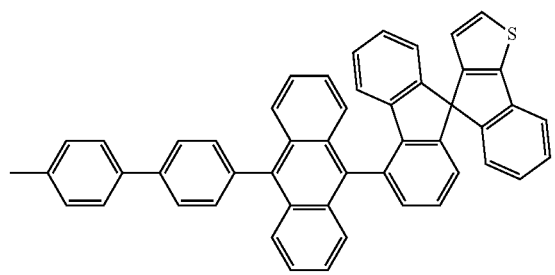
[Chemical Formula 40]
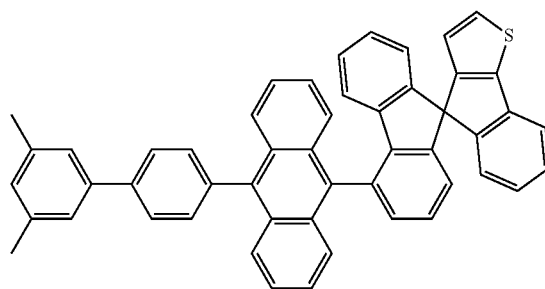
[Chemical Formula 41]
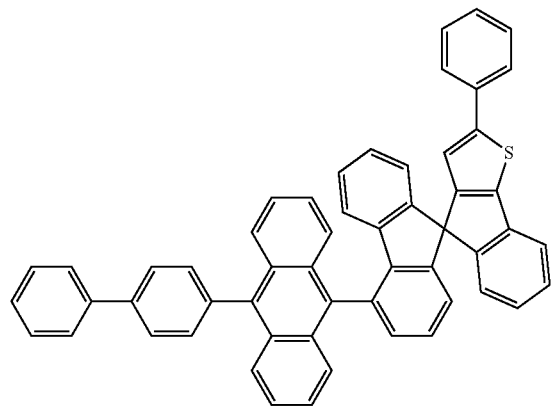

[Chemical Formula 42]
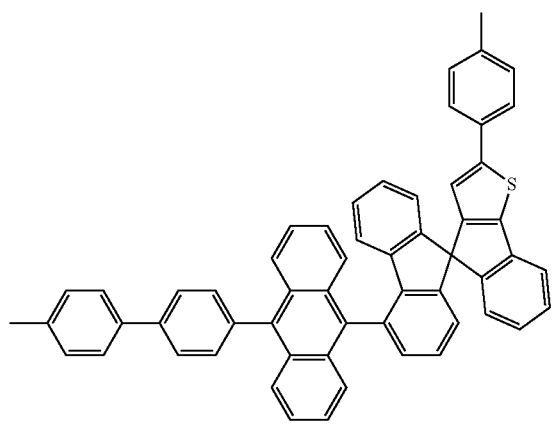
[Chemical Formula 43]
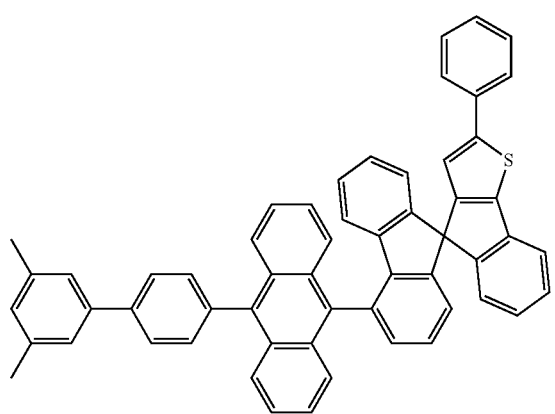
[Chemical Formula 44]
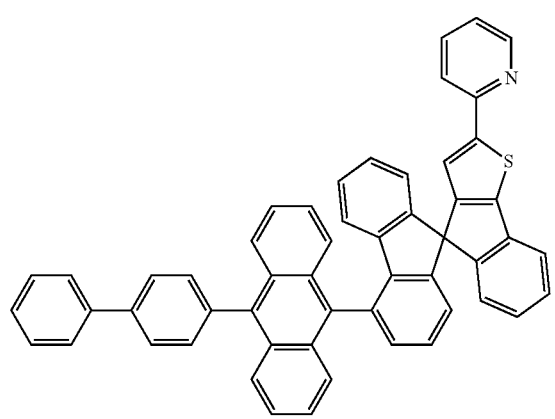
[Chemical Formula 45]
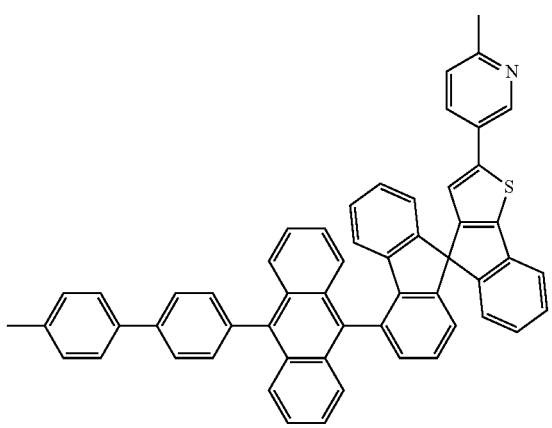
[Chemical Formula 46]
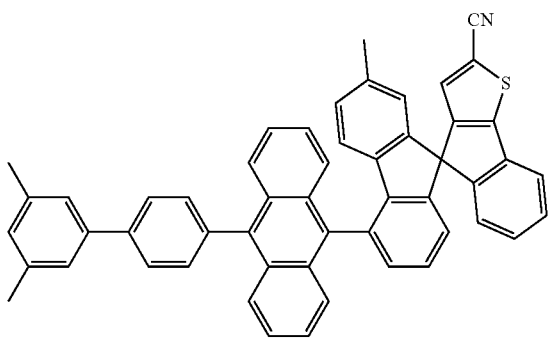
[Chemical Formula 47]
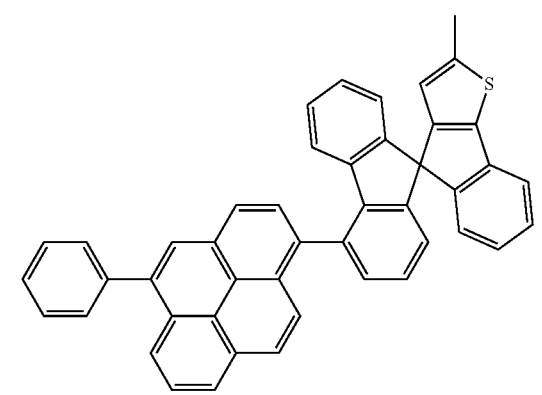
[Chemical Formula 48]
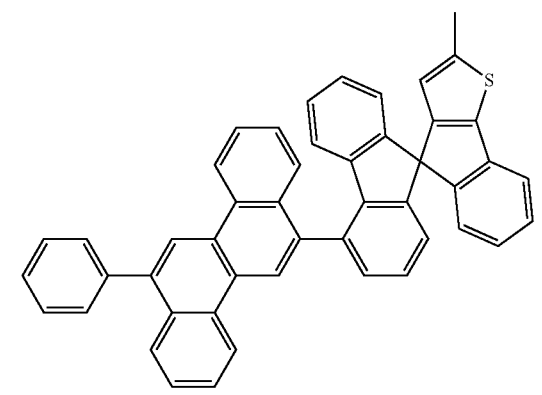

[Chemical Formula 49]
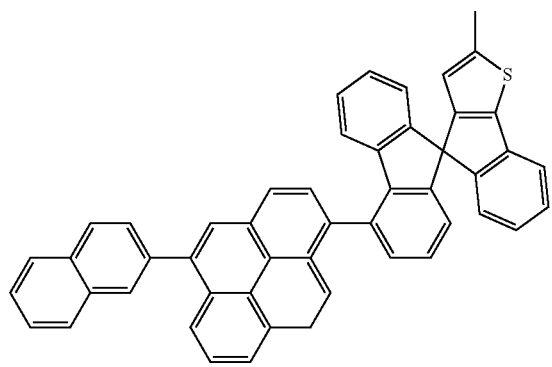
[Chemical Formula 50]
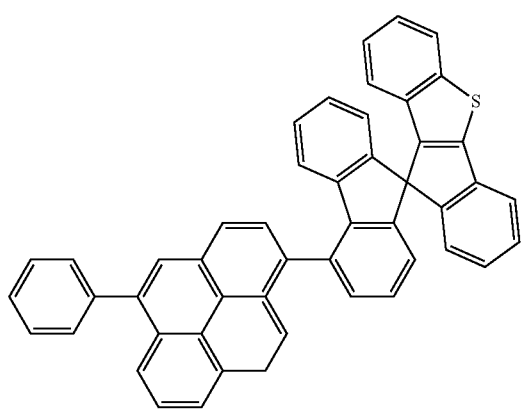
[Chemical Formula 51]
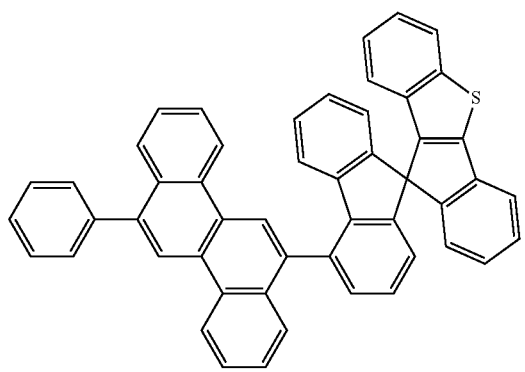
[Chemical Formula 52]
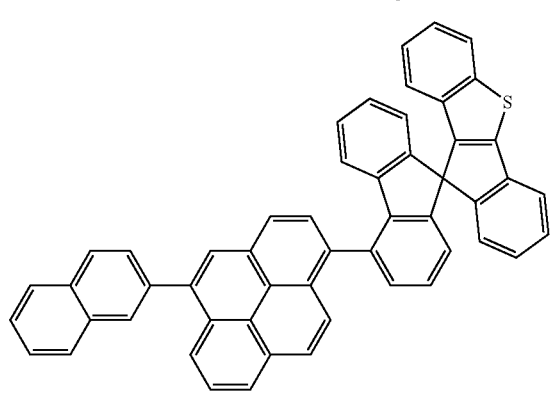
[Chemical Formula 53]
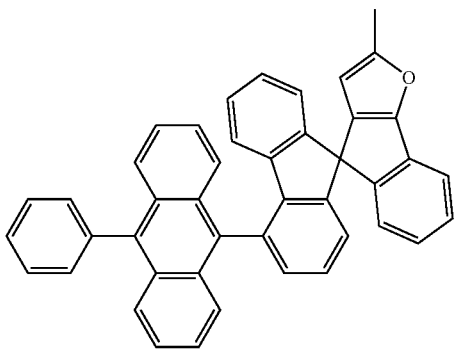
[Chemical Formula 54]
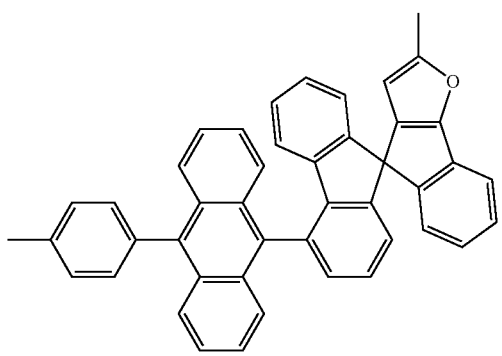
[Chemical Formula 55]
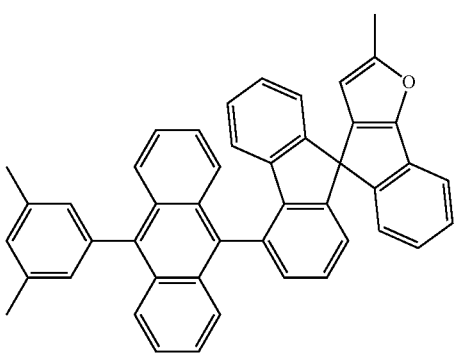
[Chemical Formula 56]
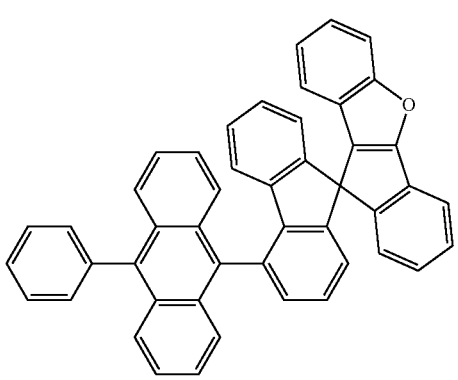

[Chemical Formula 57]
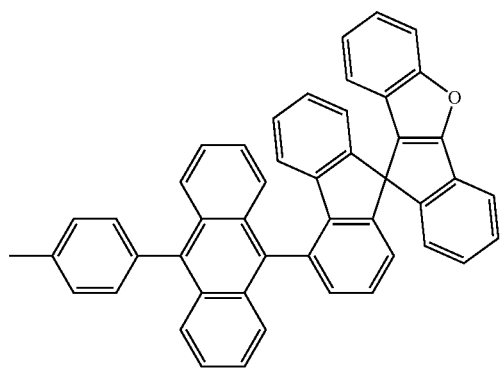
[Chemical Formula 58]
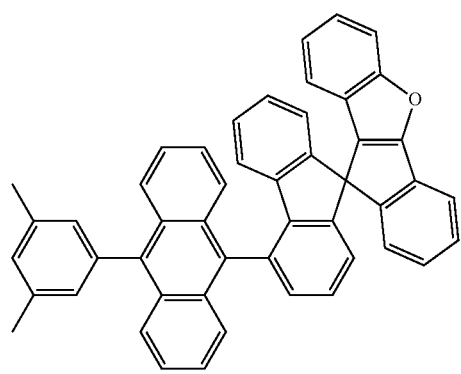
[Chemical Formmula 59]
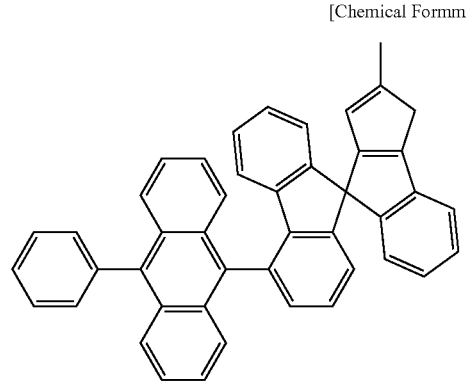
[Chemical Formula 60]
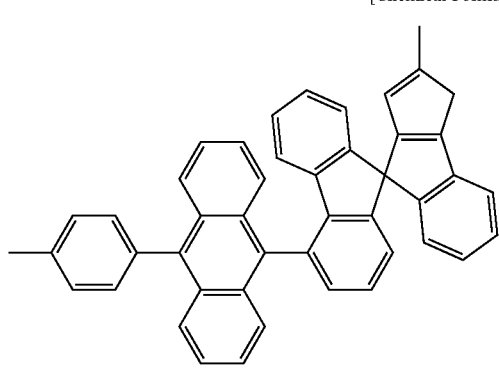
[Chemical Formula 61]
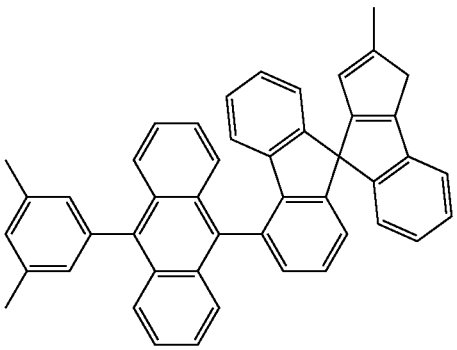
[Chemical Formula 62]
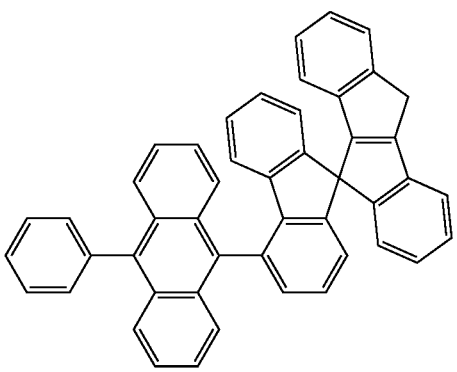
[Chemical Formula 63]
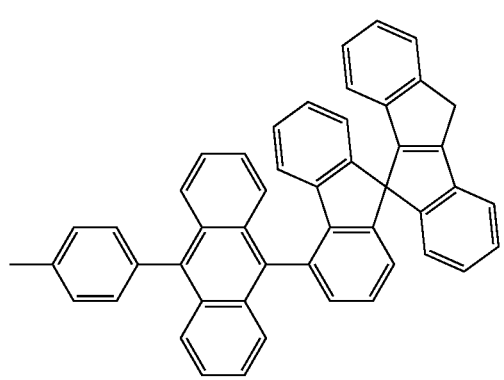
[Chemical Formula 64]
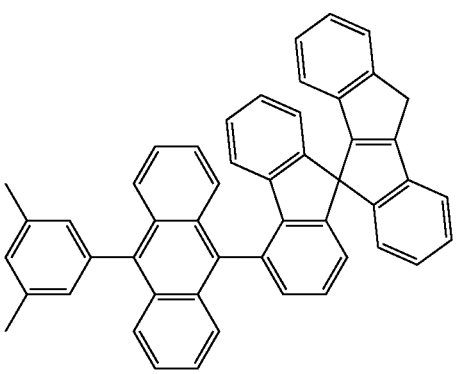

[Chemical Formula 65]
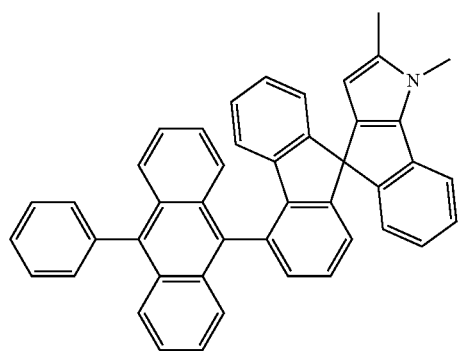
[Chemical Formula 66]
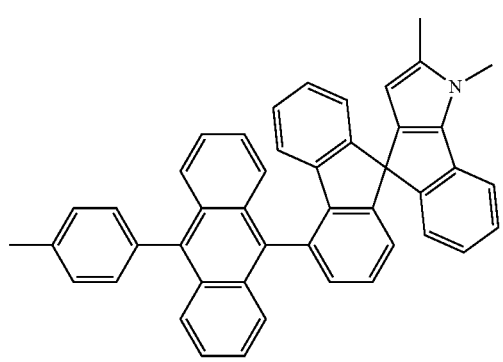
[Chemical Formula 67]
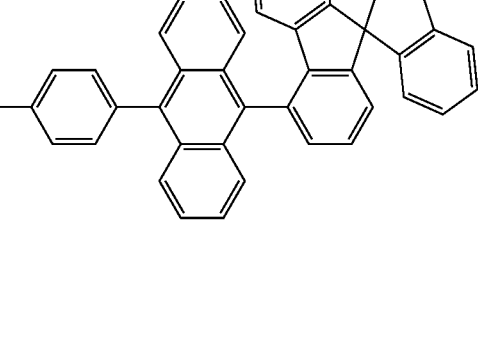
[Chemical Formula 68]
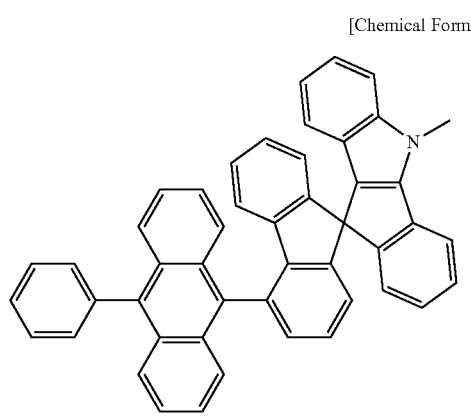
[Chemical Formula 69]
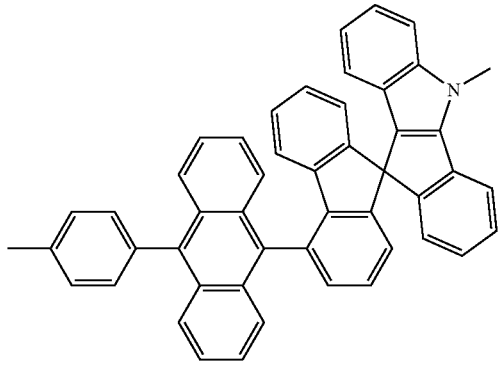
[Chemical Formula 70]
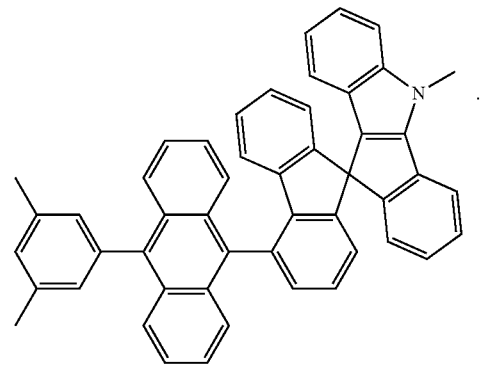
4. The organic compound of claim 1, wherein the organic compound is a compound of Chemical Formula 5:
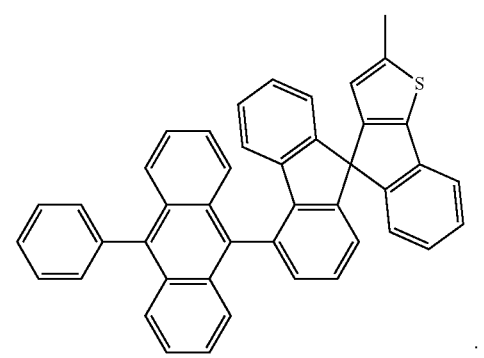 [SMILES: Cc1cc2c(s1)-c1ccccc1C21c2ccccc2-c2c(-c3c4ccccc4c(-c4ccccc4)c4ccccc34)cccc21]
5. The organic compound of claim 1, wherein the organic compound is a compound of Chemical Formula 11:

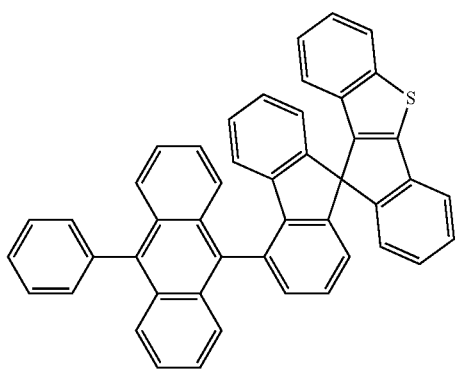

6. The organic compound of claim 1, wherein the organic compound is a compound of Chemical Formula 23:

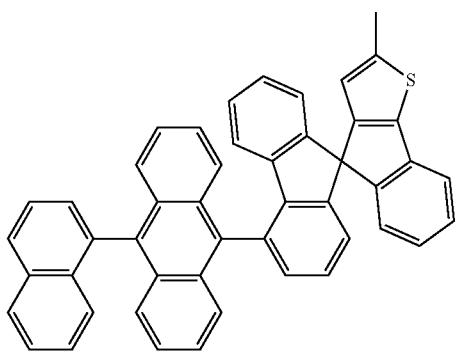

7. The organic compound of claim 1, wherein the organic compound is a compound of Chemical Formula 29:

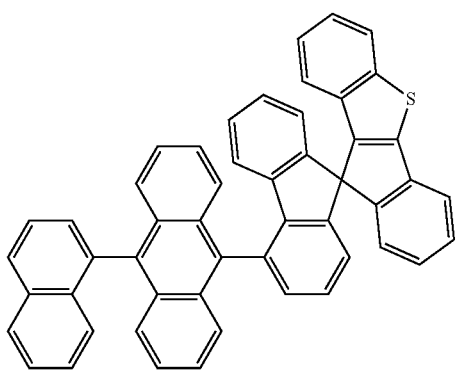

8. An organic emitting diode device comprising:
a first electrode;
a second electrode; and
an organic layer interposed between the first electrode and the second electrode,
wherein the organic layer includes an organic compound of Chemical Formula 1:

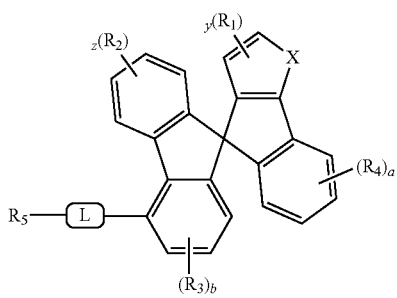

wherein $R_1$ to $R_5$ are each a hydrogen atom, a heavy hydrogen, a C1 to C60 substituted or non-substituted alkyl group, a C2 to C60 substituted or non-substituted alkenyl group, a C2 to C60 substituted or non-substituted alkynyl group, a C3 to C60 substituted or non-substituted cycloalkyl group, a C1 to C60 substituted or non-substituted alkoxy group, a C5 to C60 substituted or non-substituted aryloxy group, a C5 to C60 substituted or non-substituted arylthio group, a C5 to C60 substituted or non-substituted aryl group, an amino group substituted into a C3 to C60 heteroaryl group, a C3 to C60 substituted or non-substituted heteroaryl group, a C6 to C60 substituted or non-substituted condensation polycyclic group, a halogen atom, a cyano group, a nitro group, a hydroxyl group, or a carboxyl group, $R_1$ and $R_2$ are the same or different from each other, X is a linking group represented by —S—, —O—, —C($R_6$)($R_7$)—, or —N($R_6$)—, $R_6$ and $R_7$ are independently a hydrogen atom, a heavy hydrogen, a C1 to C20 substituted or non-substituted alkyl group, a C5 to C20 substituted or non-substituted aryl group, a C3 to C20 substituted or non-substituted hetero aryl group, a C6 to C20 substituted or non-substituted condensation polycyclic group, a halogen atom, a cyano group, a nitro group, a hydroxyl group, or a carboxyl group, a and z are each an integer of 0 to 4, b is an integer of 0 to 3, and y is an integer of 0 to 2, L is a divalent linking group represented by —(Ar$_1$)$_n$—, wherein Ar$_1$ is a C5 to C60 substituted or non-substituted arylene group, a C3 to C60 substituted or non-substituted heteroarylene group, or a C6 to C60 substituted or non-substituted condensation polycyclic group, $R_5$ is a C6 to C12 aryl group, and n is an integer of 1 to 10.

9. The organic emitting diode device of claim 8, wherein the n amount of Ar$_1$ are the same as or different from each other, and two or more Ar$_1$ among the n amount of Ar$_1$ are fused to each other or linked to each other by a single bond.

10. The organic emitting diode device of claim 9, comprising at least one selected from compounds of Chemical Formula 2 to Chemical Formula 70:

[Chemical Formula 2]
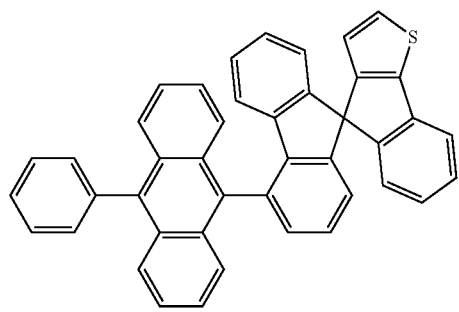
[Chemical Formula 3]
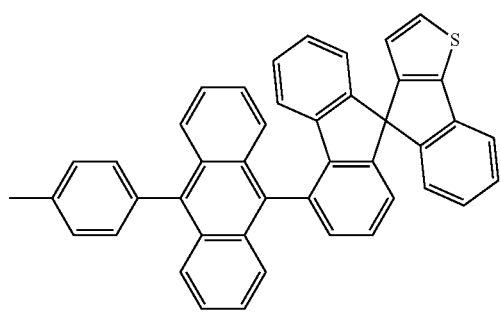
[Chemical Formula 4]
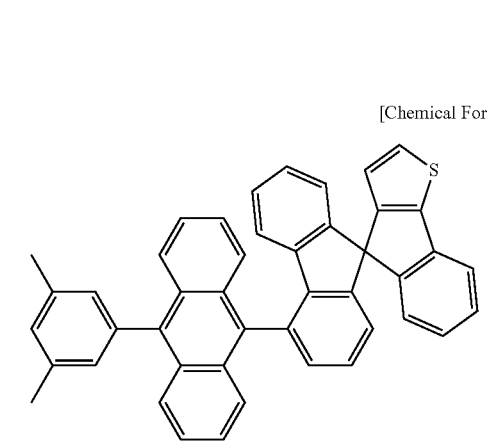
[Chemical Formula 5]
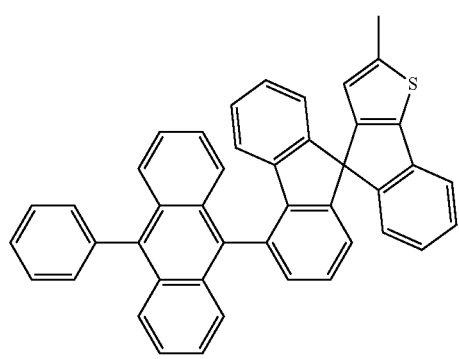
[Chemical Formula 6]
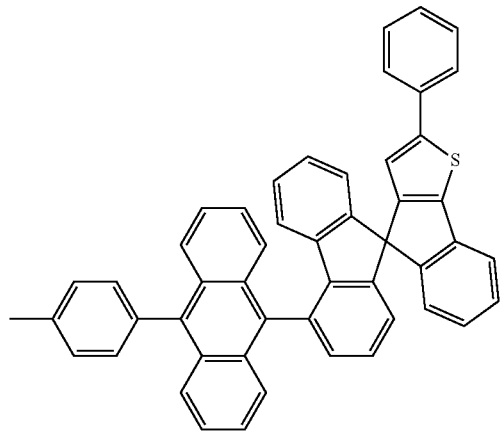
[Chemical Formula 7]
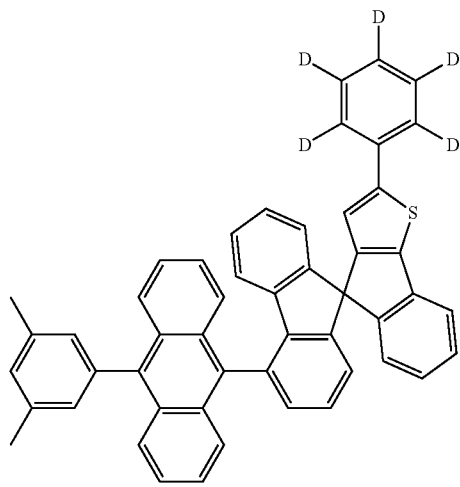
[Chemical Formula 8]
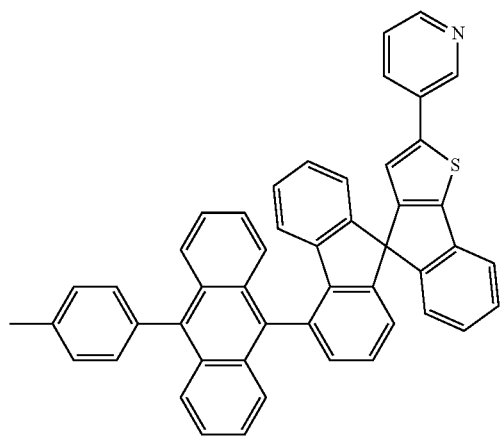

[Chemical Formula 9]
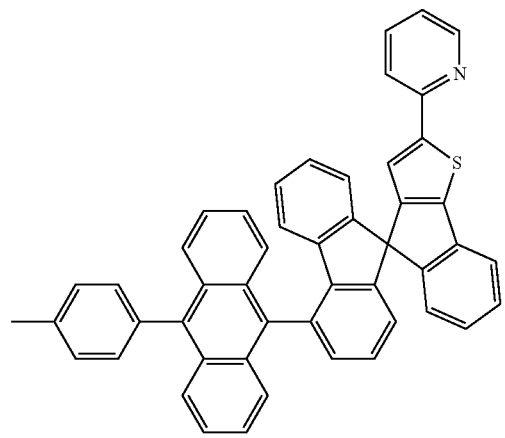
[Chemical Formula 10]
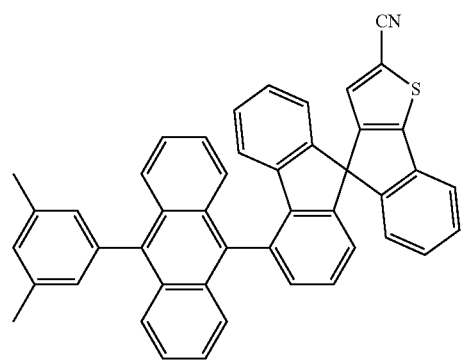
[Chemical Formula 11]
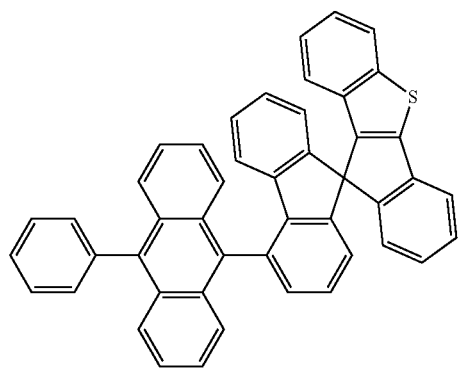
[Chemical Formula 12]
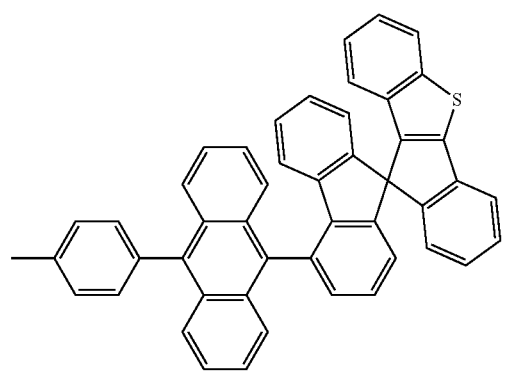
[Chemical Formula 13]
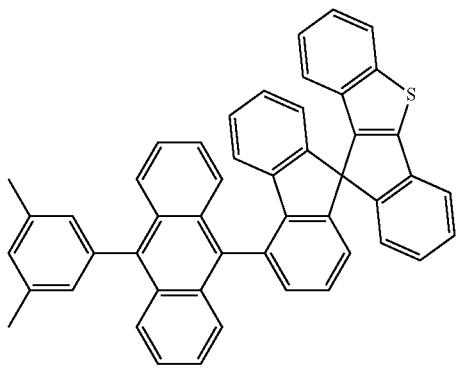
[Chemical Formula 14]
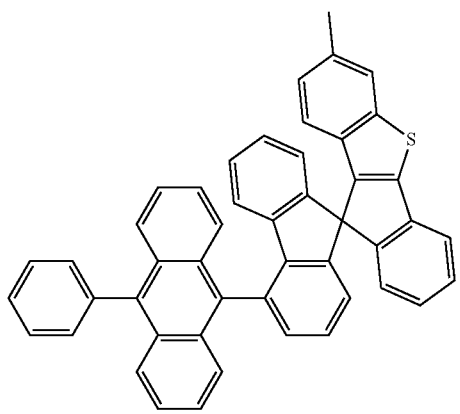
[Chemical Formula 15]
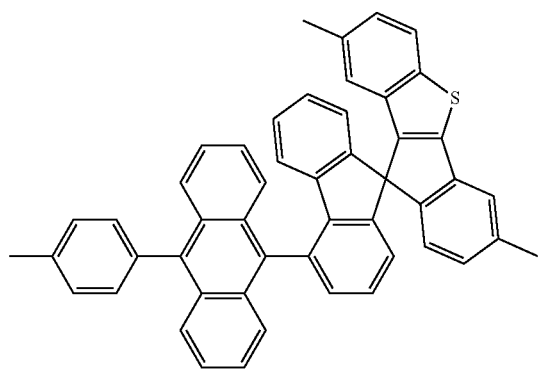
[Chemical Formula 16]
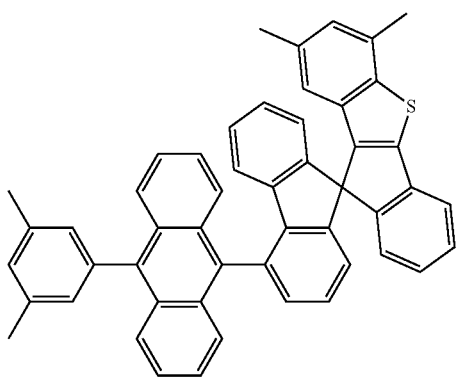

[Chemical Formula 17]
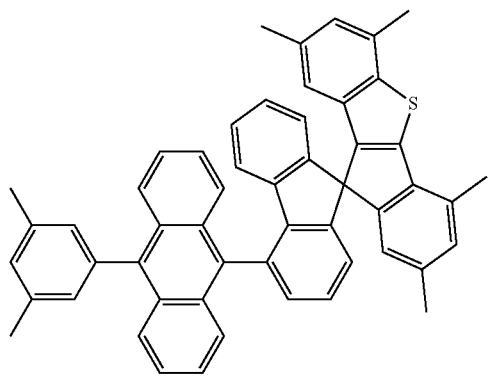
[Chemical Formula 18]
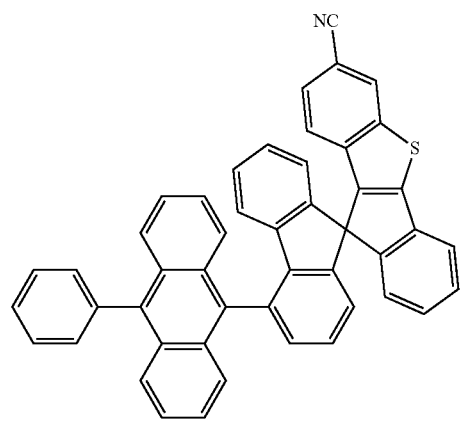
[Chemical Formula 19]
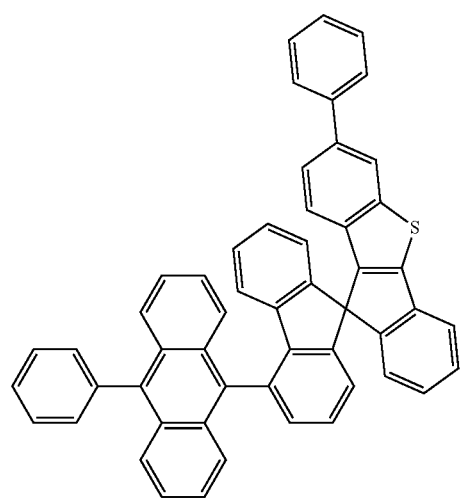
[Chemical Formula 20]
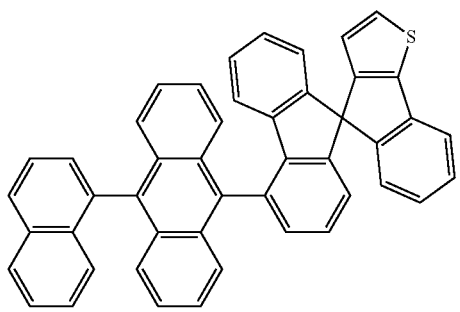
[Chemical Formula 21]
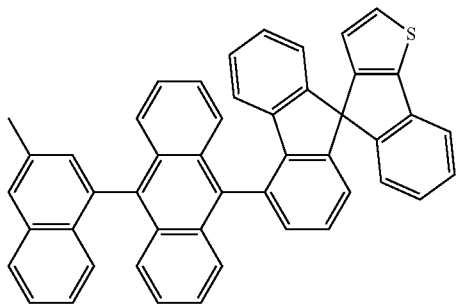
[Chemical Formula 22]
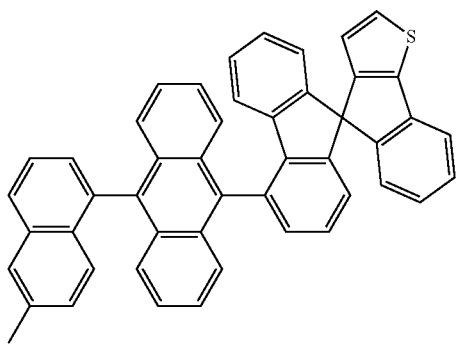
[Chemical Formula 23]
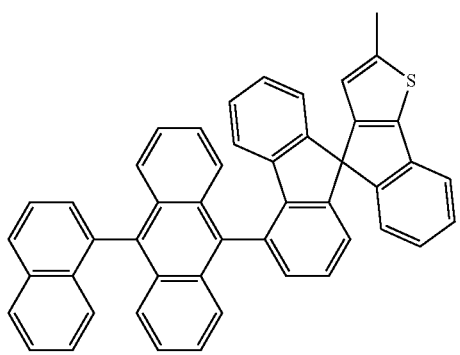

[Chemical Formula 24]
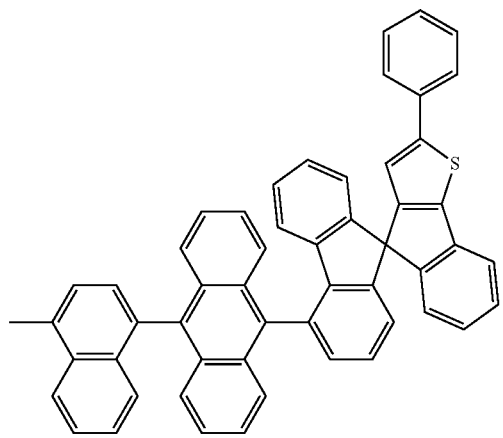
[Chemical Formula 25]
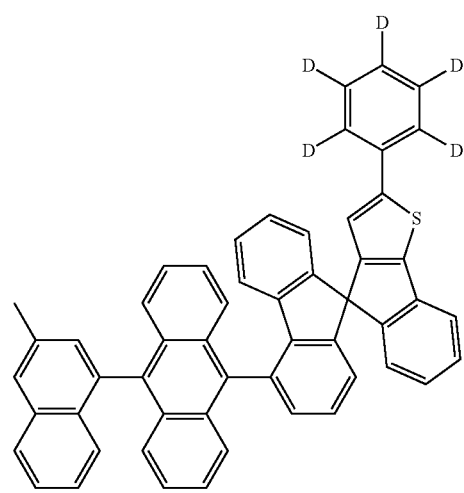
[Chemical Formula 26]
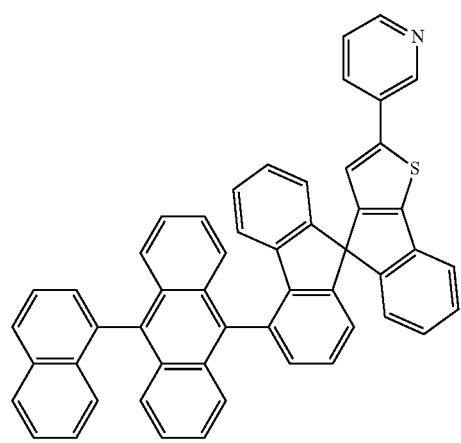
[Chemical Formula 27]
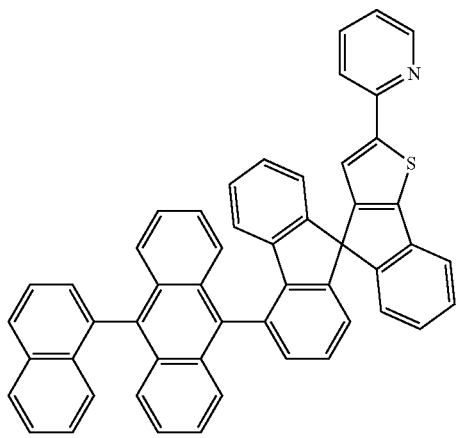
[Chemical Formula 28]
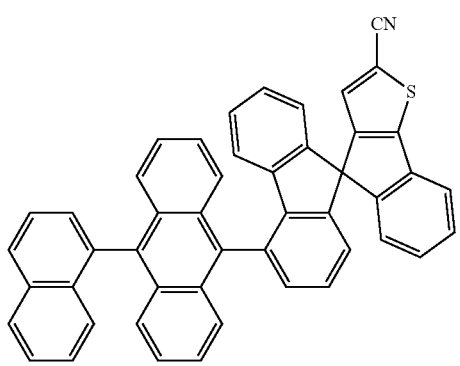
[Chemical Formula 29]
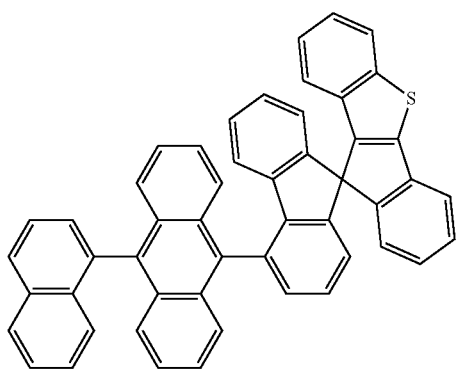
[Chemical Formula 30]
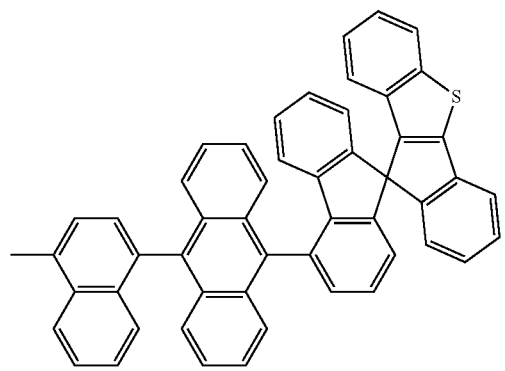

[Chemical Formula 31]
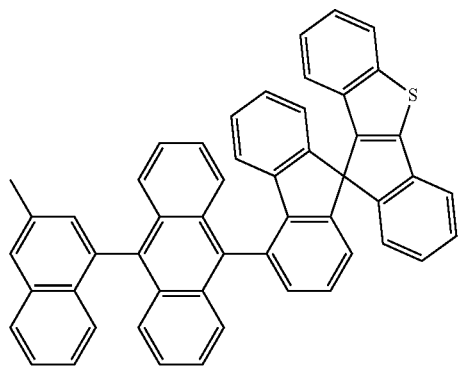
[Chemical Formula 32]
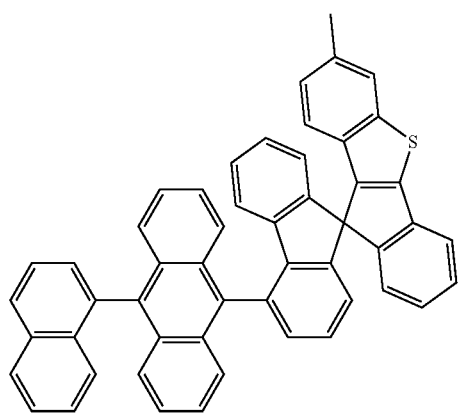
[Chemical Formula 33]
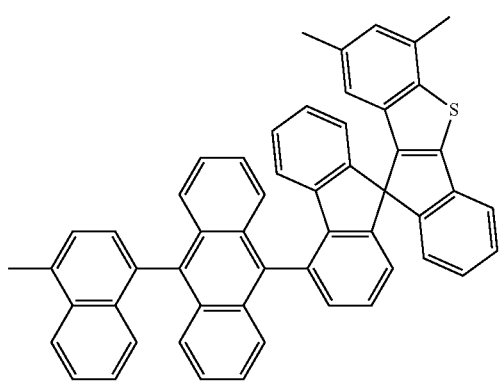
[Chemical Formula 34]
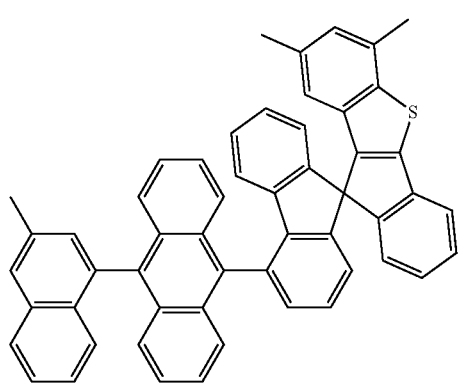
[Chemical Formula 35]
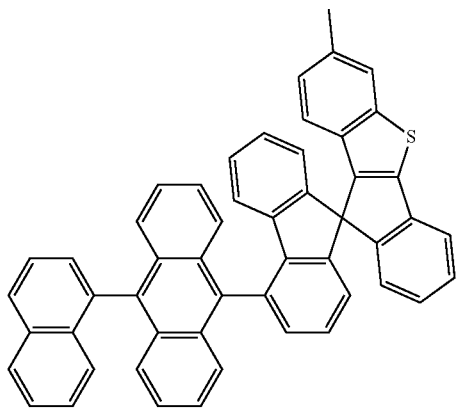
[Chemical Formula 36]
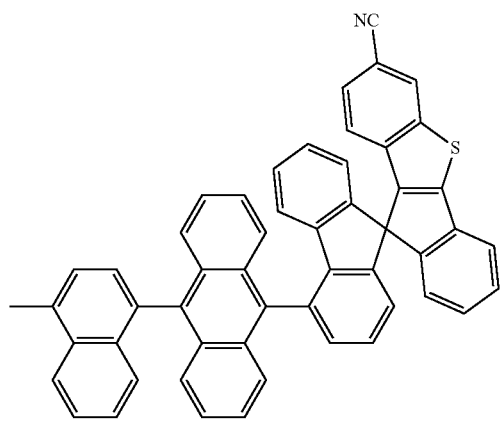
[Chemical Formula 37]
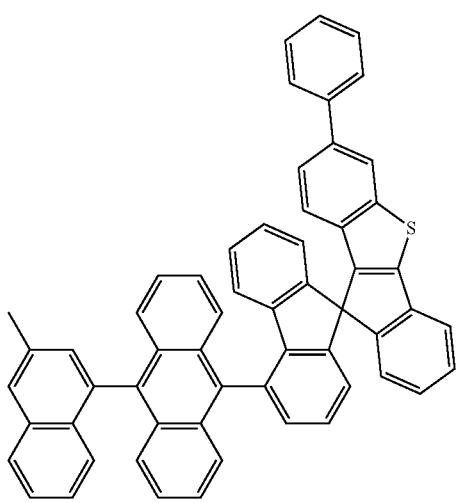

[Chemical Formula 38]
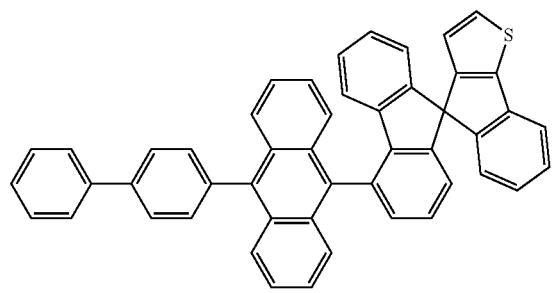
[Chemical Formula 39]
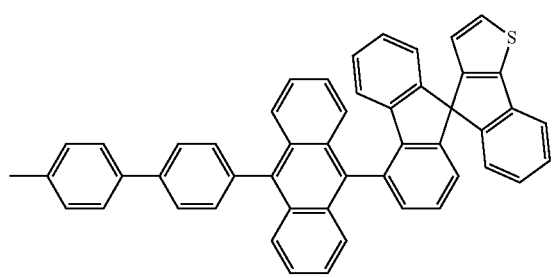
[Chemical Formula 40]
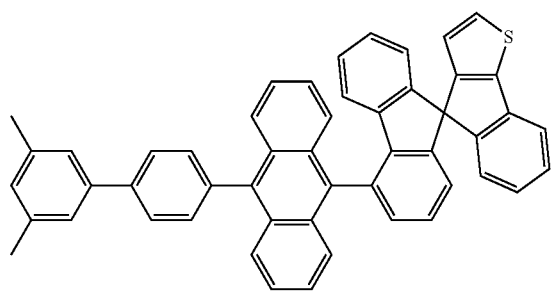
[Chemical Formula 41]
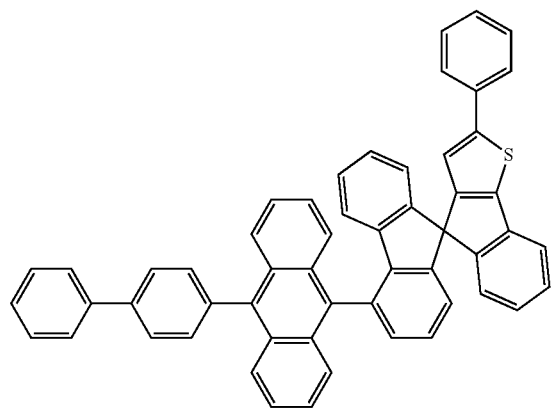
[Chemical Formula 42]
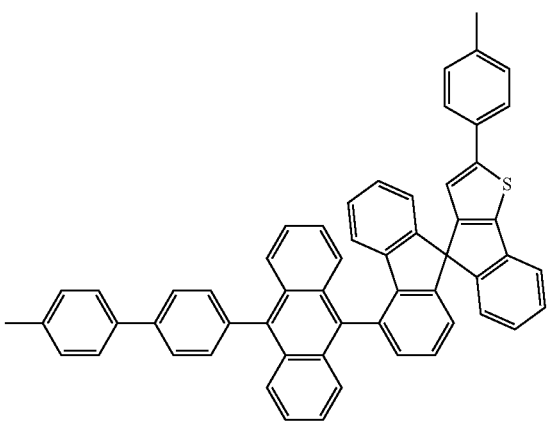
[Chemical Formula 43]
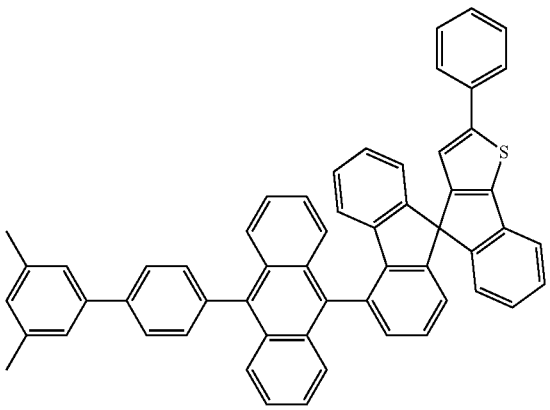
[Chemical Formula 44]
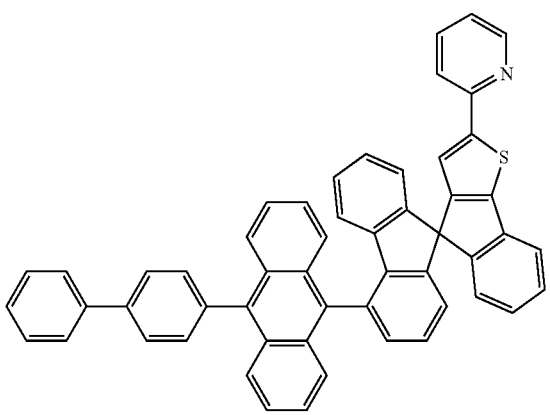

-continued
[Chemical Formula 45]
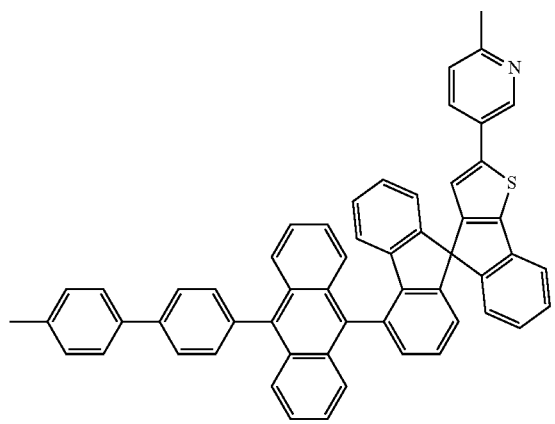
[Chemical Formula 46]
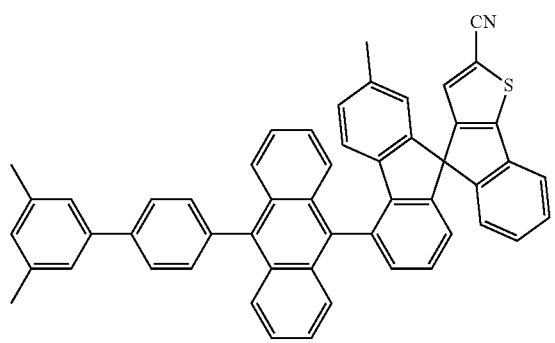
[Chemical Formula 47]
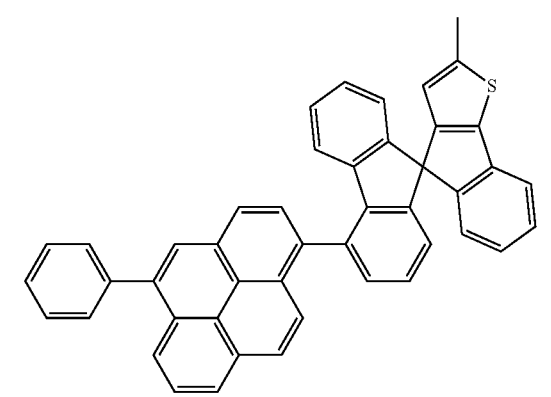
[Chemical Formula 48]
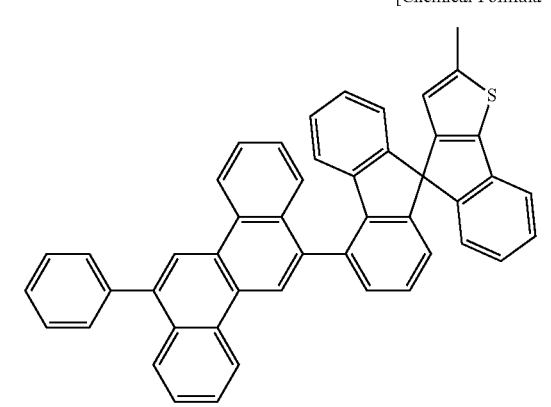
-continued
[Chemical Formula 49]
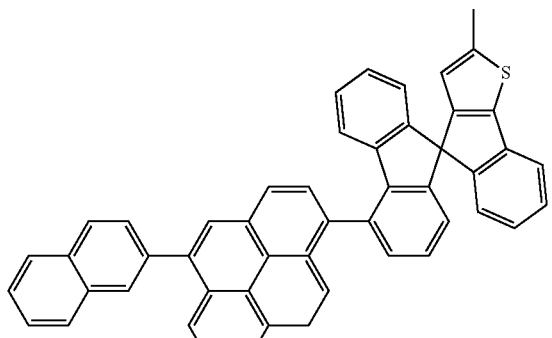
[Chemical Formula 50]
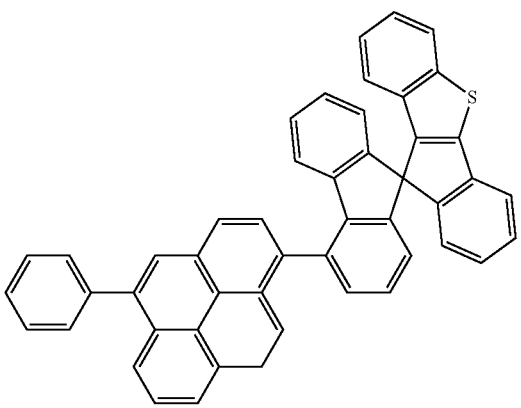
[Chemical Formula 51]
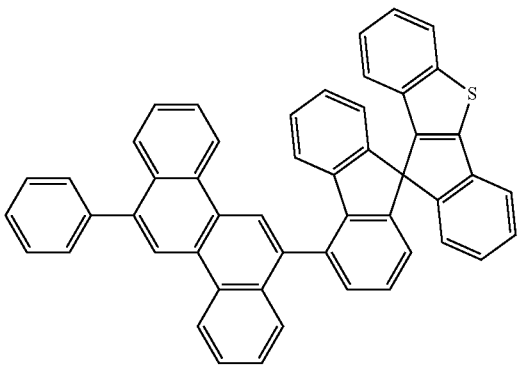
[Chemical Formula 52]
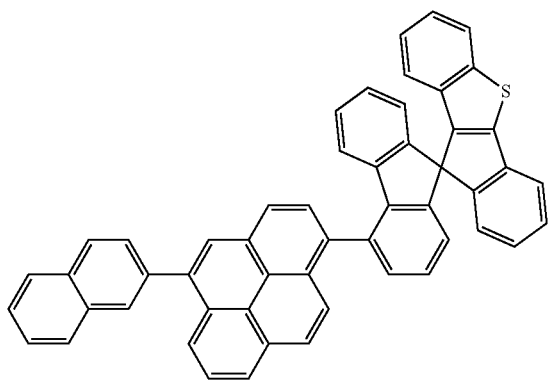

[Chemical Formula 53]
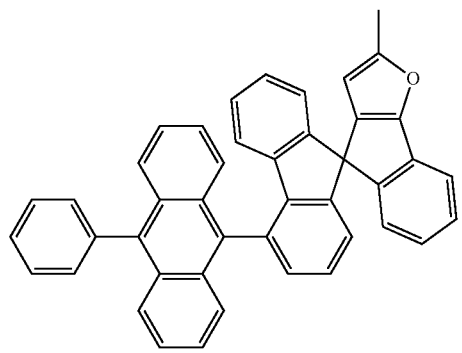
[Chemical Formula 54]
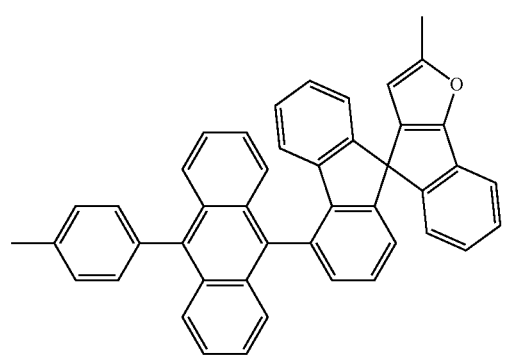
[Chemical Formula 55]
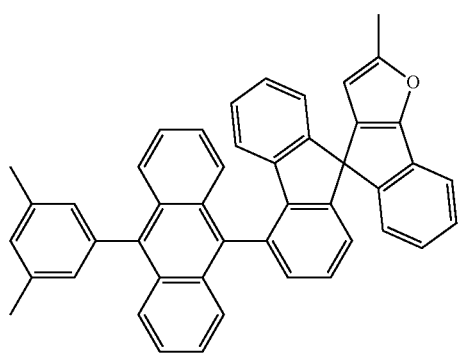
[Chemical Formula 56]
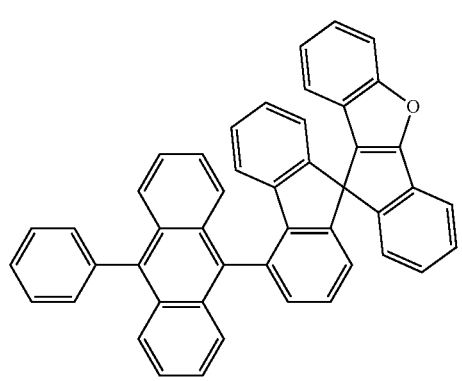
[Chemical Formula 57]
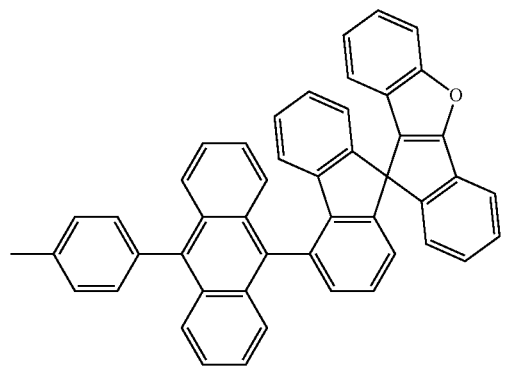
[Chemical Formula 58]
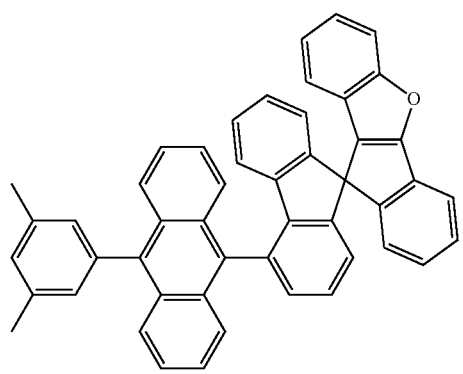
[Chemical Formula 59]
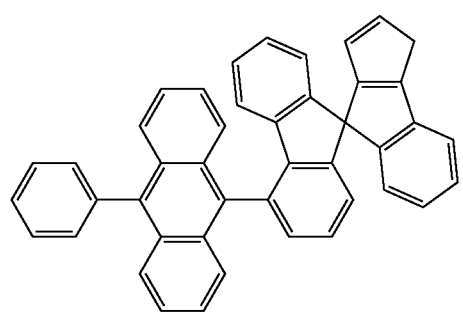
[Chemical Formula 60]
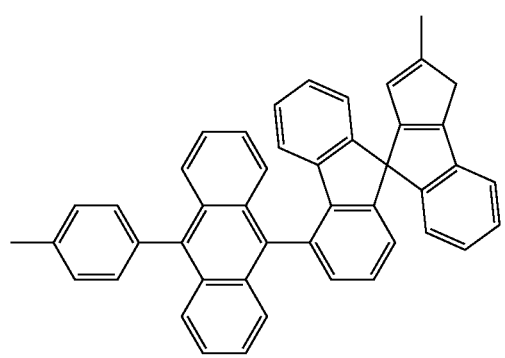

[Chemical Formula 61]
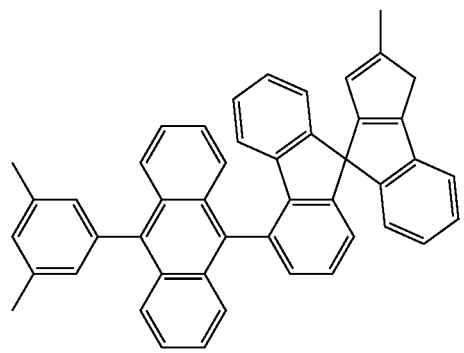
[Chemical Formula 62]
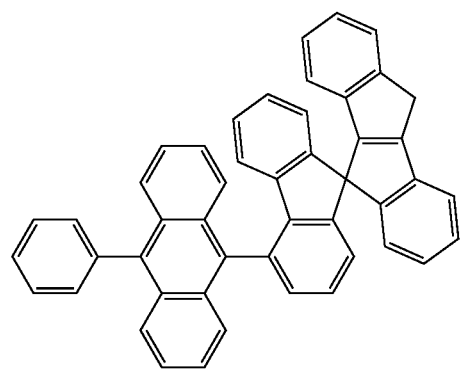
[Chemical Formula 63]
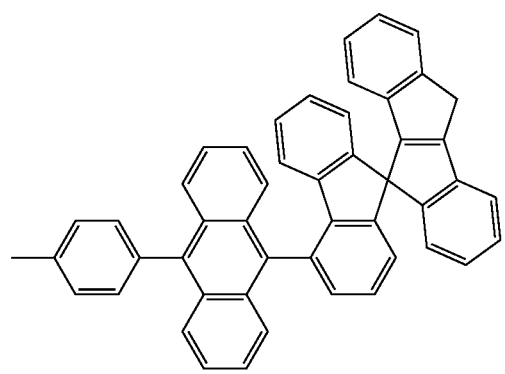
[Chemical Formula 64]
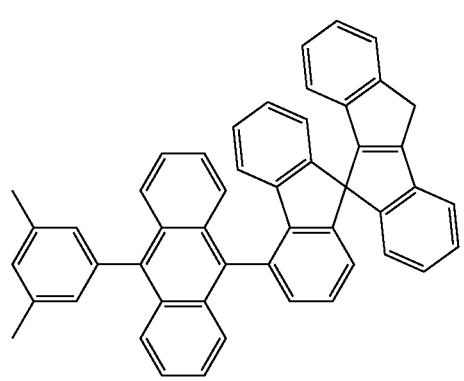
[Chemical Formula 65]
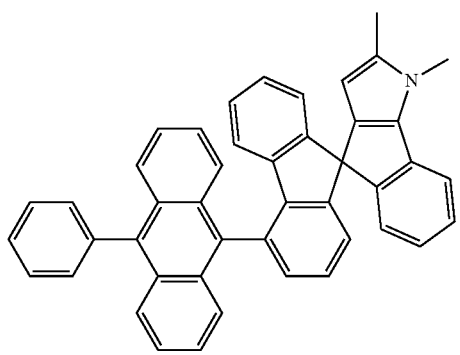
[Chemical Formula 66]
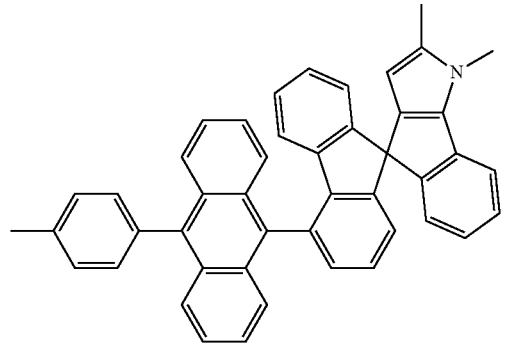
[Chemical Formula 67]
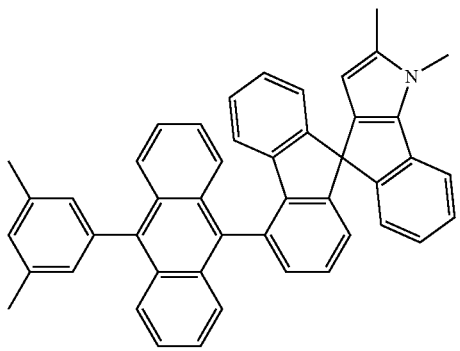
[Chemical Formula 68]
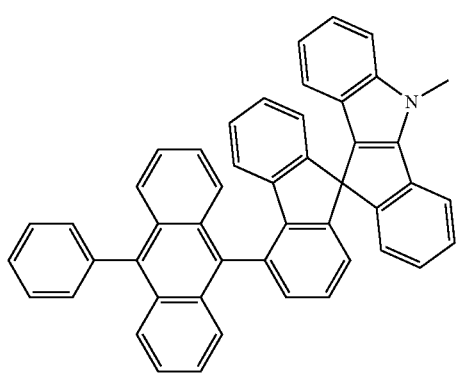

-continued

[Chemical Formula 69]

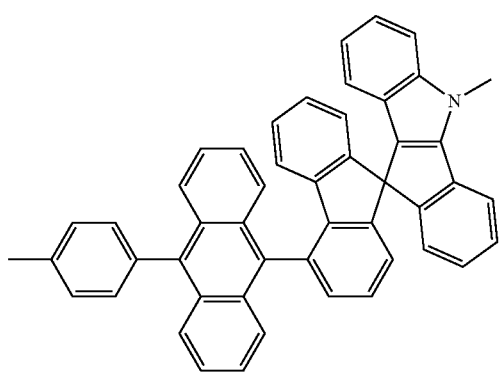

[Chemical Formula 70]

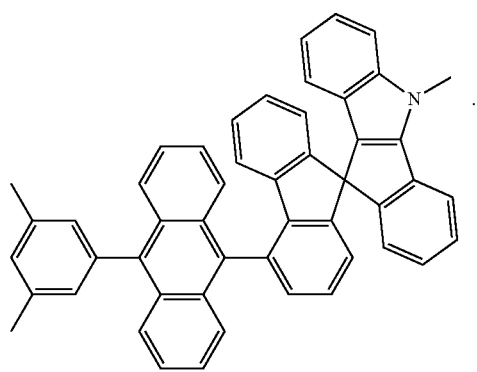

11. The organic emitting diode device of claim 10, wherein the organic layer includes an emission layer, and wherein the organic compound of Chemical Formula 1 is included in the emission layer.

12. The organic emitting diode device of claim 11, wherein the emission layer comprises the organic compound of Chemical Formula 1 as a host.

13. The organic emitting diode device of claim 11, wherein the emission layer includes the organic compound of Chemical Formula 1 as a dopant.

14. The organic emitting diode device of claim 8, wherein the first electrode is an anode, and the second electrode is a cathode.

15. The organic emitting diode device of claim 14, wherein the organic layer further comprises:
    a hole injection layer disposed between the first electrode and the emission layer,
    a hole transfer layer disposed between the hole injection layer and the emission layer,
    an electron transfer layer disposed between the emission layer and the second electrode, and
    an electron injection layer disposed between the electron transfer layer and the second electrode.

16. The organic emitting diode device of claim 8, wherein the organic compound is a compound of Chemical Formula 5:

17. The organic emitting diode device of claim 8, wherein the organic compound is a compound of Chemical Formula 11:

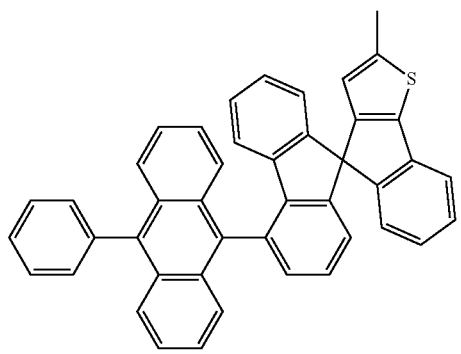

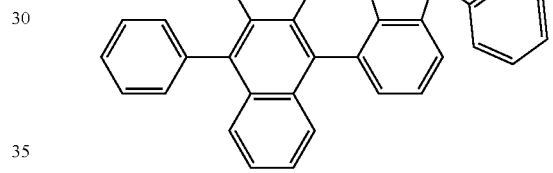

18. The organic emitting diode device of claim 8, wherein the organic compound is a compound of Chemical Formula 23:

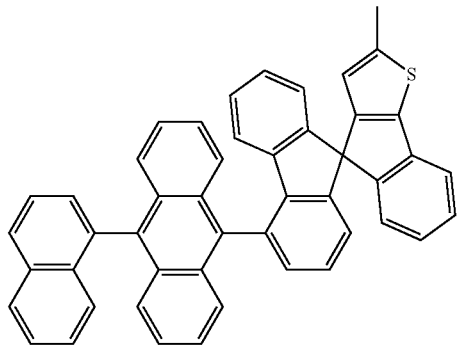

* * * * *